United States Patent
Ohsawa et al.

(10) Patent No.: US 6,916,591 B2
(45) Date of Patent: Jul. 12, 2005

(54) PHOTOACID GENERATORS, CHEMICALLY AMPLIFIED RESIST COMPOSITIONS, AND PATTERNING PROCESS

(75) Inventors: Youichi Ohsawa, Niigata-ken (JP); Katsuhiro Kobayashi, Niigata-ken (JP); Katsuya Takemura, Niigata-ken (JP); Junji Tsuchiya, Niigata-ken (JP); Kazunori Maeda, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 137 days.

(21) Appl. No.: 10/393,006

(22) Filed: Mar. 21, 2003

(65) Prior Publication Data

US 2003/0215738 A1 Nov. 20, 2003

(30) Foreign Application Priority Data

Mar. 22, 2002 (JP) ........................................ 2002-080649

(51) Int. Cl.$^7$ .............................. G03F 7/004; G03F 7/30
(52) U.S. Cl. ..................... 430/270.1; 430/326; 430/905; 430/910; 549/89
(58) Field of Search ............................. 430/270.1, 326, 430/905, 910; 403/910; 549/89

(56) References Cited

U.S. PATENT DOCUMENTS

| | | | |
|---|---|---|---|
| 5,378,715 A | * 1/1995 | Stein et al. | 514/329 |
| 6,004,724 A | 12/1999 | Yamato et al. | 430/270.1 |
| 6,261,738 B1 | 7/2001 | Asakura et al. | 430/270.1 |
| 6,673,512 B1 | * 1/2004 | Uenishi et al. | 430/270.1 |
| 6,692,893 B2 | * 2/2004 | Ohsawa et al. | 430/270.1 |
| 2004/0033440 A1 | * 2/2004 | Maeda et al. | 430/270.1 |

FOREIGN PATENT DOCUMENTS

| | | |
|---|---|---|
| JP | 61-251652 A | 11/1986 |
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 11-190904 A | 7/1999 |
| JP | 2000-314956 A | 11/2000 |
| JP | 2000-344836 A | 12/2000 |
| JP | 2001-55373 A | 2/2001 |
| JP | 2001-122850 A | 5/2001 |
| JP | 2001-199955 A | 7/2001 |
| JP | 2001-233842 A | 8/2001 |

OTHER PUBLICATIONS

Wagner et al., Synthetic Organic Chemistry, p. 821–827, John Wiley & Sons (1965).
Arimitsu et al., Journal of Photopolymer Science and Technology, vol. 8, No. 1, 1995, pp. 43–44 & 45–46.
Arimitsu et al., Journal of Photopolymer Science and Technology, vol. 9, No. 1, 1996, pp. 29–30.

* cited by examiner

Primary Examiner—John S. Chu
(74) Attorney, Agent, or Firm—Birch, Stewart, Kolasch & Birch, LLP

(57) ABSTRACT

Photoacid generators are provided by O-arylsulfonyl-oxime compounds having formula (1) wherein R is H, F, Cl, $NO_2$, alkyl or alkoxy, n is 0 or 1, m is 1 or 2, r is 0 to 4, r' is 0 to 5, k is 0 to 4, and G' and G" are S or —CH=CH—. Chemically amplified resist compositions comprising the photoacid generators have many advantages including improved resolution, improved focus latitude, minimized line width variation or shape degradation even on long-term PED, and improved pattern profile after development. Because of high resolution, the compositions are suited for microfabrication, especially by deep UV lithography.

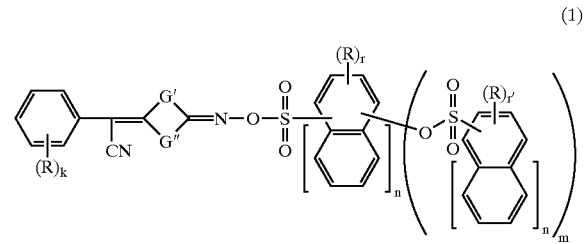

(1)

21 Claims, No Drawings

PHOTOACID GENERATORS, CHEMICALLY AMPLIFIED RESIST COMPOSITIONS, AND PATTERNING PROCESS

This invention relates to photoacid generators for chemically amplified resist compositions, chemically amplified resist compositions comprising the photoacid generators, and a patterning process using the same. The chemically amplified resist compositions are sensitive to such radiation as UV, deep UV, electron beams, x-rays, excimer laser beams, γ-rays, and synchrotron radiation and suitable for the microfabrication of integrated circuits.

BACKGROUND OF THE INVENTION

While a number of efforts are currently being made to achieve a finer pattern rule in the drive for higher integration and operating speeds in LSI devices, deep-ultraviolet lithography is thought to hold particular promise as the next generation in microfabrication technology.

One technology that has attracted a good deal of attention recently utilizes as the deep UV light source a high-intensity KrF excimer laser, especially an ArF excimer laser featuring a shorter wavelength. There is a desire to have a microfabrication technique of finer definition by combining exposure light of shorter wavelength with a resist material having a higher resolution.

In this regard, the recently developed, acid-catalyzed, chemical amplification type resist materials are expected to comply with the deep UV lithography because of their many advantages including high sensitivity, resolution and dry etching resistance. The chemical amplification type resist materials include positive working materials that leave the unexposed areas with the exposed areas removed and negative working materials that leave the exposed areas with the unexposed areas removed.

In chemical amplification type, positive working, resist compositions to be developed with alkaline developers, an alkali-soluble phenol or a resin and/or compound in which carboxylic acid is partially or entirely protected with acid-labile protective groups (acid labile groups) is catalytically decomposed by an acid which is generated upon exposure, to thereby generate the phenol or carboxylic acid in the exposed area which is removed by an alkaline developer. Also, in similar negative working resist compositions, an alkali-soluble phenol or a resin and/or compound having carboxylic acid and a compound (acid crosslinking agent) capable of bonding or crosslinking the resin or compound under the action of an acid are crosslinked with an acid which is generated upon exposure whereby the exposed area is converted to be insoluble in an alkaline developer and the unexposed area is removed by the alkaline developer.

On use of the chemical amplification type, positive working, resist compositions, a resist film is formed by dissolving a resin having acid labile groups as a binder and a compound capable of generating an acid upon exposure to radiation (to be referred to as photoacid generator) in a solvent, applying the resist solution onto a substrate by a variety of methods, and evaporating off the solvent optionally by heating. The resist film is then exposed to radiation, for example, deep UV through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

The chemical amplification type, positive working, resist compositions adapted for KrF excimer lasers generally use a phenolic resin, for example, polyhydroxystyrene in which some or all of the hydrogen atoms of phenolic hydroxyl groups are protected with acid labile protective groups. Iodonium salts, sulfonium salts, bissulfonyldiazomethane compounds, N-sulfonyloxydicarboxyimide compounds and O-arylsulfonyloxime compounds are typically used as the photoacid generator. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

O-arylsulfonyloxime compounds as shown below are advantageously used as the photoacid generator in chemically amplified resist compositions, especially chemically amplified, positive working, resist compositions adapted for KrF excimer lasers because they provide a high sensitivity and resolution and eliminate poor compatibility with resins and poor solubility in resist solvents as found with the sulfonium and iodonium salt photoacid generators. See U.S. Pat. Nos. 6,004,724, 6,261,738, JP-A 9-095479, JP-A 9-208554, JP-A 9-230588, Japanese Patent No. 2,906,999, JP-A 9-301948, JP-A 2000-314956, and JP-A 2001-233842.

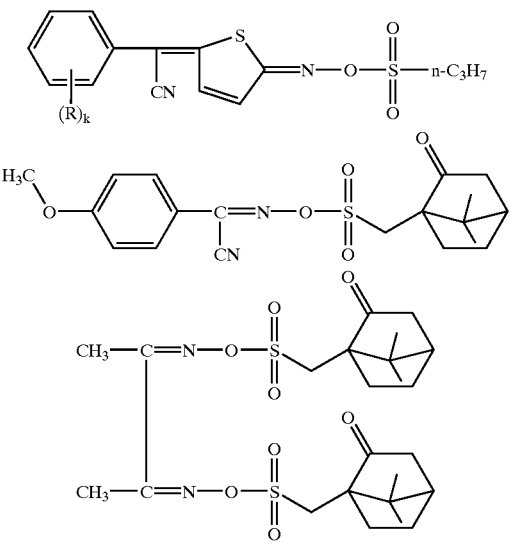

As the requisite pattern size is reduced, however, even the use of these photoacid generators encounters problems including poor resolution and low stability to the environment.

With respect to the resolution, improvements are being made by rendering the acid labile groups in the resin more scissile by acid, using basic additives, or optimizing process conditions.

The environmental stability is generally divided into two categories. One stability problem is that the acid generated upon exposure is deactivated with airborne bases on the resist film or bases on the substrate beneath the resist film. This phenomenon is often found when a photoacid generator capable of generating an acid having a high acid strength is used. There is a probability that this problem will be solved by rendering the acid labile groups in the resin more scissile to acid or by reducing (or weakening) the acid strength of the acid generated. The other problem of environmental stability is that when the duration between exposure and post-exposure bake (PEB) is prolonged, that is, in the case of post exposure delay (PED), the acid generated diffuses through the resist film so that acid deactivation occurs if acid labile groups are less scissile or acid decomposition reaction occurs if acid labile groups are more scissile, often leading to variations of the pattern profile. In chemically amplified positive resist compositions having acid labile groups including primarily acetal groups, for example, the line width of unexposed areas is often narrowed.

As discussed above, for higher resolution, it is necessary to introduce more scissile acid labile groups into a resin, and it is desirable for the photoacid generator to generate a low diffusible acid. As the low diffusible acid, alkylsulfonic acids have been in study. Typical alkylsulfonic acids include 10-camphorsulfonic acid, butanesulfonic acid and octane-sulfonic acid. Since all these alkylsulfonic acids have a weaker acid strength than fluorinated alkylsulfonic acids and arylsulfonic acids commonly employed in the prior art, the amount of acid must compensate for the weakness of acid strength. That is, a more amount of acid must be generated, which in turn, requires to extend the exposure time, often leading to a low productivity.

Under the circumstances, JP-A 2001-122850 describes sulfonium salts and iodonium salts capable of generating tosyloxybenzenesulfonic acid as the acid upon light exposure; and JP-A 2001-55373 describes tosyloxybenzenesulfonyl-diazomethane as a typical example. However, the former has the drawback (pattern sidewall roughening) associated with the use of onium salts and the latter has the drawback of difficult synthesis.

The photoacid generator for resist compositions is required to have a fully high solubility or compatibility in resist solvents and resins, good storage stability, non-toxicity, effective coating, well-defined pattern profile, PED stability, a high resolution, a wide focal depth, and a high sensitivity. Prior art photoacid generators, especially O-arylsulfonyloxime base photoacid generators do not satisfy all these requirements.

In the recent stage when the pattern of integrated circuits becomes more miniaturized, more stringent requirements are imposed on the problems of resolution and focal depth.

SUMMARY OF THE INVENTION

An object of the present invention is to provide a photoacid generator suitable for use in a chemically amplified resist composition such that the resist composition overcomes the above-discussed problems and especially, has an improved pattern profile and focal depth. Another object of the invention is to provide a resist composition comprising the photoacid generator, and a patterning process using the same.

We have found that a resist composition comprising an O-arylsulfonyloxime compound capable of generating an arylsulfonyloxyarylsulfonic acid of the general formula (1'), to be defined below, upon exposure to radiation, especially an O-arylsulfonyloxime compound of the general formula (1), (1a), (1b) or (1c), to be defined below, as a photoacid generator possesses a number of great advantages including dissolution, storage stability, effective coating, minimized line width variation or shape degradation during long-term PED, a well-defined pattern profile after development, a high resolution enough for microfabrication, and a wide focal depth, especially when processed by deep UV lithography.

Particularly when an O-arylsulfonyloxime compound capable of generating a sulfonic acid of the general formula (1'), to be defined below, upon exposure to radiation, especially an O-arylsulfonyloxime compound of the general formula (1) or formula (1a), (1b) or (1c), to be defined below, is used as a photoacid generator in a chemically amplified resist composition comprising a resin which changes its solubility in an alkaline developer under the action of an acid, the above-described advantages are exerted, especially in processing by deep UV lithography.

In a first aspect, the invention provides a photoacid generator for chemically amplified resist compositions, having the following general formula (1).

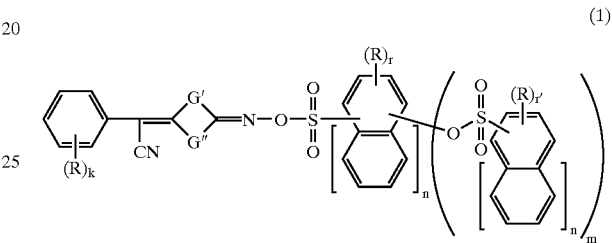

(1)

Herein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5., k is an integer of 0 to 4, and G' and G" each are a sulfur atom or —CH=CH—, excluding the case where both G' and G" are sulfur atoms.

In another embodiment, the invention provides a photoacid generator for chemically amplified resist compositions, having the following general formula (1a).

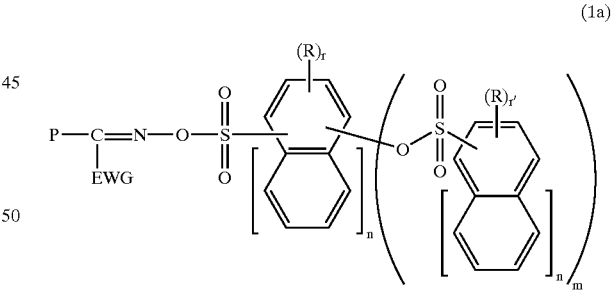

(1a)

Herein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, EWG is a cyano group, nitro group or perfluoroalkyl group of 1 to 3 carbon atoms, and p is a substituted or unsubstituted, straight, branched or cyclic alkyl group of 1 to 10 carbon atoms or substituted or unsubstituted aryl group of 6 to 12 carbon atoms.

In a further embodiment, the invention provides a photoacid generator for chemically amplified resist compositions, having the following general formula (1b).

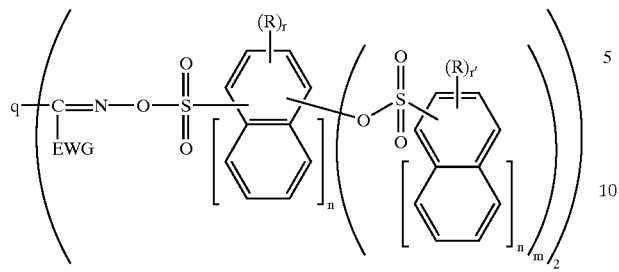

(1b)

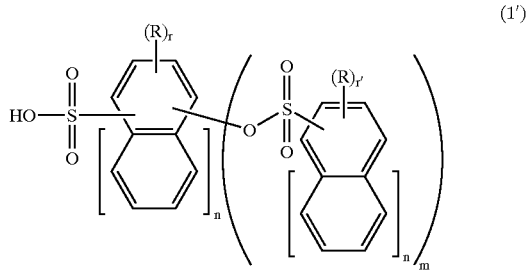

(1')

Herein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, EWG is a cyano group, nitro group or perfluoroalkyl group of 1 to 3 carbon atoms, and q is a substituted or unsubstituted, straight, branched or cyclic alkylene group of 1 to 10 carbon atoms or substituted or unsubstituted arylene group of 6 to 18 carbon atoms.

In a still further embodiment, the invention provides a photoacid generator for chemically amplified resist compositions, having the following general formula (1c).

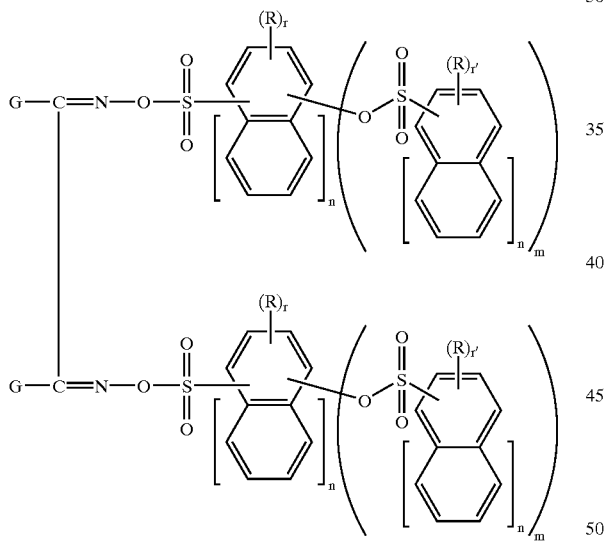

(1c)

Herein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, and G is a hydrogen atom, substituted or unsubstituted, straight, branched or cyclic alkyl group of 1 to 10 carbon atoms or substituted or unsubstituted aryl group of 6 to 12 carbon atoms, or two G's taken together may form a cyclic structure with the carbon atoms to which the G's are attached.

In a second aspect, the invention provides a photoacid generator in the form of an O-arylsulfonyloxime compound for chemically amplified resist compositions, capable of generating an arylsulfonyloxyarylsulfonic acid having the following general formula (1') upon exposure to ultraviolet radiation, deep ultraviolet radiation, electron beams, x-rays, excimer laser beams, gamma-rays or synchrotron radiation.

Herein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, and r' is an integer of 0 to 5.

In a third aspect, the invention provides a chemically amplified resist composition, preferably a chemically amplified positive resist composition, comprising (A) a resin which changes its solubility in an alkaline developer under the action of an acid, and (B) the photoacid generator defined above.

The resist composition may further include (C) a compound capable of generating an acid upon exposure to radiation, other than component (B).

In one preferred embodiment, the resin (A) has such substituent groups having C—O—C linkages that the solubility in an alkaline developer changes as a result of scission of the C—O—C linkages under the action of an acid.

In another preferred embodiment, the resin (A) is a polymer containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl groups, the polymer having a weight average molecular weight of 3,000 to 100,000.

In a further preferred embodiment, the resin (A) is a polymer comprising recurring units of the following general formula (2a):

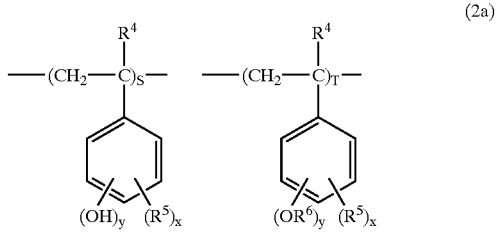

(2a)

wherein $R^4$ is hydrogen or methyl, $R^5$ is a straight, branched or cyclic alkyl group of 1 to 8 carbon atoms, x is 0 or a positive integer, y is a positive integer, satisfying $x+y \leq 5$, $R^6$ is an acid labile group, S and T are positive integers, satisfying $0<T/(S+T) \leq 0.8$, wherein the polymer contains units in which hydrogen atoms of phenolic hydroxyl groups are partially substituted with acid labile groups of one or more types, a proportion of the acid labile group-bearing units is on the average from more than 0 mol % to 80 mol % based on the entire polymer, and the polymer has a weight average molecular weight of 3,000 to 100,000.

In a further preferred embodiment, the resin (A) is a polymer comprising recurring units of the following general formula (2a'):

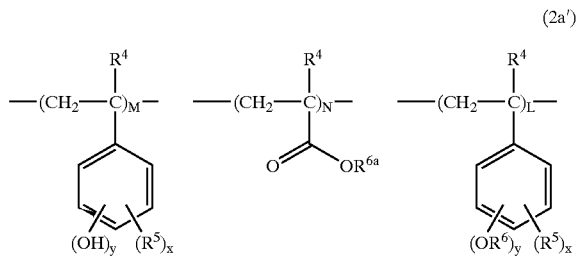
(2a')

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, at least some of $R^{6a}$ being acid labile groups, x is 0 or a positive integer, y is a positive integer, satisfying x+y≤5, M and N are positive integers, L is 0 or a positive integer, satisfying 0<N/(M+N+L)≤0.5 and 0<(N+L)/(M+N+L)≤0.8, wherein the polymer contains on the average from more than 0 mol % to 50 mol % of those units based on acrylate and methacrylate, and also contains on the average from more than 0 mol % to 80 mol % of acid labile group-bearing units, based on the entire polymer, and the polymer has a weight average molecular weight of 3,000 to 100,000.

In a further preferred embodiment, the resin (A) is a polymer comprising recurring units of the following general formula (2a"):

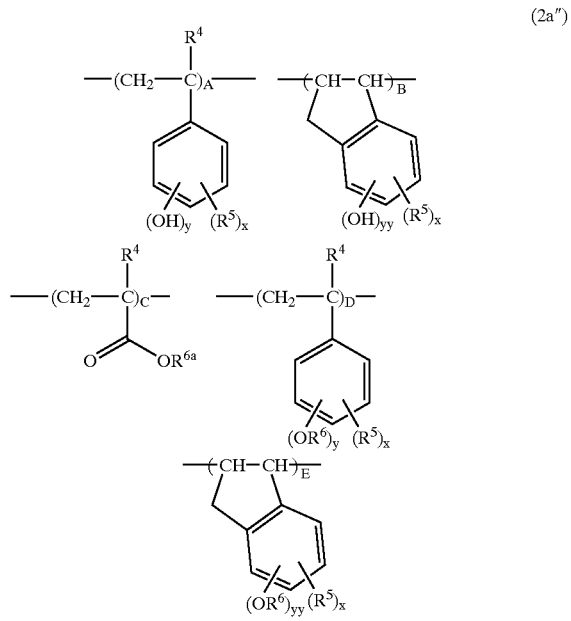
(2a")

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, at least some of $R^{6a}$ being acid labile groups, x is 0 or a positive integer, y is a positive integer, satisfying x+y≤5, yy is 0 or a positive integer, satisfying x+yy≤4, A and B are positive integers, C, D and E each are 0 or a positive integer, satisfying 0<(B+E)/(A+B+C+D+E)≤0.5 and 0<(C+D+E)/(A+B+C+D+E)≤0.8, wherein the polymer contains on the average from more than 0 mol % to 50 mol % of those units based on indene and/or substituted indene, and also contains on the average from more than 0 mol % to 80 mol % of acid labile group-bearing units, based on the entire polymer, and the polymer has a weight average molecular weight of 3,000 to 100,000.

In the foregoing preferred embodiments, the acid labile group is preferably selected from the class consisting of groups of the following general formulae (4) to (7), tertiary alkyl groups of 4 to 20 carbon atoms, trialkylsilyl groups whose alkyl moieties each have 1 to 6 carbon atoms, oxoalkyl groups of 4 to 20 carbon atoms, and aryl-substituted alkyl groups of 7 to 20 carbon atoms.

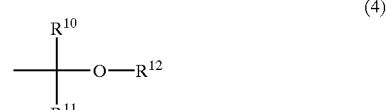
(4)

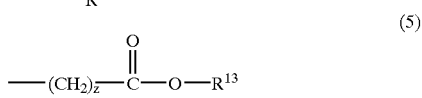
(5)

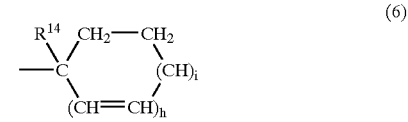
(6)

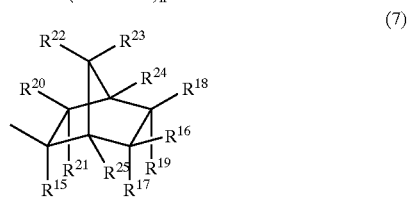
(7)

Herein $R^{10}$ and $R^{11}$ each are hydrogen or a straight, branched or cyclic alkyl group having 1 to 18 carbon atoms, and $R^{12}$ is a monovalent hydrocarbon group of 1 to 18 carbon atoms which may contain a heteroatom, a pair of $R^{10}$ and $R^{11}$, $R^{10}$, and $R^{12}$, or $R^{11}$ and $R^{12}$ may together form a ring, with the proviso that $R^{10}$, $R^{11}$, and $R^{12}$ each are a straight or branched alkylene of 1 to 18 carbon atoms when they form a ring; $R^{13}$ is a tertiary alkyl group of 4 to 20 carbon atoms, a group whose alkyl moieties each have 1 to 6 carbon atoms, an oxoalkyl group of 4 to 20 carbon atoms, or a group of the formula (4), z is an integer of 0 to 6; $R^{14}$ is a straight, branched or cyclic alkyl group of 1 to 8 carbon atoms or an aryl group of 6 to 20 carbon atoms which may be substituted, h is 0 or 1, i is 0, 1, 2 or 3, satisfying 2h+i=2 or 3; $R^{15}$ is a straight, branched or cyclic alkyl group of 1 to 8 carbon atoms or an aryl group of 6 to 20 carbon atoms which may be substituted, $R^{16}$ to $R^{25}$ are each independently hydrogen or a monovalent hydrocarbon group of 1 to 15 carbon atoms which may contain a heteroatom, $R^{16}$ to $R^{25}$, taken together, may form a ring, each of $R^{16}$ to $R^{25}$ is a divalent hydrocarbon group of 1 to 15 carbon atoms which may contain a heteroatom when they form a ring, or two of $R^{16}$ to $R^{25}$ which attached to adjoining carbon atoms may bond together directly to form a double bond.

The resist composition may further include (D) a basic compound and/or (E) an organic acid derivative.

The resist composition may further include an organic solvent which contains a propylene glycol alkyl ether acetate, an alkyl lactate or a mixture thereof.

In a fourth aspect, the invention provides a process for forming a pattern, comprising the steps of applying the resist composition defined above onto a substrate to form a coating; heat treating the coating and exposing the coating to high energy radiation with a wavelength of up to 300 nm or electron beam through a photomask; optionally heat treating the exposed coating, and developing the coating with a developer.

DESCRIPTION OF THE PREFERRED EMBODIMENTS

Photoacid Generator

In the first aspect, the present invention provides a photoacid generator having an arylsulfonyloxyarylsulfonyl group for use in chemically amplified resist compositions, represented by the general formula (1) or formula (1a), (1b) or (1c).

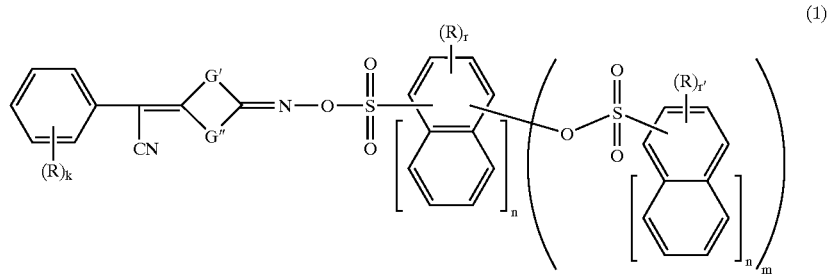

(1)

R, n, m, r, r', k, G' and G" are as defined above.

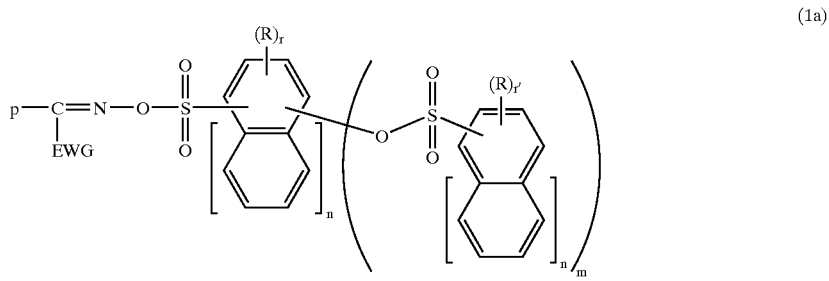

(1a)

R, n, m, r, r', EWG and p are as defined above.

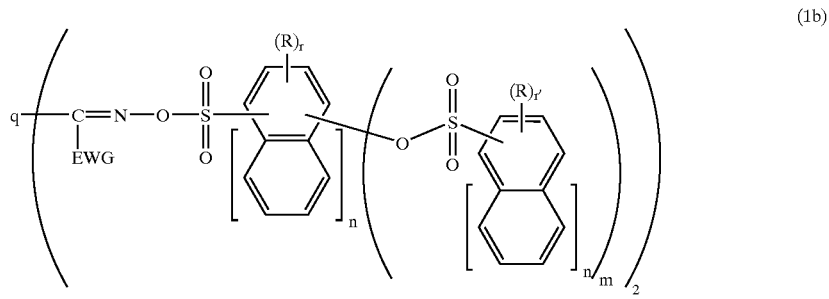

(1b)

R, n, m, r, r', EWG and q are as defined above.

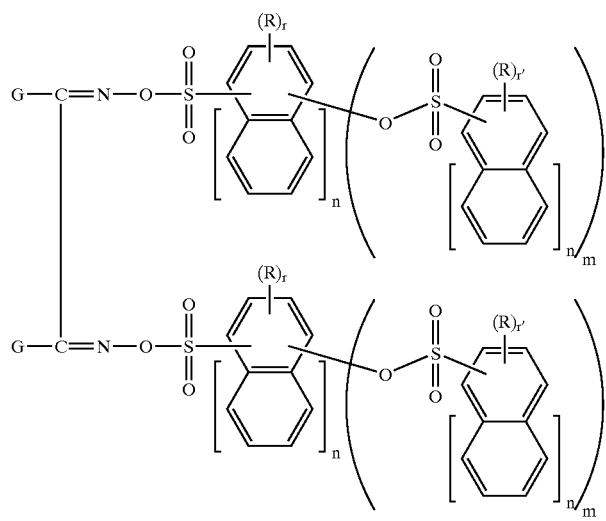

R, n, m, r, r', and G are as defined above.

Referring to formula (1) or formula (1a), (1b) or (1c), R which may be the same or different is a hydrogen atom, a fluorine atom, a chlorine atom, a nitro group, or a substituted or unsubstituted, straight, branched or cyclic alkyl or alkoxy group of 1 to 12 carbon atoms, for example, hydrogen, methyl, ethyl, n-propyl, sec-propyl, cyclopropyl, n-butyl, sec-butyl, iso-butyl, tert-butyl, methoxy, ethoxy, n-propyloxy, sec-propyloxy, n-butyloxy, sec-butyloxy, iso-butyloxy, tert-butyloxy, n-hexyl, n-hexyloxy, n-octyl, n-octyloxy, n-decyl, n-decyloxy, n-dodecyl, and n-dodecyloxy groups. Of these, hydrogen, methyl, ethyl, n-hexyloxy and n-octyloxy groups are preferred, with hydrogen and methyl being more preferred. The subscript n is 0 or 1, m is 1 or 2, r is an integer of 0 to 4, and r' is an integer of 0 to 5. The arylsulfonyoxy group(s) may substitute on the arylsulfonyl group at any desired position, that is, the substitution position is not critical. The preferred substitution position is the 4-position when the arylsulfonyl group is a benzenesulfonyl group. When the arylsulfonyl group is a naphthalenesulfonyl group, the preferred substitution position differs between 1-naphthalenesulfonyl and 2-naphthalenesulfonyl groups. For the 1-naphthalenesulfonyl group, the 4-, 5- or 8-position is preferred, and for the 2-naphthalenesulfonyl group, the 6-position is preferred.

Illustrative, non-limiting examples of the (arylsulfonyloxy)arylsulfonyloxy group include
4-(4'-toluenesulfonyloxy)benzenesulfonyloxy,
4-(benzenesulfonyloxy)benzenesulfonyloxy,
4-(4'-methoxybenzenesulfonyloxy)benzenesulfonyloxy,
4-(4'-fluorobenzenesulfonyloxy)benzenesulfonyloxy,
4-(4'-trifluoromethylbenzenesulfonyloxy)benzenesulfonyloxy,
4-(pentafluorobenzenesulfonyloxy)benzenesulfonyloxy,
4-(2-naphthalenesulfonyloxy)benzenesulfonyloxy,
3-methoxy-4-(4'-toluenesulfonyloxy)benzenesulfonyloxy,
3-methyl-4-(4'-toluenesulfonyloxy)benzenesulfonyloxy,
2-(4'-toluenesulfonyloxy)naphthalene-6-sulfonyloxy,
1-(4'-toluenesulfonyloxy)naphthalene-4-sulfonyloxy,
1-(4'-toluenesulfonyloxy)naphthalene-8-sulfonyloxy,
2,5-bis(4'-toluenesulfonyloxy)benzenesulfonyloxy, and 2,5-bis(4'-methoxyenesulfonyloxy)benzenesulfonyloxy.

In the O-arylsulfonyloxime compounds of formulae (1), (1a), (1b) and (1c), the oxime skeleton is not critical and may be an oxime structure as found in well-known O-alkylsulfonyloxime compounds and O-arylsulfonyloxime compounds. Especially preferred are oxime structures in the compounds described in the above-referred patents, U.S. Pat. Nos. 6,004,724, 6,261,738, JP-A 9-95479, JP-A 9-208554, JP-A 9-230588, Japanese Patent No. 2,906,999, JP-A 9-301948, JP-A 2000-314956 and JP-A 2001-233842.

Especially desired are oxime compounds which are obtained by reacting substituted phenylacetonitrile compounds with 2-nitrothiophene or nitrobenzene in an alcohol solvent under basic conditions as described in Yamato et al., U.S. Pat. No. 6,004,724.

For the oxime compound obtained using 2-nitrothiophene, geometric isomers exist although the compound identified on analysis by nuclear magnetic resonance spectroscopy is a single compound.

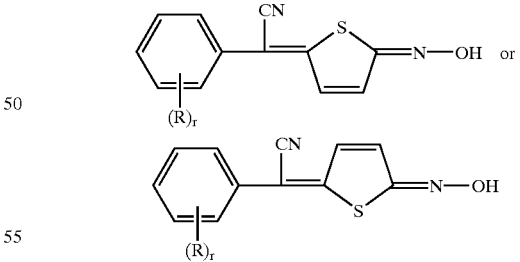

Although the structure has not been specified, the oxime compound synthesized according to the above-described formulation is desirably used as the starting material in the following process.

In the oxime skeleton of formula (1), R has the same meaning as above. The substitution position of R is not critical although the possession of methyl at the 2-position on the phenyl group is preferred.

In formula (1a), EWG is a cyano group, a nitro group or a perfluoroalkyl group of 1 to 3 carbon atoms such as trifluoromethyl, perfluoroethyl or perfluoro-n-propyl. Of these, cyano and trifluoromethyl groups are preferred.

The symbol "p" is a substituted or unsubstituted, straight, branched or cyclic alkyl group of 1 to 10 carbon atoms or a substituted or unsubstituted aryl group of 6 to 12 carbon atoms, for example, cyclopentyl, cyclohexyl, phenyl, 4-methoxyphenyl, 3,4-dimethoxyphenyl, 4-methylthiophenyl, 2-methylphenyl, 4-methylphenyl and 4-phenoxoxyphenyl groups. Of these, phenyl, 4-methoxyphenyl, 2-methylphenyl, 4-methylphenyl and 4-phenoxoxyphenyl groups are preferred.

In formula (1b), EWG is as defined for formula (1a); the symbol "q" is a substituted or unsubstituted, straight, branched or cyclic alkylene group of 1 to 10 carbon atoms or a substituted or unsubstituted arylene group of 6 to 18 carbon atoms, for example, 1,4-phenylene, 1,3-phenylene, and groups of the formulae shown below.

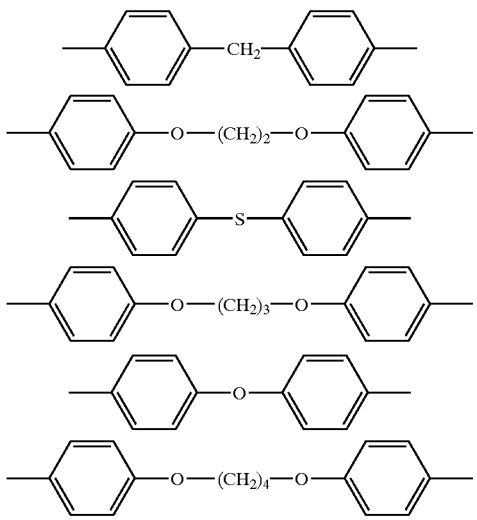

In formula (1c), G is a hydrogen atom, a substituted or unsubstituted, straight, branched or cyclic alkyl group of 1 to 10 carbon atoms or a substituted or unsubstituted aryl group of 6 to 12 carbon atoms. Alternatively, two G's taken together may form a cyclic structure with the carbon atoms to which the G's are attached, the cyclic structure being preferably a 4 to 10-membered, especially 6-membered ring. Examples include hydrogen, methyl, ethyl, n-propyl, n-butyl, phenyl, 4-methylphenyl, 4-methoxyphenyl, and 1,2-cyclohexylene. Of these, methyl is most preferred.

In the second aspect, the present invention provides a photoacid generator in the form of an O-arylsulfonyloxime compound for chemically amplified resist compositions, capable of generating an arylsulfonyloxyarylsulfonic acid having the general formula (1'), shown below, upon exposure to ultraviolet radiation, deep ultraviolet radiation, electron beams, x-rays, excimer laser beams, gamma-rays or synchrotron radiation.

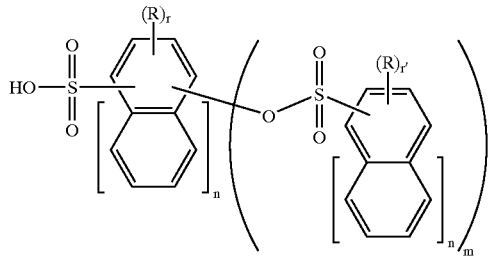

Herein R, n, m, r and r' are as defined above.

The O-sulfonyloxime compound capable of generating a sulfonic acid of formula (1') may have an oxime structure as found in well-known O-alkylsulfonyloxime compounds and O-arylsulfonyloxime compounds though the oxime structure is not limited thereto. Especially preferred are oxime structures in the compounds described in the above-referred patents, U.S. Pat. Nos. 6,004,724, 6,261,738, JP-A 9-95479, JP-A 9-208554, JP-A 9-230588, Japanese Patent No. 2,906, 999, JP-A 9-301948, JP-A 2000-314956 and JP-A 2001-233842.

Illustrative, non-limiting examples of the arylsulfonyloxyarylsulfonic acid that the photoacid generator of the invention generates upon light exposure include (arylsulfonyloxy)arylsulfonic acids, such as 4-(4'-toluenesulfonyloxy)benzenesulfonic acid,
4-(benzenesulfonyloxy)benzenesulfonic acid,
4-(4'-methoxybenzenesulfonyloxy)benzenesulfonic acid,
4-(4'-fluorobenzenesulfonyloxy)benzenesulfonic acid,
4-(4'-trifluoromethylbenzenesulfonyloxy)benzenesulfonic acid,
4-(pentafluorobenzenesulfonyloxy)benzenesulfonic acid,
4-(2-naphthalenesulfonyloxy)benzenesulfonic acid,
3-methoxy-4-(4'-toluenesulfonyloxy)benzenesulfonic acid,
3-methyl-4-(4'-toluenesulfonyloxy)benzenesulfonic acid,
2-(4'-toluenesulfonyloxy)naphthalene-6-sulfonic acid,
1-(4'-toluenesulfonyloxy)naphthalene-4-sulfonic acid,
1-(4'-toluenesulfonyloxy)naphthalene-8-sulfonic acid,
2,5-bis(4'-toluenesulfonyloxy)benzenesulfonic acid, and
2,5-bis(4'-methoxybenzenesulfonyloxy)benzenesulfonic acid.

It is understood that the process for synthesizing the O-arylsulfonyloxime compounds is as described below, but not limited thereto.

The (arylsulfonyloxy)arylsulfonic acids can be synthesized in accordance with the above-referred JP-A 2001-122850. Illustratively, hydroxyarylsulfonic acids or hydroxyarylsulfonic acid salts are reacted with arylsulfonyl halides or arylsulfonic acid anhydrides in the presence of bases such as sodium hydroxide and potassium hydroxide, to form sodium (arylsulfonyloxy)arylsulfonates.

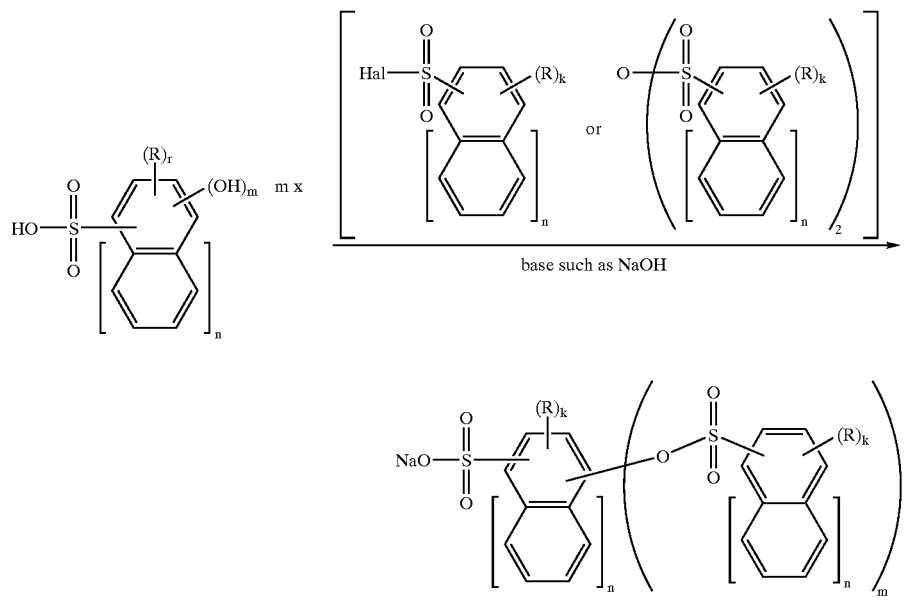

Herein, R, m, n, and k are as defined above, and Hal stands for a bromine or chlorine atom.

More illustratively, suitable hydroxyarylsulfonic acids include, but are not limited to, 4-phenolsulfonic acid, 3-methyl-4-phenolsulfonic acid, 3-methoxy-4-phenolsulfonic acid, 3-nitro-4-phenolsulfonic acid, hydroquinone-2-sulfonic acid, 1,4-naphtholsulfonic acid, 1,5-naphtholsulfonic acid, 2,6-naphtholsulfonic acid, 1,8-naphtholsulfonic acid, 6,7-dihydroxy-2-naphthalenesulfonic acid, and 5,7-dinitro-8-hydroxy-2-naphthalenesulfonic acid. Suitable arylsulfonyl halides include, but are not limited to, benzenesulfonyl chloride, 4-toluenesulfonyl chloride, 4-ethylbenzenesulfonyl chloride, 4-methoxybenzenesulfonyl chloride, 4-fluorobenzene-sulfonyl chloride, 4-trifluoromethylbenzenesulfonyl chloride, 2,4,6-trimethylbenzenesulfonyl chloride, pentafluorobenzenesulfonyl chloride, and 2-naphthalenesulfonyl chloride.

The resulting sulfonic acids or sulfonic acid salts are converted into sulfonyl halides using phosphorus pentachloride, thionyl chloride or the like. With respect to the synthesis of sulfonyl chlorides from sulfonic acid salts, reference is made to JP-A 2001-199955, JP-A 61-251652, Wagner, Zook et al., Synthetic Organic Chemistry, page 821,

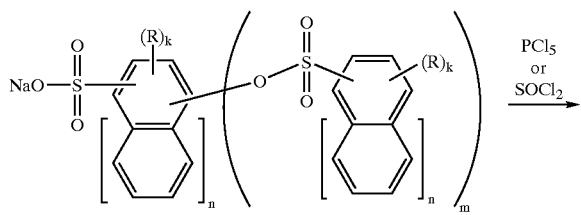

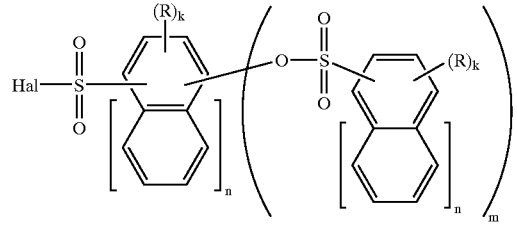

Herein, R, m, n, and k are as defined above, and Hal stands for a bromine or chlorine atom.

The oxime compounds used herein may be commercially available products or compounds synthesized as described in the above-referred patents, U.S. Pat. Nos. 6,004,724, 6,261,738, JP-A 9-95479, JP-A 9-208554, JP-A 9-230588, Japanese Patent No. 2,906,999, JP-A 9-301948, JP-A 2000-314956 and JP-A 2001-233842.

The target O-sulfonyloxime compounds are advantageously produced by dissolving the sulfonyl halides or sulfonic acid anhydrides thereof corresponding to the oxime compounds in a suitable solvent such as THF or $CH_2Cl_2$ and effecting reaction under basic conditions. Alternatively, reaction is preferably effected in basic solvents such as pyridine.

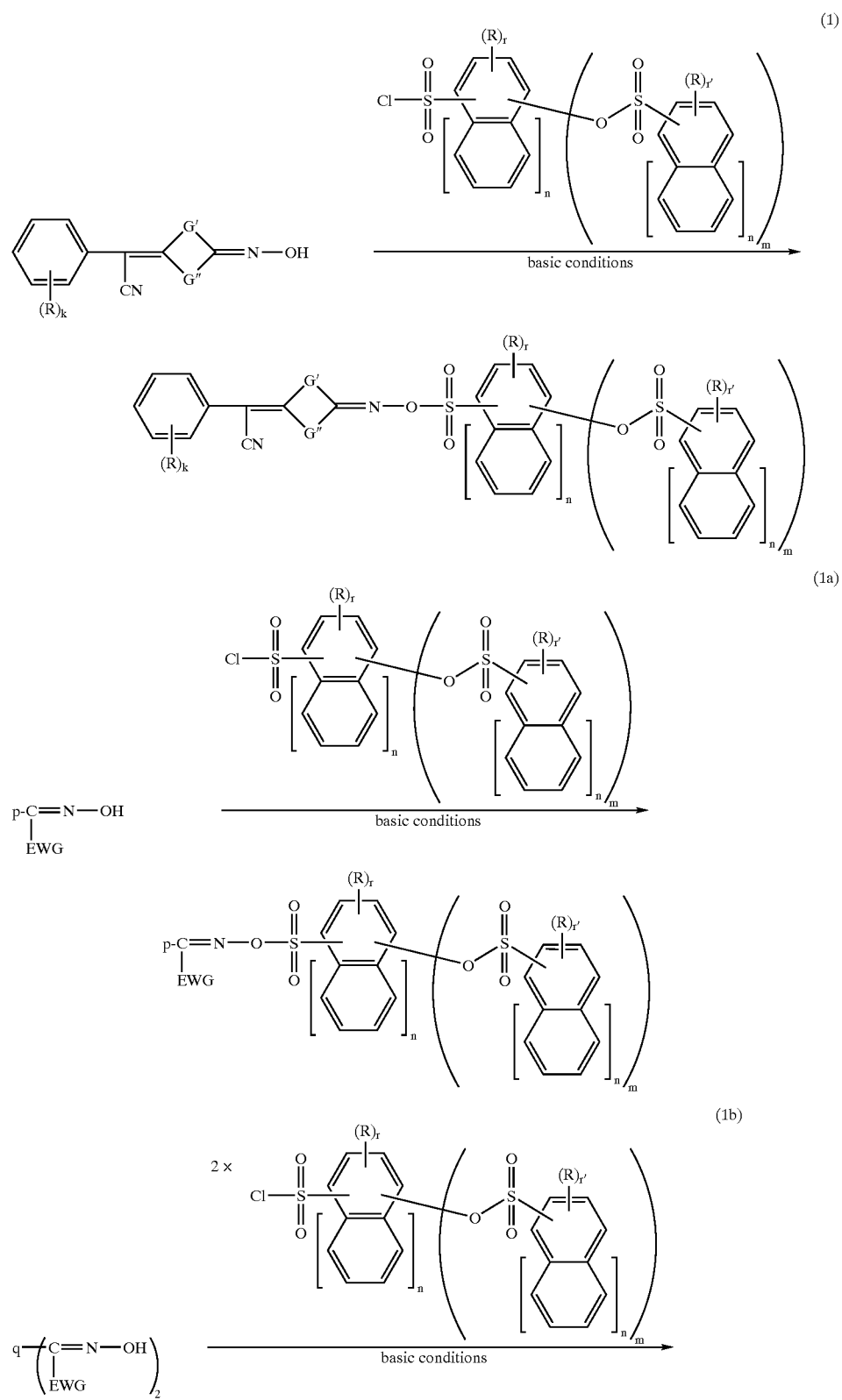

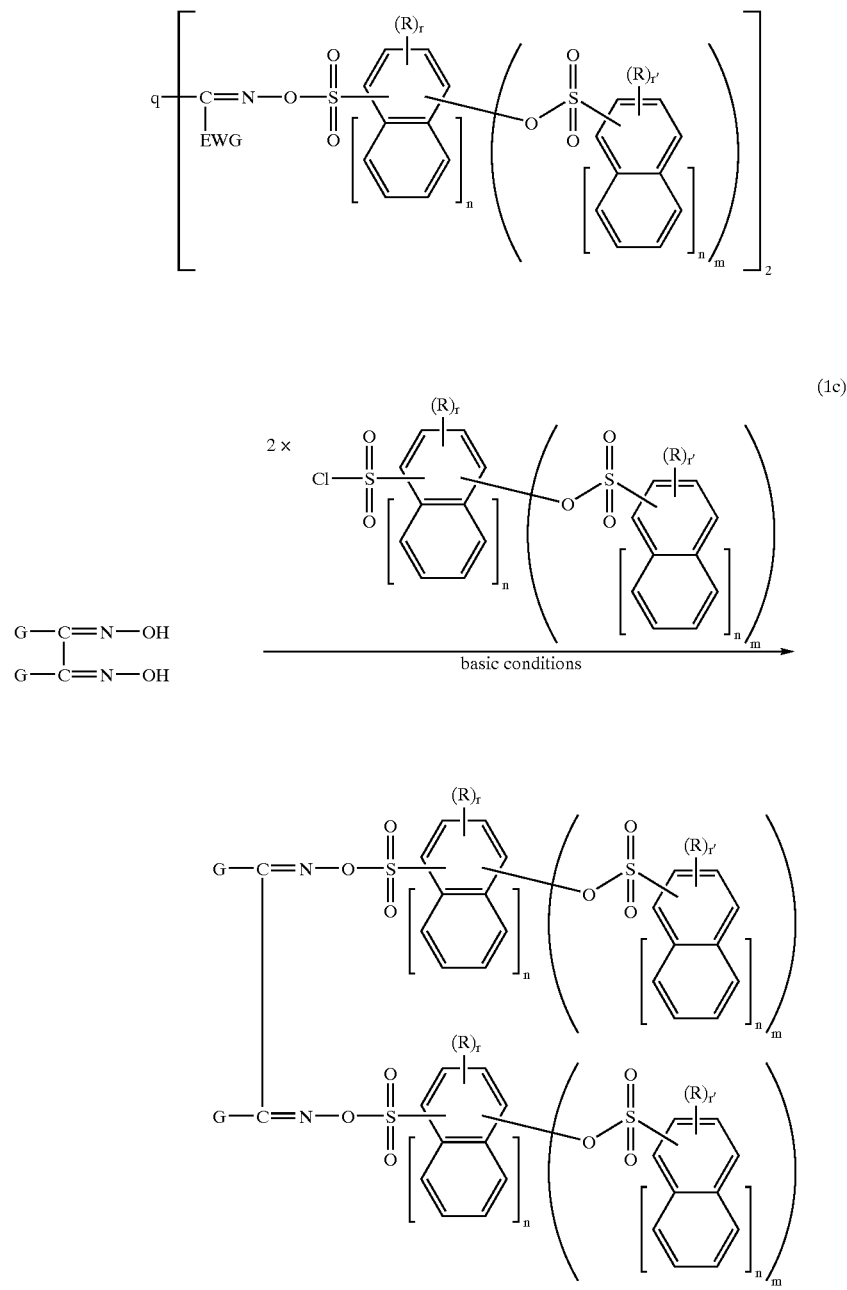

(1c)

Herein, R, r, r', k, m, n, p, q, EWG, G, G' and G" are as defined above.

While the substituents on the O-arylsulfonyloxime compounds having the formulae (1), (1a), (1b) and (1c) according to the invention is as defined above, preferred examples of the compounds are described below.

The O-arylsulfonyloxime compounds of formula (1) according to the invention can be represented in a divided form as comprising an oxime moiety and an arylsulfonyloxy-arylsulfonyl group as shown below.

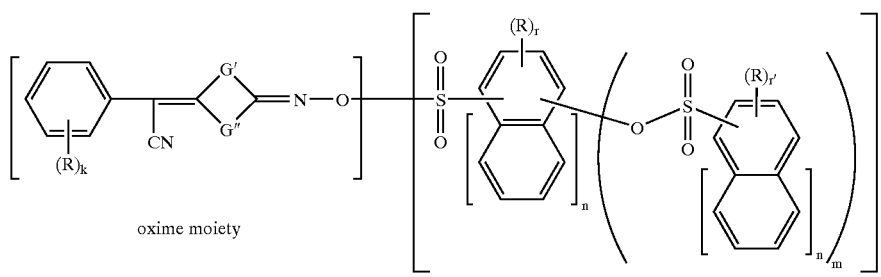
oxime moiety — arylsulfonyloxyarylsulfonyl group
Illustrative examples of the oxime moiety are given below.
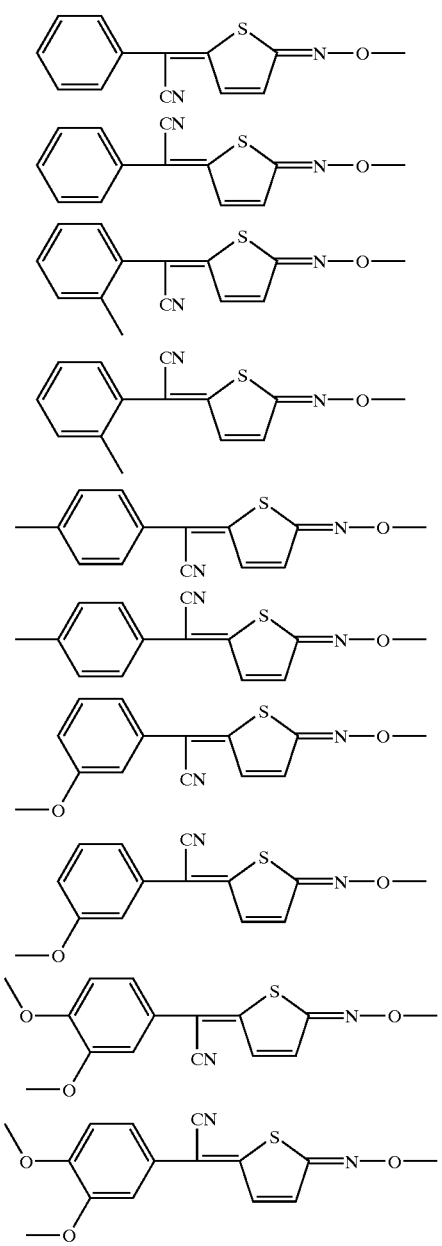
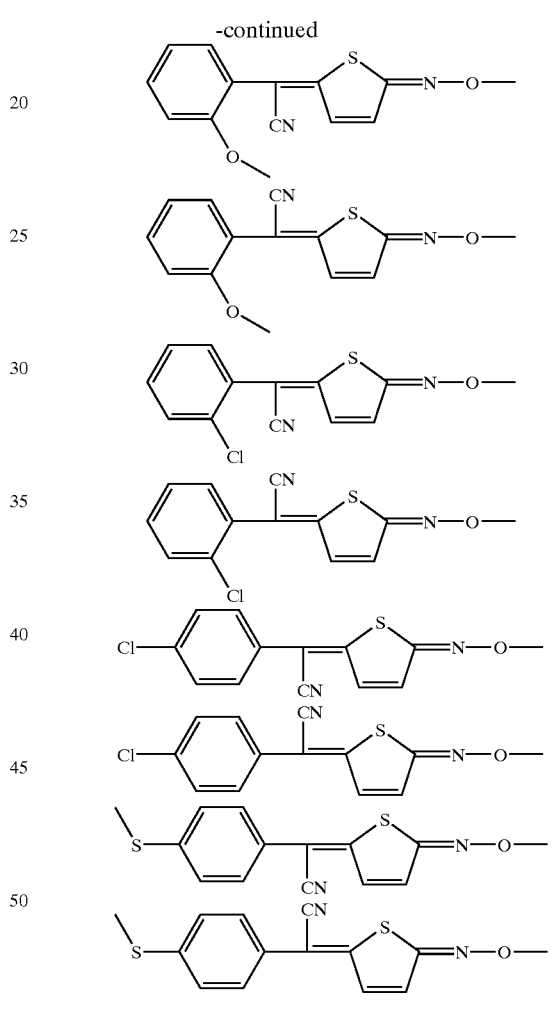
The sulfonyl group is as previously described, and illustrative examples thereof are given below.
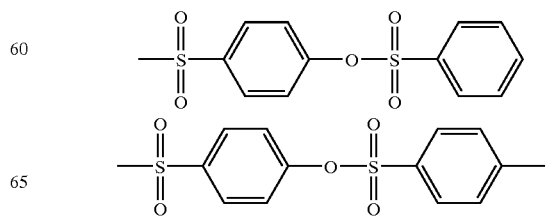

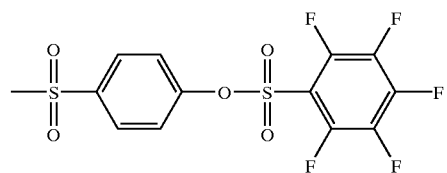
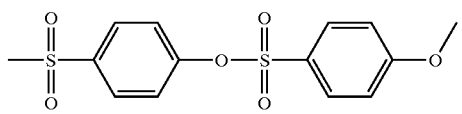
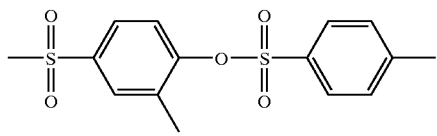
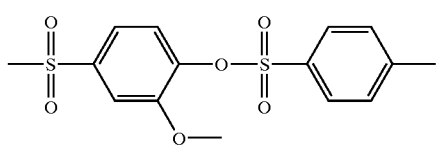
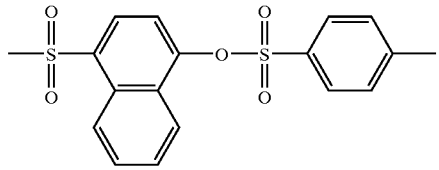
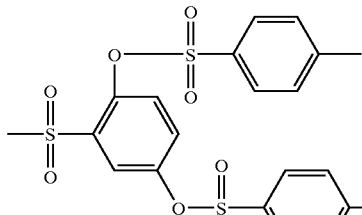
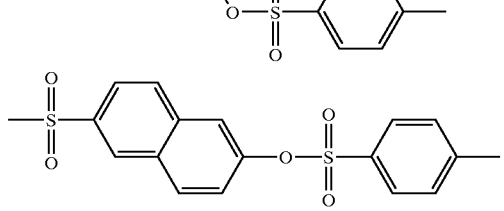
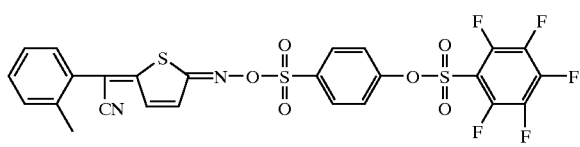
The combination of oxime moiety with sulfonyl group is arbitrary.
Examples of the arylsulfonyloxime compounds of formula (1) in a more preferred embodiment of the invention are given below.
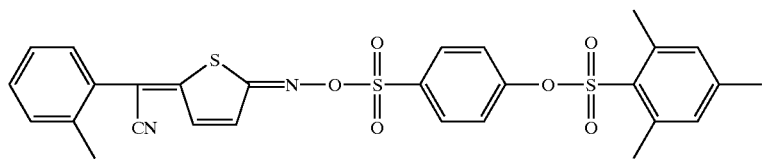
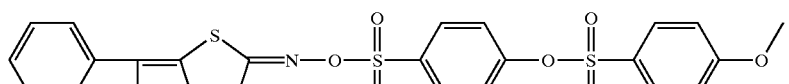
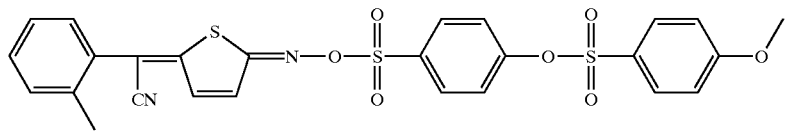
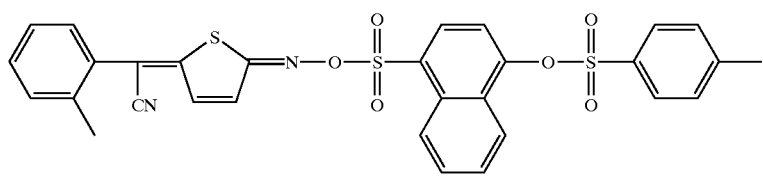
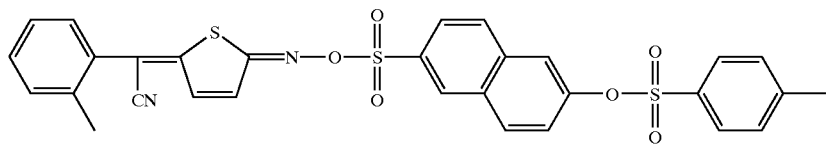
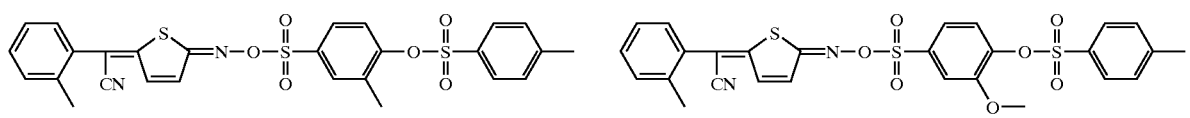

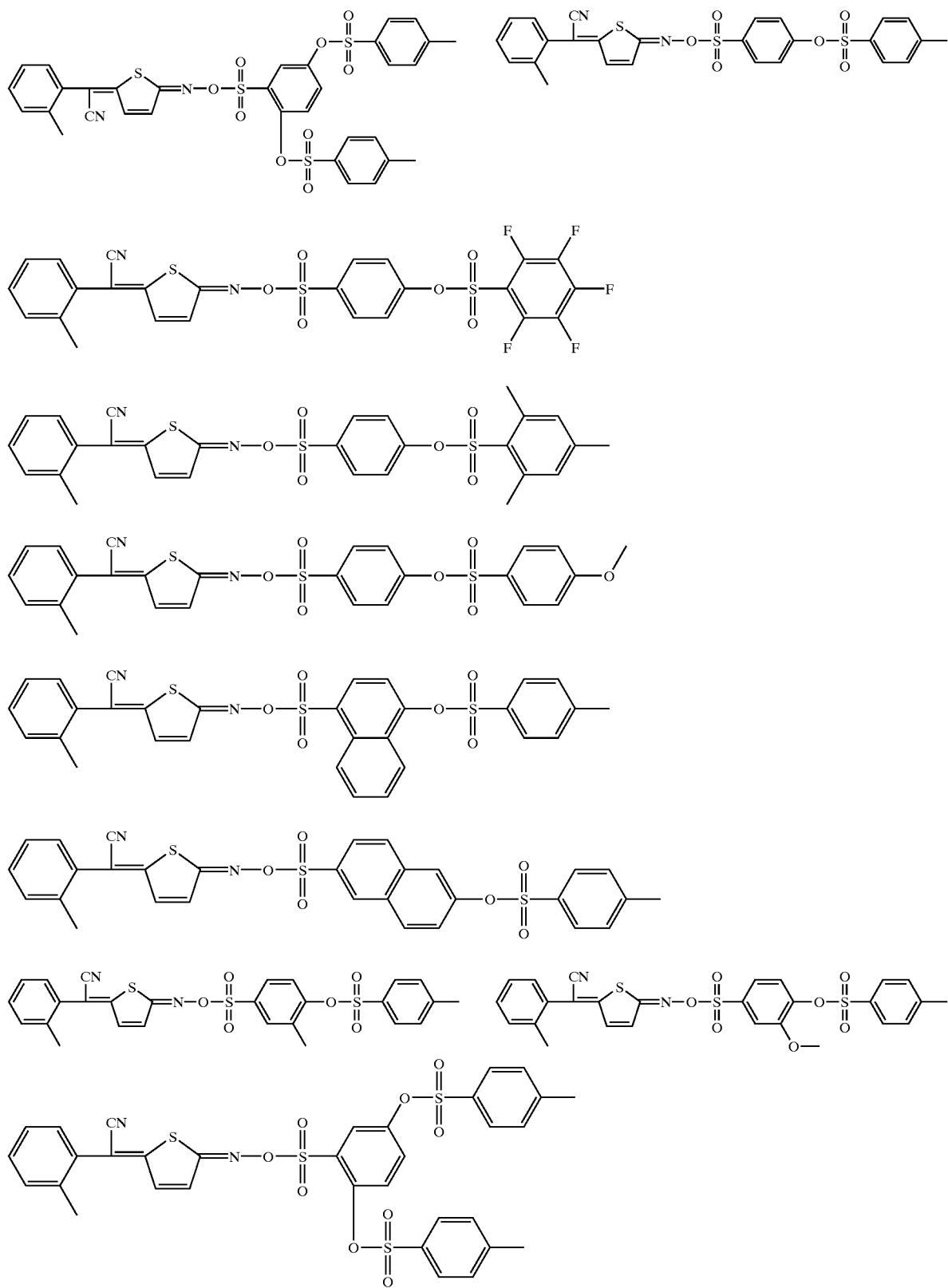
The O-arylsulfonyloxime compounds of formula (1a) according to the invention can be represented in a divided form as comprising an oxime moiety and an arylsulfonyloxy-arylsulfonyl group as shown below.

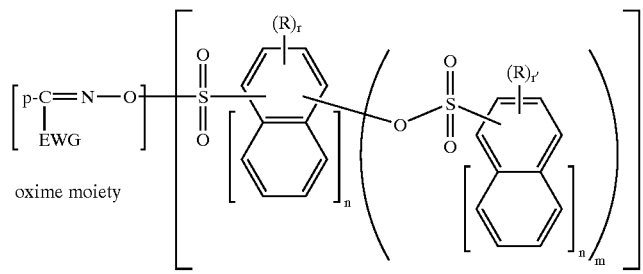
arylsulfonyloxyarylsulfonyl group
Illustrative examples of the oxime moiety are given below.
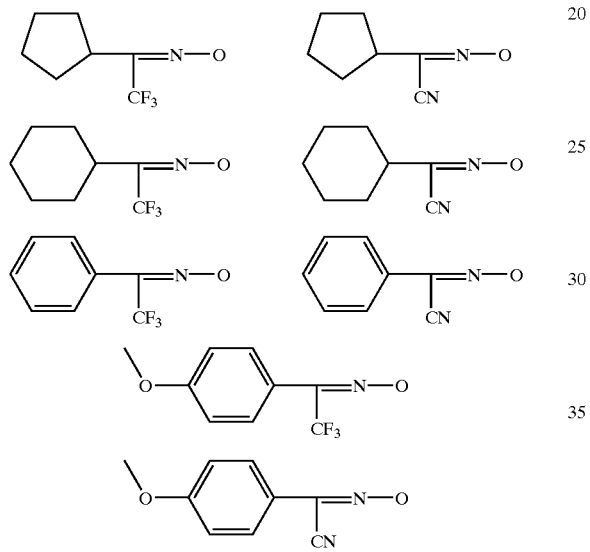
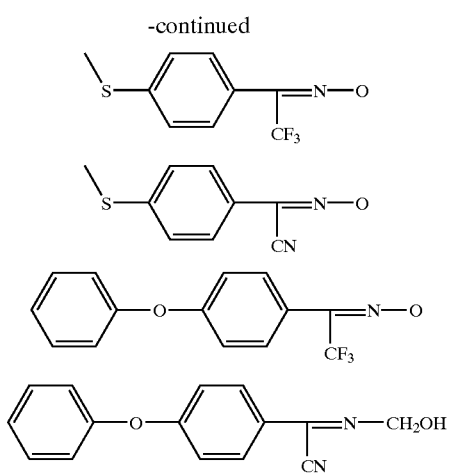
Examples of the sulfonyl group are as described for formula (1), and the combination of oxime moiety with sulfonyl group is arbitrary.
Preferred examples of the arylsulfonyloxime compounds of formula (1a) are given below.
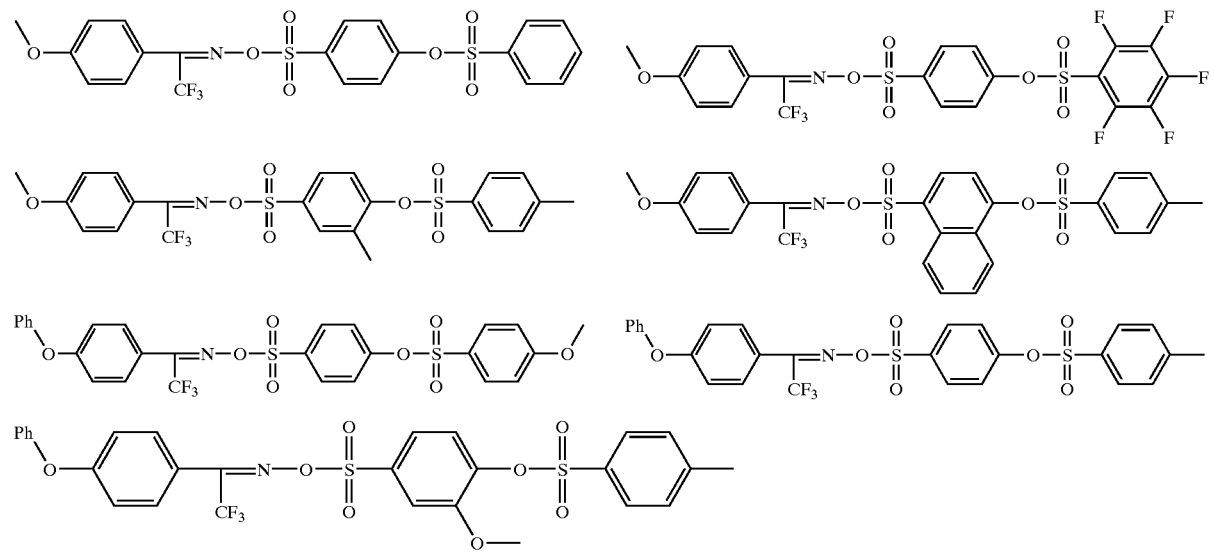

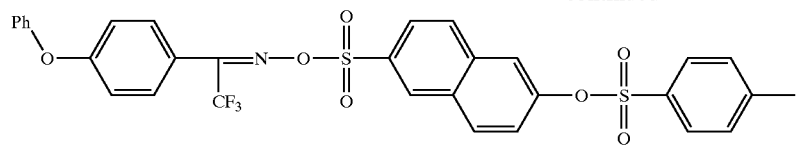
The O-arylsulfonyloxime compounds of formula (1b) according to the invention can be represented in a divided form as comprising an oxime moiety and an arylsulfonyloxy-arylsulfonyl group as shown below.
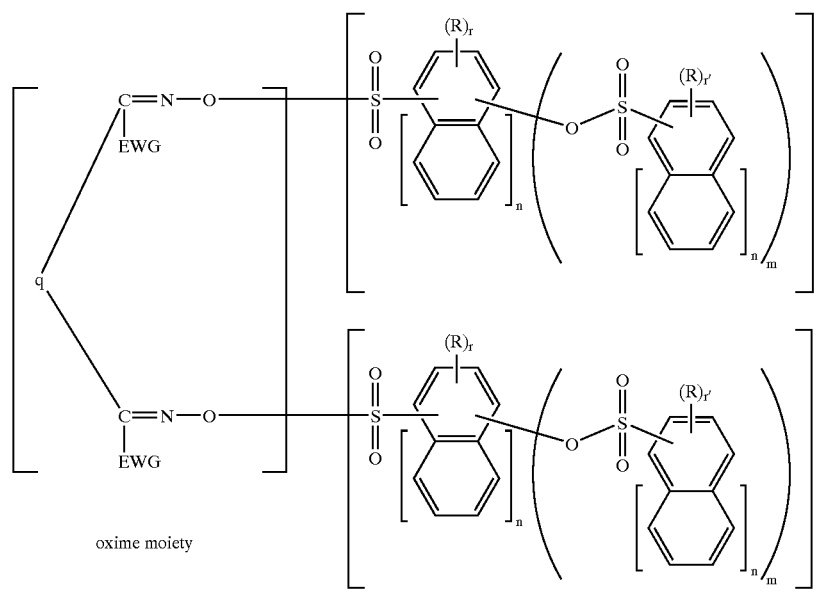
Illustrative examples of the oxime moiety are given below.
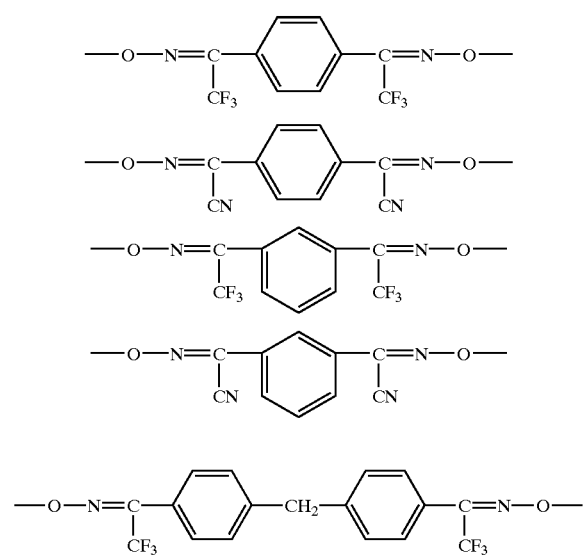
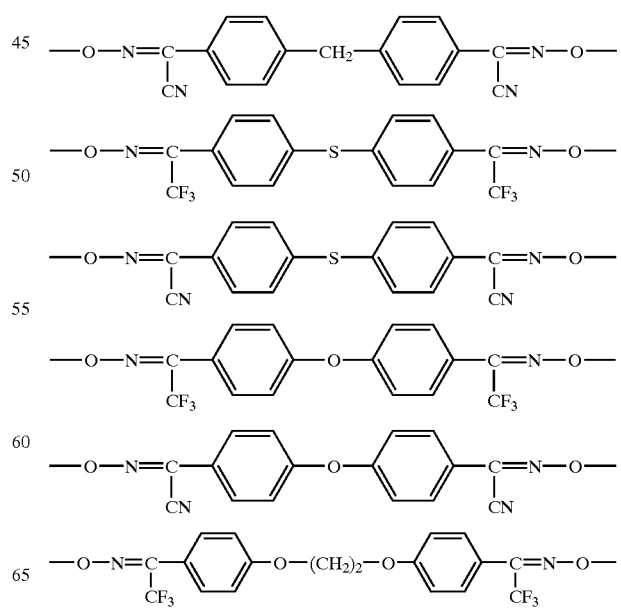

31
-continued
32
-continued
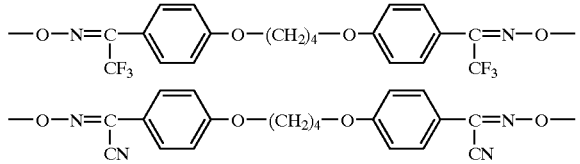
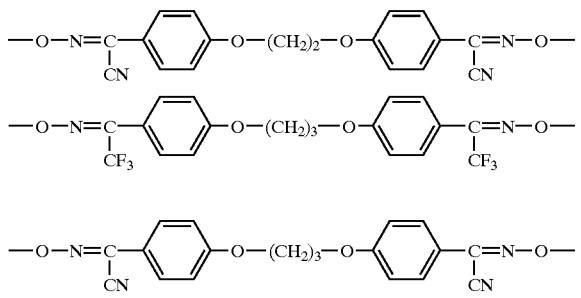
Examples of the sulfonyl group are as described for formula (1), and the combination of oxime moiety with sulfonyl group is arbitrary.
Preferred examples of the arylsulfonyloxime compounds of formula (1b) are given below.
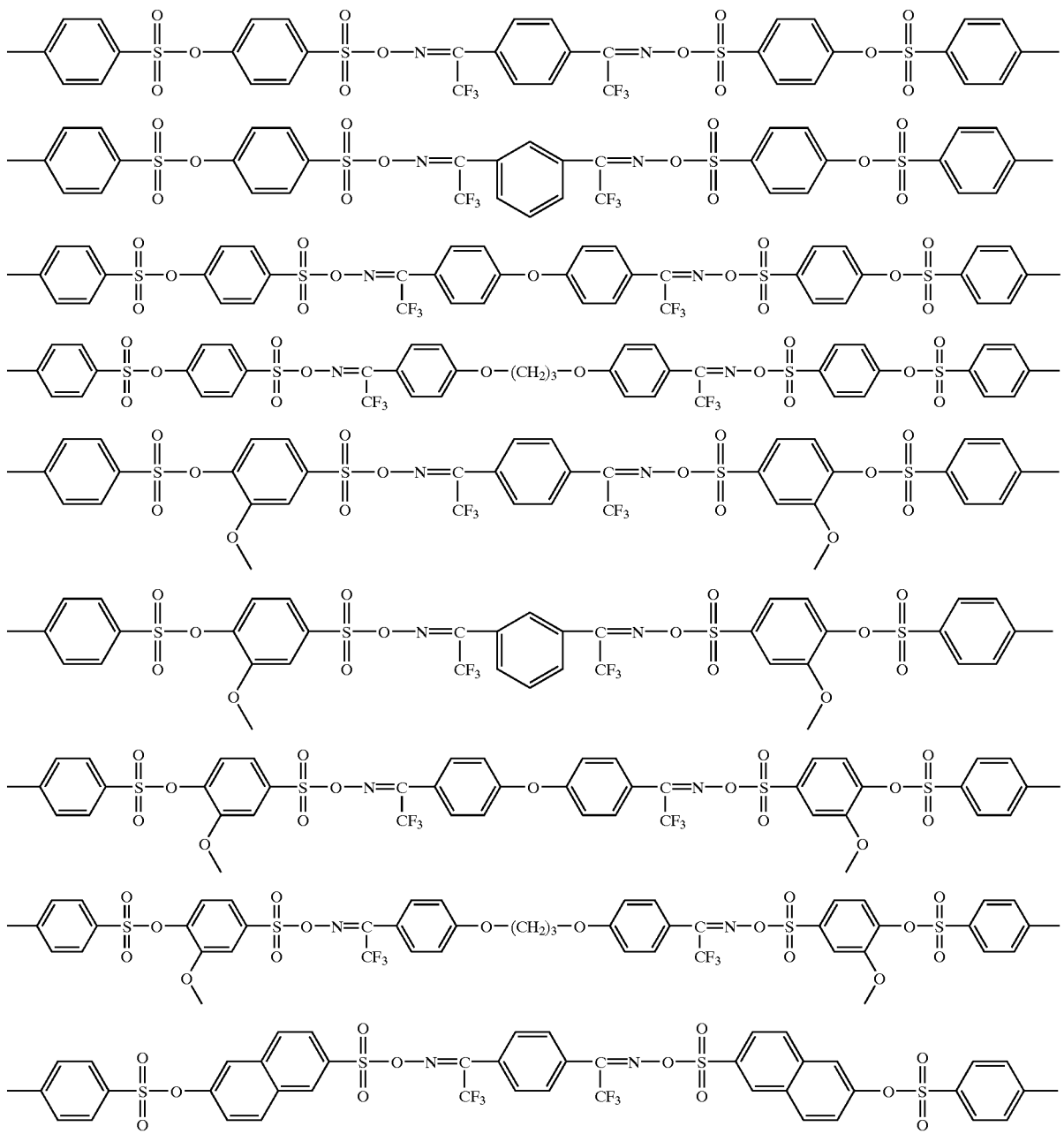

-continued

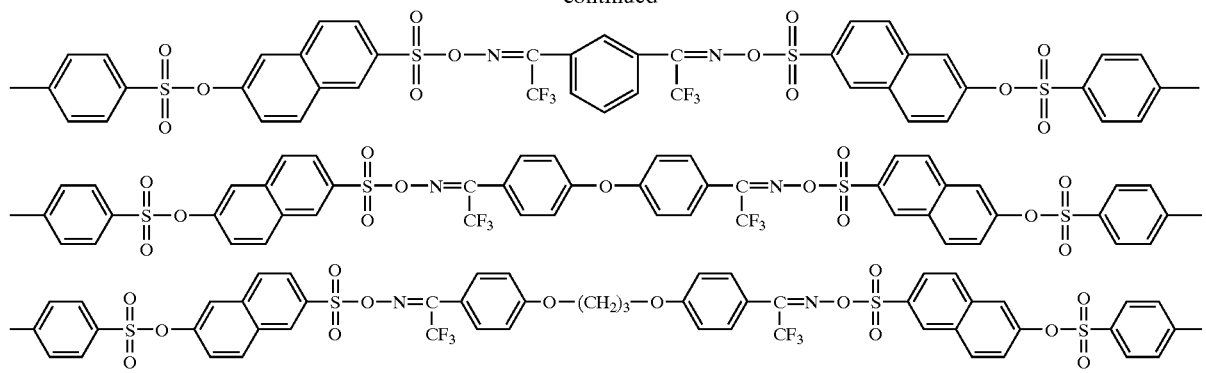

The O-arylsulfonyloxime compounds of formula (1c) according to the invention can be represented in a divided form as comprising an oxime moiety and an arylsulfonyloxy-arylsulfonyl group as shown below.

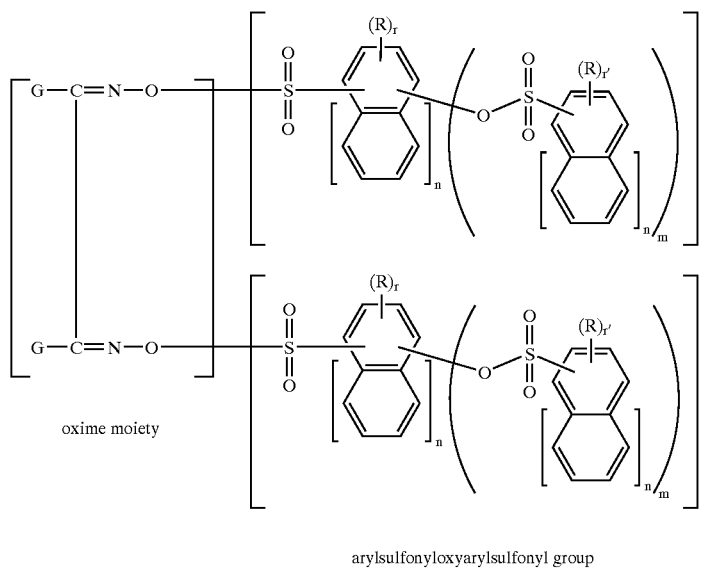

Illustrative examples of the oxime (glyoxime) moiety are given below.

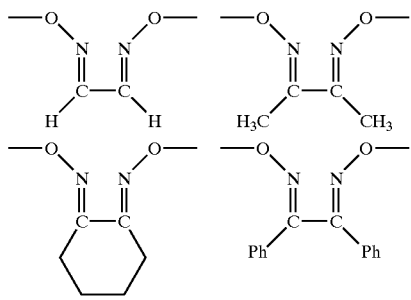

Examples of the sulfonyl group are as described for formula (1), and the combination of oxime moiety with sulfonyl group is arbitrary.

Preferred examples of the arylsulfonyloxime compounds of formula (1c) are given below.

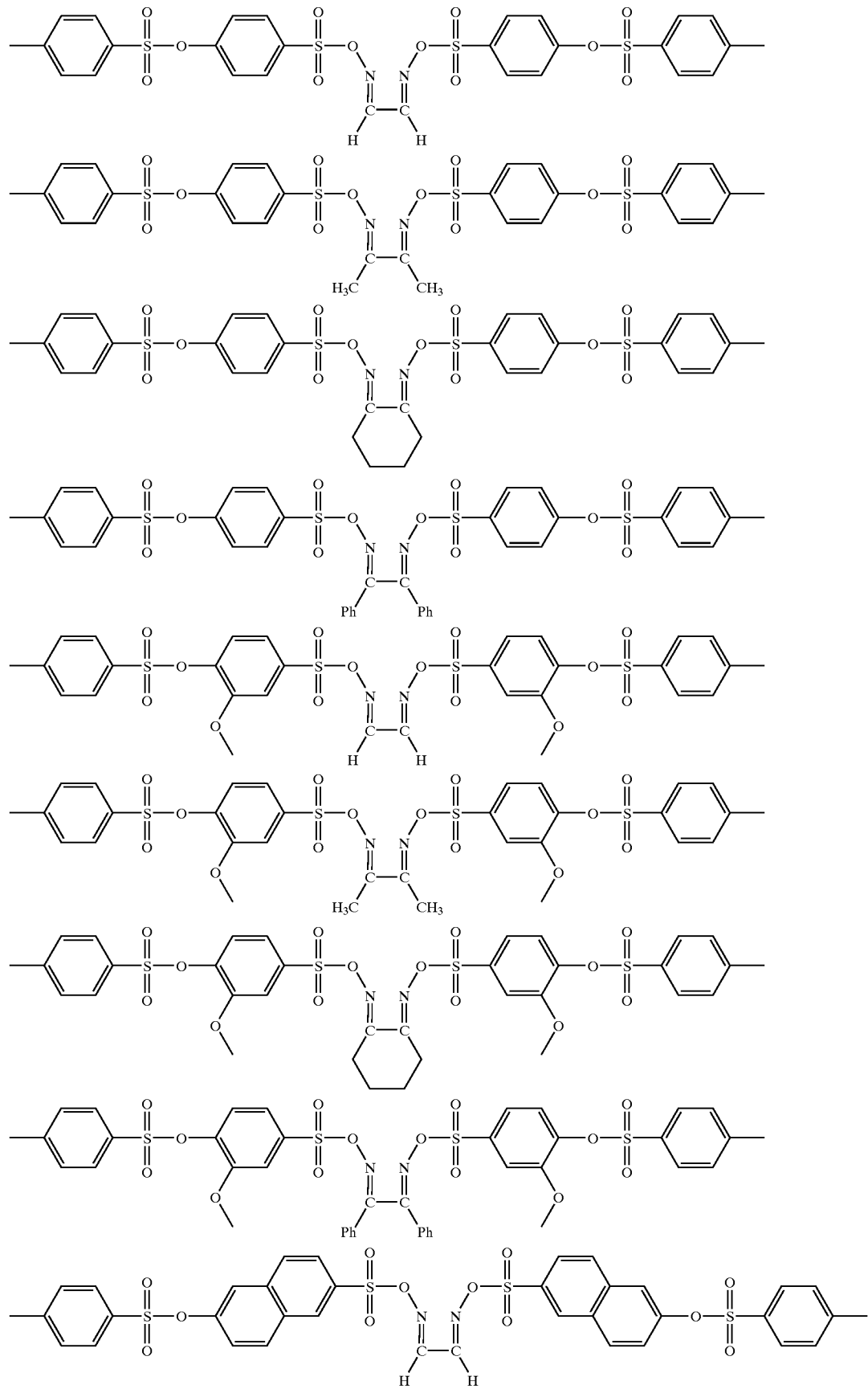

-continued
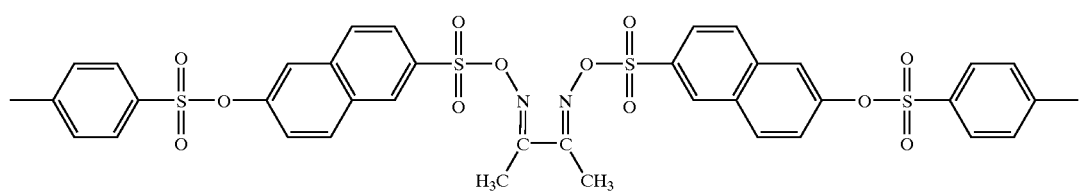
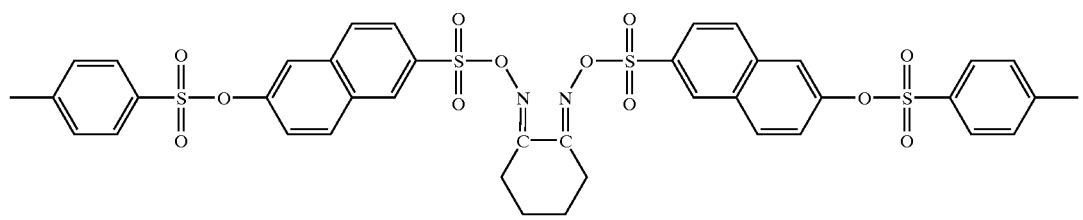
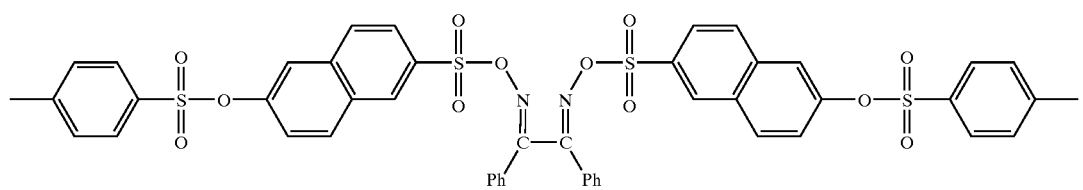
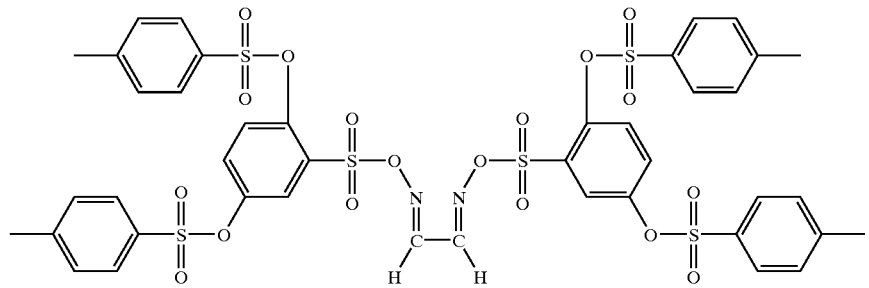
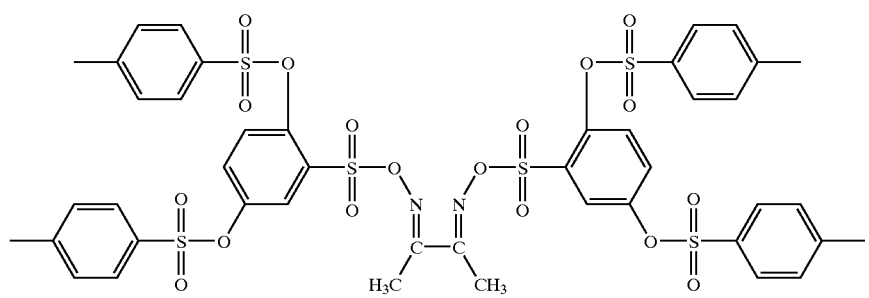
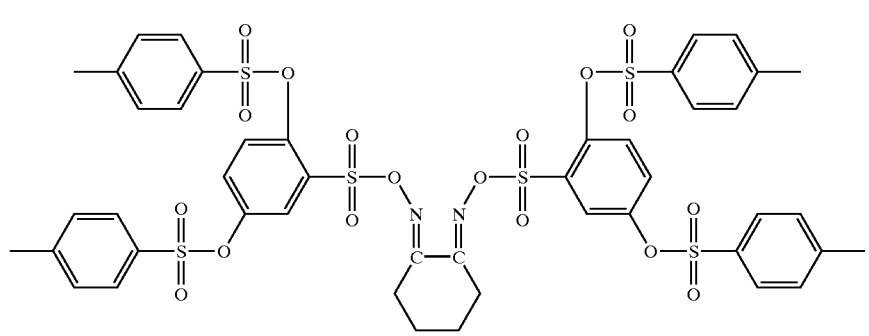

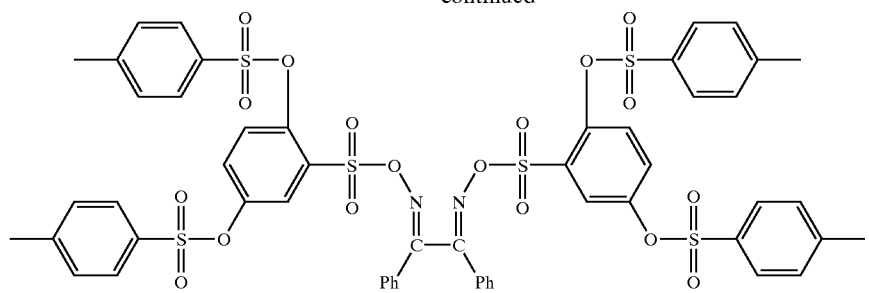

-continued

Resist Compositions

In the third aspect, the present invention provides a chemically amplified resist composition comprising a photoacid generator in the form of an O-arylsulfonyloxime compound capable of generating an arylsulfonyloxyarylsulfonic acid having the formula (1') upon exposure to radiation, or a photoacid generator of the formula (1), (1a), (1b) or (1c), the composition being sensitive to such radiation as ultraviolet radiation, deep ultraviolet radiation, electron beams, x-rays, excimer laser beams, gamma-rays or synchrotron radiation and suitable for the microfabrication of integrated circuits.

The resist compositions of the invention comprising the photoacid generator in the form of an O-arylsulfonyloxime compound capable of generating an acid of formula (1') upon exposure to radiation or the photoacid generators of formulae (1), (1a), (1b) and (1c) may be either positive or negative working. Resist compositions of the positive type are more preferred from the resolution standpoint or the like. The resist compositions of the invention include a variety of embodiments, 1) a chemically amplified positive working resist composition comprising (A) a resin which changes its solubility in an alkaline developer under the action of an acid, (B) the photoacid generator in the form of an O-arylsulfonyloxime compound capable of generating an acid of formula (1') upon exposure to radiation or the photoacid generator of formula (1), (1a), (1b) or (1c), and (F) an organic solvent;

2) a chemically amplified positive working resist composition of 1) further comprising (C) a photoacid generator capable of generating an acid upon exposure to radiation other than component (B);

3) a chemically amplified positive working resist composition of 1) or 2) further comprising (D) a basic compound;

4) a chemically amplified positive working resist composition of 1) to 3) further comprising (E) an organic acid derivative;

5) a chemically amplified positive working resist composition of 1) to 4) further comprising (G) a compound with a molecular weight of up to 3,000 which changes its solubility in an alkaline developer under the action of an acid;

6) a chemically amplified negative working resist composition comprising (B) the photoacid generator in the form of an O-arylsulfonyloxime compound capable of generating an acid of formula (1') upon exposure to radiation or the photoacid generator of formula (1), (1a), (1b) or (1c), (F) an organic solvent, (H) an alkali-soluble resin, and (I) an acid crosslinking agent capable of forming a crosslinked structure under the action of an acid;

7) a chemically amplified negative working resist composition of 6) further comprising (C) another photoacid generator;

8) a chemically amplified negative working resist composition of 6) or 7) further comprising (D) a basic compound; and 9) a chemically amplified negative working resist composition of 6) to 8) further comprising (J) an alkali soluble compound having a molecular weight of up to 2,500; but not limited thereto.

Now the respective components are described in detail.

Component (A)

Component (A) is a resin which changes its solubility in an alkaline developer solution under the action of an acid. It is preferably, though not limited thereto, an alkali-soluble resin having phenolic hydroxyl and/or carboxyl groups in which some or all of the phenolic hydroxyl and/or carboxyl groups are protected with acid-labile protective groups having a C—O—C linkage.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, hydroxyindene, methacrylic acid and acrylic acid, and such copolymers having a carboxylic derivative or diphenyl ethylene introduced at their terminus.

Also included are copolymers in which units free of alkali-soluble sites such as styrene, α-methylstyrene, acrylate, methacrylate, hydrogenated hydroxystyrene, maleic anhydride, maleimide, substituted or unsubstituted indene are introduced in addition to the above-described units in such a proportion that the solubility in an alkaline developer may not be extremely reduced. Substituents on the acrylates and methacrylates may be any of the substituents which do not undergo acidolysis. Exemplary substituents are straight, branched or cyclic $C_{1-8}$ alkyl groups and aromatic groups such as aryl groups, but not limited thereto.

Examples of the alkali-soluble resins or polymers are given below. These polymers may also be used as the material from which the resin (A) which changes its solubility in an alkaline developer under the action of an acid is prepared and as the alkali-soluble resin which serves as component (H) to be described later. Examples include poly(p-hydroxy-styrene), poly(m-hydroxystyrene), poly(4-hydroxy-2-methyl-styrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-indene copolymers, p-hydroxystyrene-acrylic acid copolymers, p-hydroxystyrene-methacrylic acid copolymers, p-hydroxystyrene-methyl acrylate copolymers, p-hydroxystyrene-acrylic acid-methyl methacrylate copolymers, p-hydroxystyrene-methyl methacrylate copolymers, p-hydroxystyrene-methacrylic acid-methyl methacrylate copolymers, poly(methacrylic acid), poly (acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-indene copolymers, p-hydroxystyrene-acrylic acid copolymers, and p-hydroxystyrene-methacrylic acid copolymers.

Alkali-soluble resins comprising units of the following formula (2), (2') or (2") are especially preferred.

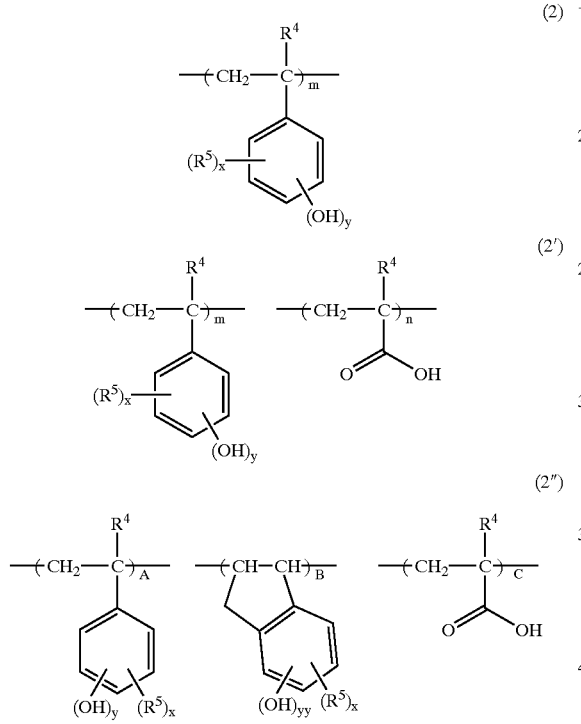

Herein $R^4$ is hydrogen or methyl, $R^5$ is a straight, branched or cyclic alkyl group of 1 to 8 carbon atoms, x is 0 or a positive integer, y is a positive integer, satisfying $x+y \leq 5$, M and N are positive integers, satisfying $0 < N/(M+N) \leq 0.5$, yy is 0 or a positive integer, satisfying $x+yy \leq 4$, and A and B are positive integers, and C is 0 or a positive integer, satisfying $0 < B/(A+B+C) \leq 0.5$.

The polymer of formula (2") can be synthesized, for example, by effecting thermal polymerization of an acetoxystyrene monomer, a tertiary alkyl (meth)acrylate monomer and an indene monomer in an organic solvent in the presence of a radical initiator, and subjecting the resulting polymer to alkaline hydrolysis in an organic solvent for deblocking the acetoxy group, for thereby forming a ternary copolymer of hydroxystyrene, tertiary alkyl (meth)acrylate and indene. The organic solvent used during polymerization is exemplified by toluene, benzene, tetrahydrofuran, diethyl ether and dioxane. Exemplary polymerization initiators include 2,2'-azobisisobutyronitrile, 2,2'-azobis(2,4-dimethylvaleronitrile), dimethyl-2,2-azobis(2-methylpropionate), benzoyl peroxide, and lauroyl peroxide. Polymerization is preferably effected while heating at 50 to 80° C. The reaction time is usually about 2 to 100 hours, preferably about 5 to 20 hours. Aqueous ammonia, triethylamine or the like may be used as the base for the alkaline hydrolysis. For the alkaline hydrolysis, the temperature is usually −20° C. to 100° C., preferably 0° C. to 60° C., and the time is about 0.2 to 100 hours, preferably about 0.5 to 20 hours.

Also included are polymers having the dendritic or hyperbranched polymer structure of formula (2'") below.

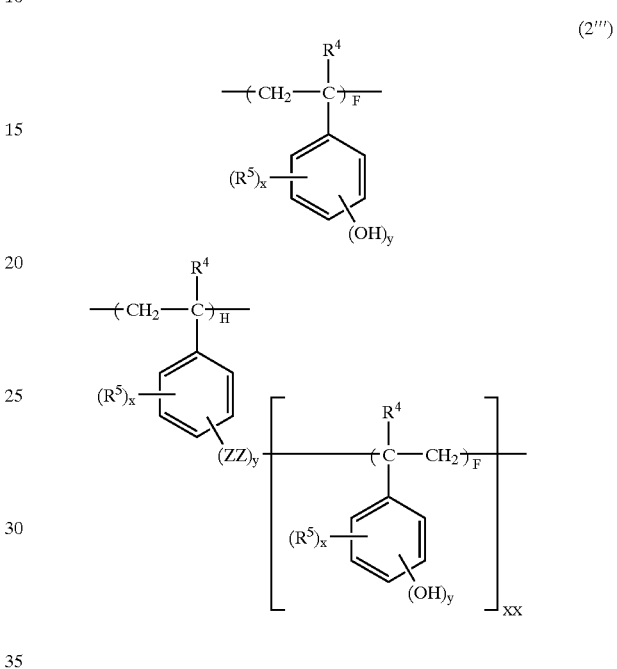

Herein ZZ is a divalent organic group selected from among $CH_2$, $CH(OH)$, $CR^5(OH)$, $C=O$ and $C(OR^5)(OH)$ or a trivalent organic group represented by $—C(OH)=$. Subscript F, which may be identical or different, is a positive integer, and H is a positive integer, satisfying $0.001 \leq H/(H+F) \leq 0.1$, and XX is 1 or 2. $R^4$, $R^5$, x and y are as defined above.

The dendritic or hyperbranched polymer of phenol derivative can be synthesized by effecting living anion polymerization of a polymerizable monomer such as 4-tert-butoxystyrene and reacting a branching monomer such as chloromethylstyrene as appropriate during the living anion polymerization.

More particularly, living anion polymerization is started using a polymerizable monomer such as 4-tert-butoxystyrene. After a predetermined amount has been polymerized, a branching monomer such as chloromethylstyrene is introduced and reacted with the intermediate. Then the polymerizable monomer such as 4-tert-butoxystyrene and/or the branching monomer such as chloromethylstyrene is added again for polymerization. This operation is repeated many times until a desired dendritic or hyperbranched polymer is obtained. If necessary, the protective groups used to enable living polymerization are deblocked, yielding a dendritic or hyperbranched polymer of phenol derivative.

Examples of the branching monomer are given below.

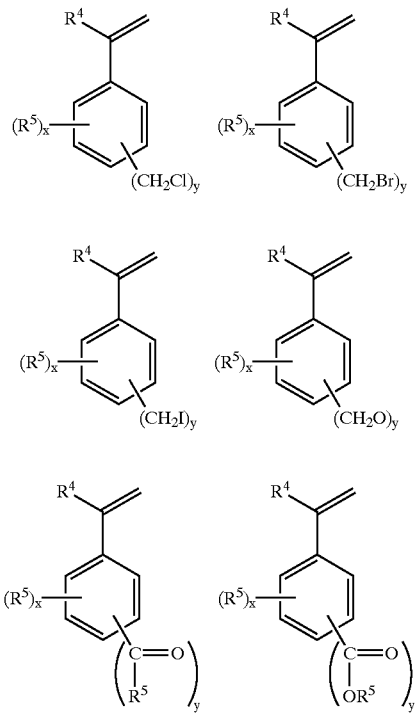

$R^4$, $R^5$, x and y are as defined above.

Illustrative examples of the dendritic or hyperbranched polymer are those having recurring units of the following approximate formulas (8) to (12).

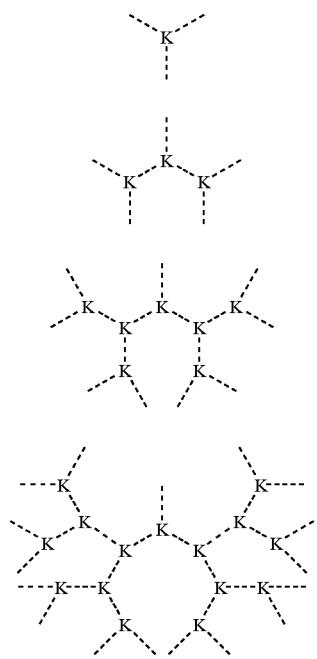

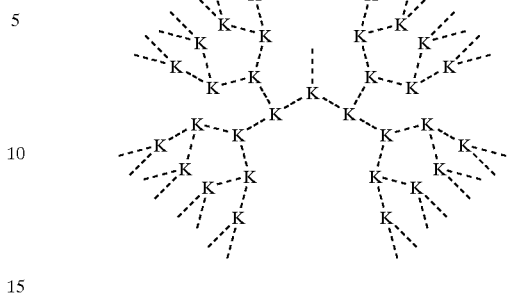

Herein, broken lines (---) represent polymer chains derived from the phenol derivative monomer, and K represents units derived from the branching monomer. The number of broken line segments between K and K is depicted merely for the sake of convenience, independent of the number of recurring units in the polymer chain included between K and K.

The dendritic or hyperbranched polymer of a phenol derivative is prepared by effecting living polymerization of the phenol derivative, reacting with a compound having a polymerizable moiety and a terminating moiety and proceeding further polymerization. By repeating this operation desired times, a dendritic or hyperbranched polymer of phenol derivative can be synthesized. The living polymerization may be effected by any desired technique although living anion polymerization is preferred because of ease of control. For the detail of synthesis, reference is made to JP-A 2000-344836.

The alkali-soluble resins or polymers should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

In the resist composition of the invention, a resin having such substituent groups with C—O—C linkages (acid labile groups) that the solubility in an alkaline developer changes as a result of severing of the C—O—C linkages under the action of an acid, especially an alkali-soluble resin as mentioned above is preferably used as component (A). Especially preferred is a polymer comprising recurring units of the above formula (2) and containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl group, the polymer having a weight average molecular weight of 3,000 to 100,000.

Also preferred is a polymer comprising recurring units of the above formula (2'), that is, a copolymer comprising p-hydroxystyrene and/or α-methyl-p-hydroxystyrene and acrylic acid and/or methacrylic acid, wherein some of the hydrogen atoms of the carboxyl groups of acrylic acid and/or methacrylic acid are substituted with acid labile groups of one or more types, and the units based on acrylate and/or methacrylate are contained in a proportion of more than 0 mol % to 50 mol %, on the average, of the copolymer, and wherein some of the hydrogen atoms of the phenolic hydroxyl groups of p-hydroxystyrene and/or α-methyl-p-hydroxystyrene may be substituted with acid labile groups of one or more types. In the preferred copolymer, the units based on acrylate and/or methacrylate and the units based on p-hydroxystyrene and/or α-methyl-p-hydroxystyrene having acid labile groups substituted thereon are contained in a proportion of more than 0 mol % to 80 mol %, on the average, of the copolymer.

Alternatively, a polymer comprising recurring units of the above formula (2″), that is, a copolymer comprising p-hydroxystyrene and/or α-methyl-p-hydroxystyrene and substituted and/or unsubstituted indene, is preferred wherein some of the hydrogen atoms of the phenolic hydroxyl groups of p-hydroxystyrene and/or α-methyl-p-hydroxystyrene are substituted with acid labile groups of one or more types, and some of the hydrogen atoms of the carboxyl groups of acrylic acid and/or methacrylic acid are substituted with acid labile groups of one or more types. Where the substituted indene has hydroxyl groups, some of the hydrogen atoms of these hydroxyl groups may be substituted with acid labile groups of one or more types. In the preferred copolymer, the units based on p-hydroxystyrene and/or α-methyl-p-hydroxystyrene having acid labile groups substituted thereon, the units based on acrylic acid and/or methacrylic acid having acid labile groups substituted thereon, and the units based on indene having acid labile groups substituted thereon are contained in a proportion of more than 0 mol % to 80 mol %, on the average, of the copolymer.

Exemplary and preferred such polymers are polymers or high molecular weight compounds comprising recurring units represented by the following general formula (2a), (2a′) or (2a″) and having a weight average molecular weight of 3,000 to 100,000.

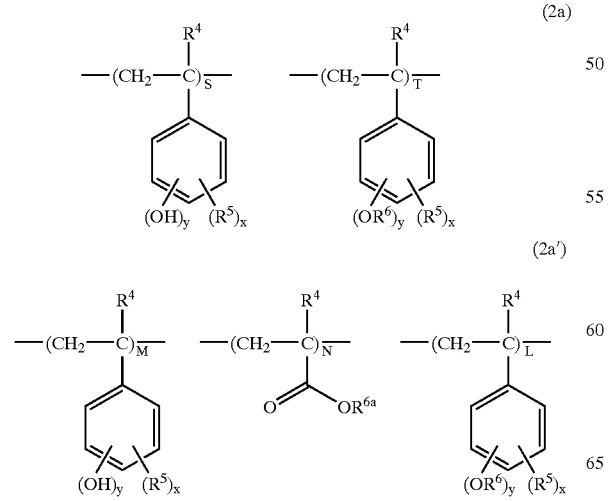

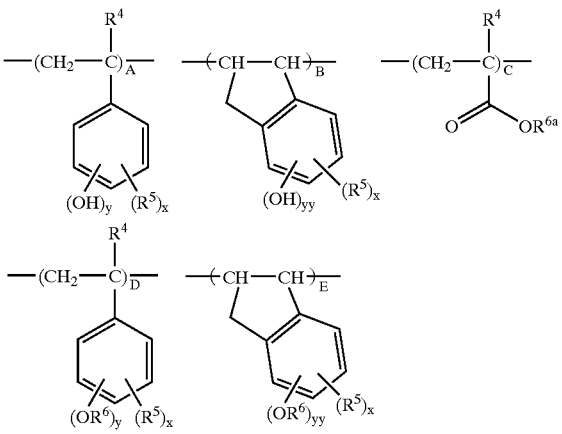

Herein, $R^4$ is hydrogen or methyl. $R^5$ is a straight, branched or cyclic alkyl group of 1 to 8 carbon atoms. Letter x is 0 or a positive integer, and y is a positive integer, satisfying $x+y \leq 5$. $R^6$ is an acid labile group. S and T are positive integers, satisfying $0<T/(S+T) \leq 0.8$. $R^{6a}$ is hydrogen or an acid labile group, at least some of the $R^{6a}$ groups are acid labile groups. M and N are positive integers, L is 0 or a positive integer, satisfying $0<N/(M+N+L) \leq 0.5$ and $0<(N+L)/(M+N+L) \leq 0.8$. The letter yy is 0 or a positive integer, satisfying $x+yy \leq 4$. A and B are positive integers, C, D and E each are 0 or a positive integer, satisfying $0<(B+E)/(A+B+C+D+E) \leq 0.5$ and $0<(C+D+E)/(A+B+C+D+E) \leq 0.8$.

$R^5$ stands for straight, branched or cyclic $C_{1-8}$ alkyl groups, for example, methyl, ethyl, propyl, isopropyl, n-butyl, isobutyl, tert-butyl, cyclohexyl and cyclopentyl.

With respect to the acid labile groups, where some of the phenolic hydroxyl groups and some or all of the carboxyl groups in the alkali-soluble resin are protected with acid labile groups having C—O—C linkages, the acid labile groups are selected from a variety of such groups. The preferred acid labile groups are groups of the following general formulae (4) to (7), tertiary alkyl groups of 4 to 20 carbon atoms, preferably 4 to 15 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms.

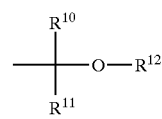 (4)

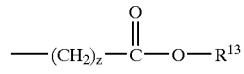 (5)

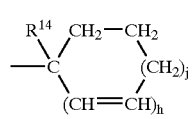 (6)

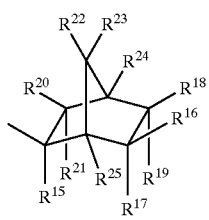
(7)

Herein $R^{10}$ and $R^{11}$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{12}$ is a monovalent hydrocarbon group of 1 to 18 carbon atoms, preferably 1 to 10 carbon atoms, which may have a hetero atom (e.g., oxygen atom), for example, straight, branched or cyclic alkyl groups, and such groups in which some hydrogen atoms are substituted with hydroxyl, alkoxy, oxo, amino or alkylamino groups. Illustrative examples of the substituted alkyl groups are given below.

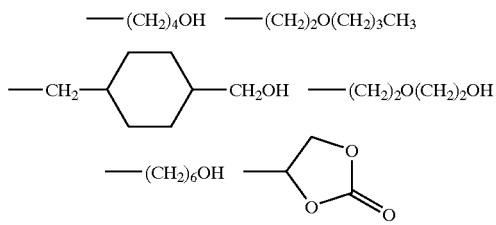

A pair of $R^{10}$ and $R^{11}$, a pair of $R^{10}$ and $R^{12}$, or a pair of $R^{11}$ and $R^{12}$, taken together, may form a ring. Each of $R^{10}$, $R^{11}$ and $R^{12}$ is a straight or branched alkylene group of 1 to 18 carbon atoms, preferably 1 to 10 carbon atoms, when they form a ring.

$R^{13}$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (4). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl and 1-adamantyl-1-methylethyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxolan-4-yl. Letter z is an integer of 0 to 6.

$R^{14}$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl and cyclohexylethyl. Exemplary substituted or unsubstituted aryl groups include phenyl, methylphenyl, naphthyl, anthryl, phenanthryl, and pyrenyl. Letter h is equal to 0 or 1, i is equal to 0, 1, 2 or 3, satisfying 2 h+i=2 or 3.

$R^{15}$ is a straight, branched or cyclic alkyl group of 1 to 8 carbon atoms or substituted or unsubstituted aryl group of 6 to 20 carbon atoms, examples of which are as exemplified for $R^{14}$. $R^{16}$ to $R^{25}$ are independently hydrogen or monovalent hydrocarbon groups of 1 to 15 carbon atoms which may contain a hetero atom, for example, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted ones of these groups in which some hydrogen atoms are substituted with hydroxyl, alkoxy, carboxy, alkoxycarbonyl, oxo, amino, alkylamino, cyano, mercapto, alkylthio, and sulfo groups. $R^{16}$ to $R^{25}$, for example, a pair of $R^{16}$ and $R^{17}$, a pair of $R^{16}$ and $R^{18}$, a pair of $R^{17}$ and $R^{19}$, a pair of $R^{18}$ and $R^{19}$, a pair of $R^{20}$ and $R^{21}$, or a pair of $R^{22}$ and $R^{23}$, taken together, may form a ring. When $R^{16}$ to $R^{25}$ form a ring, they are divalent hydrocarbon groups of 1 to 15 carbon atoms which may contain a hetero atom, examples of which are the above-exemplified monovalent hydrocarbon groups with one hydrogen atom eliminated. Also, two of $R^{16}$ to $R^{25}$ which are attached to adjacent carbon atoms (for example, a pair of $R^{16}$ and $R^{18}$, a pair of $R^{18}$ and $R^{24}$, or a pair of $R^{22}$ and $R^{24}$) may directly bond together to form a double bond.

Of the acid labile groups of formula (4), illustrative examples of the straight or branched groups are given below.

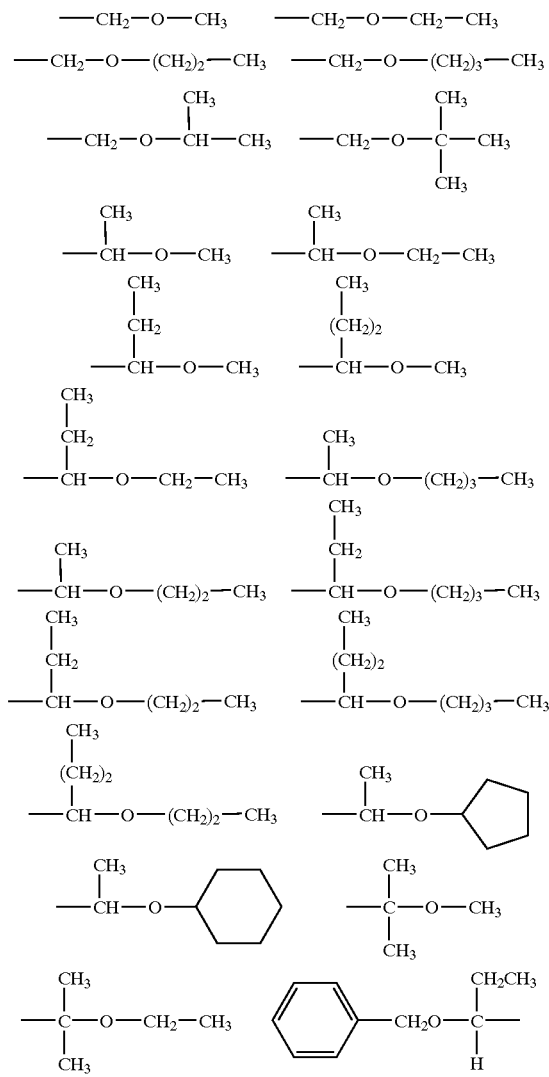

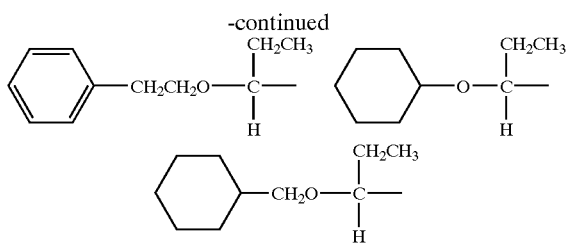
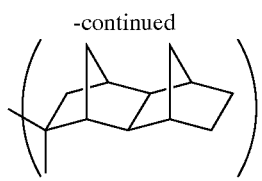

Of the acid labile groups of formula (4), illustrative examples of the cyclic groups include tetrahydrofuran-2-yl, 2-methyltetrahydrofuran-2-yl, tetrahydropyran-2-yl and 2-methyltetrahydropyran-2-yl.

Illustrative examples of the acid labile groups of formula (5) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxy-carbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Illustrative examples of the acid labile groups of formula (6) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, 3-ethyl-1-cyclohexen-3-yl, and 1-cyclohexyl-cyclopentyl.

Illustrative examples of the acid labile groups of formula (7) are given below.

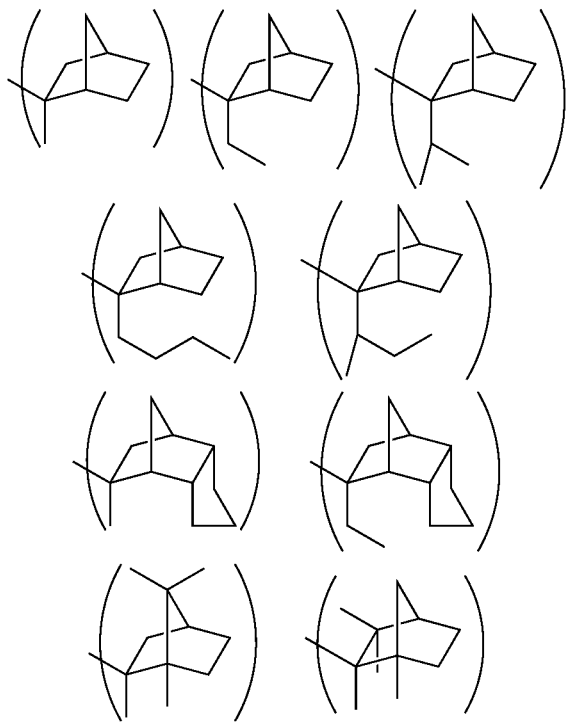

Exemplary of the tertiary alkyl group of 4 to 20 carbon atoms, preferably 4 to 15 carbon atoms, are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and 1-adamantyl-1-methylethyl.

Exemplary of the trialkylsilyl groups whose alkyl groups each have 1 to 6 carbon atoms are trimethylsilyl, triethylsilyl, and tert-butyldimethylsilyl.

Exemplary of the oxoalkyl groups of 4 to 20 carbon atoms are 3-oxocyclohexyl and groups represented by the following formulae.

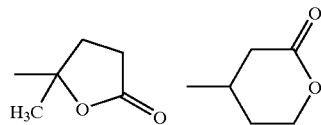

Exemplary of the aryl-substituted alkyl groups of 7 to 20 carbon atoms are benzyl, methylbenzyl, dimethylbenzyl, diphenylmethyl, and 1,1-diphenylethyl.

In the resist composition comprising the O-arylsulfonyloxime compound as a photoacid generator, the resin (A) which changes its solubility in an alkaline developer under the action of an acid may be the polymer of formula (2) or (2'), (2") or (2"') in which some of the hydrogen atoms of the phenolic hydroxyl groups are crosslinked within a molecule and/or between molecules, in a proportion of more than 0 mol % to 50 mol %, on the average, of the entire phenolic hydroxyl groups on the polymer, with crosslinking groups having C—O—C linkages represented by the following general formula (3). With respect to illustrative examples and synthesis of polymers crosslinked with acid labile groups, reference should be made to JP-A 11-190904.

(3)

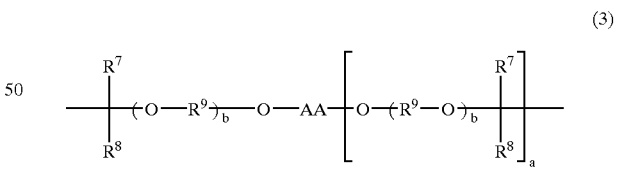

Herein, each of $R^7$ and $R^8$ is hydrogen or a straight, branched or cyclic alkyl group of 1 to 8 carbon atoms, or $R^7$ and $R^8$, taken together, may form a ring, and each of $R^7$ and $R^8$ is a straight or branched alkylene group of 1 to 8 carbon atoms when they form a ring. $R^9$ is a straight, branched or cyclic alkylene group of 1 to 10 carbon atoms. Letter "a" is an integer of 1 to 7, especially 1 to 3. Letter "b" is 0 or an integer of 1 to 10. AA is an a-valent aliphatic or alicyclic saturated hydrocarbon group, aromatic hydrocarbon group or heterocyclic group of 1 to 50 carbon atoms, which may be separated by a hetero atom and in which some of the hydrogen atom attached to carbon atoms may be substituted with hydroxyl, carboxyl, carbonyl or halogen.

Preferably in formula (3), $R^7$ is methyl, $R^8$ is hydrogen, a is 1, b is 0, and AA is ethylene, 1,4-butylene or 1,4-cyclohexylene.

It is noted that these polymers which are crosslinked within the molecule or between molecules with crosslinking groups having C—O—C linkages can be synthesized by reacting a corresponding non-crosslinked polymer with an alkenyl ether in the presence of an acid catalyst in a conventional manner.

If decomposition of other acid labile groups proceeds under acid catalyst conditions, the end product can be obtained by once reacting the alkenyl ether with hydrochloric acid or the like for conversion to a halogenated alkyl ether and reacting it with the polymer under basic conditions in a conventional manner.

Illustrative, non-limiting, examples of the alkenyl ether include ethylene glycol divinyl ether, triethylene glycol divinyl ether, 1,2-propanediol divinyl ether, 1,3-propanediol divinyl ether, 1,3-butanediol divinyl ether, 1,4-butanediol divinyl ether, neopentyl glycol divinyl ether, trimethylolpropane trivinyl ether, trimethylolethane trivinyl ether, hexanediol divinyl ether, and 1,4-cyclohexanediol divinyl ether.

In the chemical amplification type positive resist composition, the resin used as component (A) is as described above while the preferred acid labile groups to be substituted for phenolic hydroxyl groups are 1-ethoxyethyl, 1-ethoxypropyl, tetrahydrofuranyl, tetrahydropyranyl, tert-butyl, tert-amyl, 1-ethylcyclohexyloxycarbonylmethyl, tert-butoxycarbonyl, tert-butoxycarbonylmethyl, and substituents of formula (3) wherein $R^7$ is methyl, $R^8$ is hydrogen, a is 1, b is 0, and AA is ethylene, 1,4-butylene or 1,4-cyclohexylene. Also preferably, the hydrogen atoms of carboxyl groups of methacrylic acid or acrylic acid are protected with substituent groups as typified by tert-butyl, tert-amyl, 2-methyl-2-adamantyl, 2-ethyl-2-adamantyl, 1-ethylcyclopentyl, 1-ethylcyclohexyl, 1-cyclohexylcyclopentyl, 1-ethylnorbornyl, tetrahydrofuranyl and tetrahydropyranyl.

In a single polymer, these substituents may be incorporated alone or in admixture of two or more types. A blend of two or more polymers having substituents of different types is also acceptable.

The percent proportion of these substituents substituting for phenol and carboxyl groups in the polymer is not critical. Preferably the percent substitution is selected such that when a resist composition comprising the polymer is applied onto a substrate to form a coating, the unexposed area of the coating may have a dissolution rate of 0.01 to 10 Å/sec in a 2.38% tetramethylammonium hydroxide (TMAH) developer.

On use of a polymer containing a greater proportion of carboxyl groups which can reduce the alkali dissolution rate, the percent substitution must be increased or non-acid-decomposable substituents to be described later must be introduced.

When acid labile groups for intramolecular and/or intermolecular crosslinking are to be introduced, the percent proportion of crosslinking substituents is preferably up to 20 mol %, more preferably up to 10 mol %, on the average, based on the entire hydrogen atoms of phenolic hydroxyl groups. If the percent substitution of crosslinking substituents is too high, crosslinking results in a higher molecular weight which can adversely affect dissolution, stability and resolution. It is also preferred to further introduce another non-crosslinking acid labile group into the crosslinked polymer at a percent substitution of up to 10 mol % for adjusting the dissolution rate to fall within the above range.

In the case of poly(p-hydroxystyrene), the optimum percent substitution differs between a substituent having a strong dissolution inhibitory action such as a tert-butoxycarbonyl group and a substituent having a weak dissolution inhibitory action such as an acetal group although the overall percent substitution is preferably 10 to 40 mol %, more preferably 20 to 30 mol %, on the average, based on the entire hydrogen atoms of phenolic hydroxyl groups in the polymer.

Polymers having such acid labile groups introduced therein should preferably have a weight average molecular weight (Mw) of 3,000 to 100,000. With a Mw of less than 3,000, polymers would perform poorly and often lack heat resistance and film formability. Polymers with a Mw of more than 100,000 would be less soluble in a developer and a resist solvent.

Where non-crosslinking acid labile groups are introduced, the polymer should preferably have a dispersity (Mw/Mn) of up to 3.5, preferably up to 1.5. A polymer with a dispersity of more than 3.5 often results in a low resolution. Where crosslinking acid labile groups are introduced, the starting alkali-soluble resin should preferably have a dispersity (Mw/Mn) of up to 1.5, and the dispersity is kept at 3 or lower even after protection with crosslinking acid labile groups. If the dispersity is higher than 3, dissolution, coating, storage stability and/or resolution is often poor.

To impart a certain function, suitable substituent groups may be introduced into some of the phenolic hydroxyl and carboxyl groups on the acid labile group-protected polymer. Exemplary are substituent groups for improving adhesion to the substrate, non-acid-labile groups for adjusting dissolution in an alkali developer, and substituent groups for improving etching resistance. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxoranyl, 4-methyl-2-oxo-4-oxanyl, methyl, ethyl, propyl, n-butyl, sec-butyl, acetyl, pivaloyl, adamantyl, isoboronyl, and cyclohexyl.

In the resist composition of the invention, the above-described resin is added in any desired amount, and usually 65 to 99 parts by weight, preferably 65 to 98 parts by weight per 100 parts by weight of the solids in the composition. The term "solids" is used to encompass all components in the resist composition excluding the solvent.

Illustrative examples of the photoacid generator in the form of an O-arylsulfonyloxime compound capable of generating an acid of formulae (1') upon exposure to radiation or the photoacid generators of formulae (1), (1a), (1b) and (1c) are as described above.

In the chemical amplification resist composition, an appropriate amount of the photoacid generator added is from 0.1 part to 10 parts by weight, and preferably from 1 to 5 parts by weight, per 100 parts by weight of the solids in the composition. A less amount of the photoacid generator below the range fails to generate a sufficient amount of acid to deblock acid labile groups in the polymer. Too large amounts may excessively reduce the transmittance of resist film, failing to form a rectangular pattern, and give rise to problems of abnormal particles and deposits during resist storage. The photoacid generators may be used alone or in admixture of two or more.

Component (C)

In one preferred embodiment, the resist composition further contains (C) a compound capable of generating an acid upon exposure to high-energy radiation (UV, deep UV, electron beams, x-rays, excimer laser beams, gamma-rays or synchrotron radiation), that is, a second photoacid generator other than component (B). Suitable second photoacid generators include sulfonium salts, iodonium salts, sulfonyldiazomethane and N-sulfonyloxydicarboxyimide photoacid generators. Exemplary second photoacid generators are given below while they may be used alone or in admixture of two or more.

Sulfonium salts are salts of sulfonium cations with sulfonates. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxy-phenyl)diphenylsulfonium, bis(3,4-di-tert-butoxyphenyl)-phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyl-dimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethyl-sulfonium, dimethylphenylsulfonium, and 2-oxo-2-phenylethyl-thiacyclopentanium. Exemplary sulfonates include trifluoromethanesulfonate, nonafluorobutanesulfonate, heptadecafluorooctanesulfonate, 2,2,2-trifluoroethane-sulfonate, pentafluorobenzenesulfonate, 4-trifluoromethyl-benzenesulfonate, 4-fluorobenzenesulfonate, mesitylene-sulfonate, 2,4,6-triisopropylbenzenesulfonate, toluene-sulfonate, benzenesulfonate, 4-(4'-toluenesulfonyloxy)-benzenesulfonate, naphthalenesulfonate, camphorsulfonate, octanesulfonate, dodecylbenzenesulfonate, butanesulfonate, and methanesulfonate. Sulfonium salts based on combination of the foregoing examples are included.

Iodinium salts are salts of iodonium cations with sulfonates. Exemplary iodinium cations are aryliodonium cations including diphenyliodinium, bis(4-tert-butylphenyl)-iodonium, 4-tert-butoxyphenylphenyliodonium, and 4-methoxyphenylphenyliodonium. Exemplary sulfonates include trifluoromethanesulfonate, nonafluorobutane-sulfonate, heptadecafluorooctanesulfonate, 2,2,2-trifluoroethanesulfonate, pentafluorobenzenesulfonate, 4-trifluoromethylbenzenesulfonate, 4-fluorobenzene-sulfonate, mesitylenesulfonate, 2,4,6-triisopropylbenzenesulfonate, toluenesulfonate, benzenesulfonate, 4-(4-toluenesulfonyloxy)-benzenesulfonate, naphthalenesulfonate, camphorsulfonate, octanesulfonate, dodecylbenzenesulfonate, butanesulfonate, and methanesulfonate. Iodonium salts based on combination of the foregoing examples are included.

Exemplary sulfonyldiazomethane compounds include bissulfonyldiazomethane compounds and sulfonylcarbonyl-diazomethane compounds such as bis(ethylsulfonyl)diazomethane, bis(1-methylpropylsulfonyl)diazomethane, bis(2-methylpropyl-sulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)-diazomethane, bis(2,4-dimethylphenylsulfonyl)diazomethane, bis(2-naphthylsulfonyl)diazomethane, bis(4-acetyloxyphenyl-sulfonyl)diazomethane, bis(4-methanesulfonyloxyphenyl-sulfonyl)diazomethane, bis(4-(4-toluenesulfonyloxy)phenyl-sulfonyl)diazomethane, 4-methylphenylsulfonylbenzoyldiazo-methane, tert-butylcarbonyl-4-methylphenylsulfonyldiazomethane, 2-naphthylsulfonylbenzoyldiazomethane, 4-methyl-phenylsulfonyl-2-naphthoyldiazomethane, methylsulfonyl-benzoyldiazomethane, and tert-butoxycarbonyl-4-methylphenyl-sulfonyldiazomethane.

N-sulfonyloxydicarboxyimide photoacid generators include combinations of imide skeletons with sulfonates. Exemplary imide skeletons are succinimide, naphthalene-dicarboxyimide, phthalimide, cyclohexyldicarboxyimide, 5-norbornene-2,3-dicarboxyimide, and 7-oxabicyclo[2.2.1]-5-heptene-2,3-dicarboxyimide. Exemplary sulfonates include trifluoromethanesulfonate, nonafluorobutane-sulfonate, heptadecafluorooctanesulfonate, 2,2,2-trifluoroethane-sulfonate, pentafluorobenzenesulfonate, 4-trifluoromethyl-benzenesulfonate, 4-fluorobenzene-sulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, and methanesulfonate.

Benzoinsulfonate photoacid generators include benzoin tosylate, benzoin mesylate, and benzoin butanesulfonate.

Pyrogallol trisulfonate photoacid generators include pyrogallol, fluoroglycine, catechol, resorcinol, hydroquinone, in which all the hydroxyl groups are substituted with trifluoromethanesulfonate, nonafluorobutane-sulfonate, heptadecafluorooctanesulfonate, 2,2,2-trifluoroethane-sulfonate, pentafluorobenzenesulfonate, 4-trifluoromethyl-benzenesulfonate, 4-fluorobenzene-sulfonate, toluenesulfonate, benzenesulfonate, naphthalenesulfonate, camphorsulfonate, octanesulfonate, dodecylbenzenesulfonate, butanesulfonate, methanesulfonate or the like.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, nonafluorobutanesulfonate, heptadecafluorooctanesulfonate, 2,2,2-trifluoroethane-sulfonate, pentafluorobenzenesulfonate, 4-trifluoromethyl-benzenesulfonate, 4-fluorobenzenesulfonate, toluenesulfonate, benzenesulfonate, naphthalenesulfonate, camphorsulfonate, octanesulfonate, dodecylbenzene-sulfonate, butanesulfonate, and methanesulfonate. Also useful are analogous nitrobenzyl sulfonate compounds in which the nitro group on the benzyl side is substituted with a trifluoromethyl group.

Sulfone photoacid generators include bis(phenylsulfonyl)methane, bis(4-methylphenylsulfonyl)-methane, bis(2-naphthylsulfonyl)methane, 2,2-bis(phenyl-sulfonyl)propane, 2,2-bis(4-methylphenylsulfonyl)propane, 2,2-bis(2-naphthylsulfonyl)propane, 2-methyl-2-(p-toluene-sulfonyl)propiophenone, 2-cyclohexylcarbonyl-2-(p-toluene-sulfonyl)propane, and 2,4-dimethyl-2-(p-toluenesulfonyl)-pentan-3-one.

Photoacid generators in the form of glyoxime derivatives include bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime, bis-O-(p-toluenesulfonyl)-2,3-pentanedioneglyoxime,
bis-O-(p-toluenesulfonyl)-2-methyl-3,4-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime,
bis-O-(perfluorooctanesulfonyl)-α-dimethylglyoxime,
bis-O-(cyclohexylsulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime.

Also included are the compounds described in U.S. Pat. Nos. 6,004,724, 6,261,738, JP-A 9-95479, JP-A 9-208554, JP-A 9-230588, Japanese Patent No. 2,906,999, JP-A 9-301948, JP-A 2000-314956, and JP-A 2001-233842.

Of these, preferred photoacid generators are sulfonium salts, bissulfonyldiazomethanes, and N-sulfonyloxydicarboxyimides. Illustrative preferred photoacid generators include triphenylsulfonium p-toluenesulfonate, triphenylsulfonium camphorsulfonate, triphenylsulfonium pentafluorobenzene-sulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluene-sulfonyloxy)benzenesulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenyl-sulfonyl)diazomethane, bis(4-tert-butylphenylsulfonyl)diazo-methane, N-camphorsulfonyloxy-5-norbornene-2,3-carboxylic acid imide, and N-p-toluenesulfonyloxy-5-norbornene-2,3-carboxylic acid imide.

In the resist composition comprising the O-arylsulfonyloxime compound as the first photoacid generator (B) according to the invention, the second photoacid generator (C) may be used in any desired amount as long as it does not compromise the effects of the O-arylsulfonyloxime compound. An appropriate amount of the second photoacid generator (C) is 0 to 10 parts, and especially 0 to 5 parts by weight per 100 parts by weight of the solids in the composition. Too high a proportion of the second photoacid generator (C) may give rise to problems of degraded resolution and foreign matter upon development and resist film peeling. The second photoacid generators may be used alone or in admixture of two or more. The transmittance of the resist film can be controlled by using a (second) photoacid generator having a low transmittance at the exposure wavelength and adjusting the amount of the photoacid generator added.

In the resist composition comprising the O-arylsulfonyloxime compound as the photoacid generator according to the invention, there may be added a compound which is decomposed with an acid to generate an acid, that is, acid-propagating compound. For these compounds, reference should be made to J. Photopolym. Sci. and Tech., 8, 43–44, 45–46 (1995), and ibid., 9, 29–30 (1996).

Examples of the acid-propagating compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid-propagating compound-like behavior.

In the resist composition of the invention, an appropriate amount of the acid-propagating compound is up to 2 parts, and especially up to 1 part by weight per 100 parts by weight of the solids in the composition. Excessive amounts of the acid-propagating compound makes diffusion control difficult, leading to degradation of resolution and pattern configuration.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (D1) may also be included alone or in admixture.

$$N(X')_w(Y)_{3-w} \qquad \text{D1}$$

In the formula, w is equal to 1, 2 or 3; Y is independently hydrogen or a straight, branched or cyclic alkyl group of 1 to 20 carbon atoms which may contain a hydroxyl group or ether structure; and X' is independently selected from groups of the following general formulas (X'1) to (X'3), and two or three X' may bond together to form a ring.

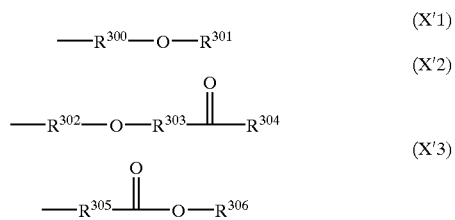

In the formulas, $R^{300}$, $R^{302}$ and $R^{305}$ are independently straight or branched alkylene groups of 1 to 4 carbon atoms; $R^{301}$, $R^{304}$ and $R^{306}$ are independently hydrogen, straight, branched or cyclic alkyl groups of 1 to 20 carbon atoms, which may contain at least one hydroxyl group, ether structure, ester structure or lactone ring; and $R^{303}$ is a single bond or a straight or branched alkylene group of 1 to 4 carbon atoms.

Illustrative examples of the basic compounds of formula (D1) include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)-ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxy-ethyl)amine, tris(2-tert-butoxycarbonyloxy-ethyl)amine, tris[2-(2-oxopropoxy)ethyl]amine, tris[2-(methoxycarbonyl-methyl)oxyethyl]amine, tris[2-(tert-butoxycarbonyl-methyloxy)ethyl]amine, tris[2-(cyclohexyloxycarbonyl-methyloxy)ethyl]amine, tris(2-methoxycarbonylethyl) amine, tris(2-ethoxycarbonylethyl)amine, N,N-bis(2-hydroxyethyl)-2-(methoxycarbonyl)-ethylamine, N,N-bis(2-acetoxyethyl)-2-(methoxycarbonyl)-ethylamine, N,N-bis(2-hydroxyethyl)-2-(ethoxycarbonyl)-ethylamine, N,N-bis(2-acetoxyethyl)-2-(ethoxycarbonyl)-ethylamine, N,N-bis(2-hydroxyethyl)-2-(2-methoxyethoxy-carbonyl) ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl) methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl) ethylamine, N,N-bis(2-hydroxyethyl)-2-(tetrahydrofurfuryloxycarbonyl)-ethylamine, N,N-bis(2-acetoxyethyl)-2-(tetrahydrofurfuryl-oxycarbonyl) ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl) oxycarbonyl]-ethylamine, N,N-bis(2-hydroxyethyl)-2-(4-hydroxybutoxycarbonyl)ethylamine, N,N-bis(2-formyloxyethyl)-2-(4-formyloxybutoxycarbonyl) ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl] amine, N-(2-methoxyethyl)-bis[2-(methoxycarbonyl)ethyl] amine, N-butyl-bis[2-(methoxycarbonyl)ethyl]amine, N-butyl-bis[2-(2-methoxyethoxycarbonyl)ethyl]amine, N-methyl-bis(2-acetoxy-ethyl)amine, N-ethyl-bis(2-acetoxyethyl)amine, N-methyl-bis(2-pivaloyloxyethyl) amine, N-ethyl-bis[2-(methoxycarbonyloxy)ethyl]amine, N-ethyl-bis[2-(tert-butoxy-carbonyloxy)ethyl]amine, tris(methoxycarbonylmethyl)amine, tris(ethoxycarbonyl-methyl)amine, N-butyl-bis(methoxycarbonyl-methyl) amine, N-hexyl-bis(methoxycarbonylmethyl)amine, and β-(diethylamino)-δ-valerolactone.

Also useful are one or more of cyclic structure-bearing basic compounds having the following general formula (D2).

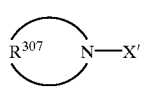
(D2)

Herein X' is as defined above, and $R^{307}$ is a straight or branched alkylene group of 2 to 20 carbon atoms which may contain one or more carbonyl groups, ether structures, ester structures or sulfide structures.

Illustrative examples of the cyclic structure-bearing basic compounds having formula (D2) include 1-[2-(methoxymethoxy)ethyl]pyrrolidine, 1-[2-(methoxymethoxy)ethyl]-piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxy-carbonyloxy)ethyl]piperidine, 4-[2-(2-methoxyethoxy-carbonyloxy)ethyl]morpholine, methyl 3-(1-pyrrolidinyl)-propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidino-propionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)-ethyl 3-(1-pyrrolidinyl)propionate, butyl 3-morpholinopropionate, cyclohexyl 3-piperidinopropionate, α-(1-pyrrolidinyl) methyl-γ-butyrolactone, β-piperidino-γ-butyrolactone, β-morpholino-δ-valerolactone, methyl 1-pyrrolidinyl-acetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (D3) to (D6) may be blended.

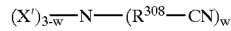
(D3)

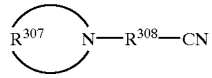
(D4)

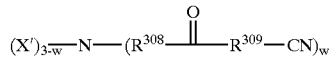
(D5)

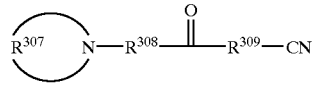
(D6)

Herein, X', $R^{307}$ and w are as defined above, and $R^{308}$ and $R^{309}$ each are independently a straight or branched alkylene group of 1 to 4 carbon atoms.

Illustrative examples of the cyano-bearing basic compounds having formulae (D3) to (D6) include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropanoate, methyl N-(2-cyanoethyl)-N-(2-hydroxyethyl)-3-aminopropanoate, methyl N-(2-acetoxyethyl)-N-(2-cyanoethyl)-3-aminopropanoate, N-(2-cyanoethyl)-N-ethyl-3-aminopropanoate, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylamino-acetonitrile, N,N-bis(2-hydroxyethyl)aminoacetonitrile, N,N-bis(2-acetoxyethyl) aminoacetonitrile, N,N-bis(2-formyloxyethyl) aminoacetonitrile, N,N-bis(2-methoxyethyl) aminoacetonitrile, N,N-bis[2-(methoxymethoxy)ethyl] aminoacetonitrile, methyl N-cyanomethyl-N-(2-methoxyethyl)-3-aminopropanoate, methyl N-cyanomethyl-N-(2-hydroxyethyl)-3-aminopropanoate, methyl N-(2-acetoxyethyl)-N-cyanomethyl-3-aminopropanoate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)-ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)-ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The basic compounds may be used alone or in admixture of two or more. The basic compound is preferably formulated in an amount of 0 to 2 parts, and especially 0.01 to 1 part by weight, per 100 parts by weight of the solids in the resist composition. The use of more than 2 parts of the basis compound would result in too low a sensitivity.

Component (E)

Illustrative, non-limiting, examples of the organic acid derivatives (E) include phenol, cresol, catechol, resorcinol, pyrogallol, fluoroglycin, bis(4-hydroxyphenyl)-methane, 2,2-bis(4'-hydroxyphenyl)propane, bis(4-hydroxy-phenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxy-phenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition of the invention, the organic acid derivative is preferably formulated in an amount of up to 5 parts, and especially up to 1 part by weight, per 100 parts by weight of the solids in the resist composition. The use of more than 5 parts of the organic acid derivative would result in too low a resolution. Depending on the combination of the other components in the resist composition, the organic acid derivative may be omitted.

Component (F)

Component (F) is an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methylpyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethyl sulfoxide, γ-butyrolactone, propylene glycol methyl ether acetate, propylene glycol ethyl ether acetate, propylene glycol propyl ether acetate, methyl lactate, ethyl lactate, propyl lactate, and tetramethyl sulfone. Of these, the propylene glycol alkyl ether acetates and alkyl lactates are especially preferred. The solvents may be used alone or in admixture of two or more. An exemplary useful solvent mixture is a mixture of a propylene glycol alkyl ether acetate and an alkyl lactate. It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred.

When the propylene glycol alkyl ether acetate is used as the solvent, it preferably accounts for at least 50% by weight of the entire solvent. Also when the alkyl lactate is used as the solvent, it preferably accounts for at least 50% by weight of the entire solvent. When a mixture of propylene glycol alkyl ether acetate and alkyl lactate is used as the solvent, that mixture preferably accounts for at least 50% by weight of the entire solvent.

The solvent is preferably used in an amount of 300 to 2,000 parts by weight, especially 400 to 1,000 parts by weight per 100 parts by weight of the solids in the resist composition. The solvent concentration is not limited thereto as long as a film can be formed by existing methods.

Component (G)

In one preferred embodiment, the resist composition further contains (G) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 2,500 is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxy-phenyl)ethane, 1,1,2-tris(4'-hydroxyphenyl)ethane, phenolphthalein, and thymolphthalein. The acid labile substituents are the same as those exemplified as the acid labile groups in the polymer.

Illustrative, non-limiting, examples of the dissolution inhibitors which are useful herein include
bis(4-(2'-tetrahydropyranyloxy)phenyl)methane,
bis(4-(2'-tetrahydrofuranyloxy)phenyl)methane,
bis(4-tert-butoxyphenyl)methane,
bis(4-tert-butoxycarbonyloxyphenyl)methane,
bis(4-tert-butoxycarbonylmethyloxyphenyl)methane, bis(4-(1'-ethoxyethoxy)phenyl)methane,
bis(4-(1'-ethoxypropyloxy)phenyl)methane,
2,2-bis(4'-(2"-tetrahydropyranyloxy))propane,
2,2-bis(4'-(2"-tetrahydrofuranyloxy)phenyl)propane,
2,2-bis(4'-tert-butoxyphenyl)propane,
2,2-bis(4'-tert-butoxycarbonyloxyphenyl)propane,
2,2-bis(4-tert-butoxycarbonylmethyloxyphenyl)propane,
2,2-bis(4'-(1"-ethoxyethoxy)phenyl)propane,
2,2-bis(4'-(1"-ethoxypropyloxy)phenyl)propane, tert-butyl 4,4-bis(4'-(2"-tetrahydropyranyloxy)phenyl)valerate,
tert-butyl 4,4-bis(4'-(2"-tetrahydrofuranyloxy)phenyl)-valerate, tert-butyl 4,4-bis(4'-tert-butoxyphenyl)valerate,
tert-butyl 4,4-bis(4-tert-butoxycarbonyloxyphenyl)valerate,
tert-butyl 4,4-bis(4'-tert-butoxycarbonylmethyloxyphenyl)-valerate, tert-butyl 4,4-bis(4'-(1"-ethoxyethoxy)phenyl)-valerate, tert-butyl 4,4-bis(4'-(1"-ethoxypropyloxy)phenyl)-valerate, tris(4-(2'-tetrahydropyranyloxy)phenyl)methane,
tris(4-(2'-tetrahydrofuranyloxy)phenyl)methane,
tris(4-tert-butoxyphenyl)methane,
tris(4-tert-butoxycarbonyloxyphenyl)methane,
tris(4-tert-butoxycarbonyloxymethylphenyl)methane,
tris(4-(1'-ethoxyethoxy)phenyl)methane,
tris(4-(1'-ethoxypropyloxy)phenyl)methane,
1,1,2-tris(4'-(2"-tetrahydropyranyloxy)phenyl)ethane,
1,1,2-tris(4'-(2"-tetrahydrofuranyloxy)phenyl)ethane,
1,1,2-tris(4'-tert-butoxyphenyl)ethane,
1,1,2-tris(4'-tert-butoxycarbonyloxyphenyl)ethane,
1,1,2-tris(4'-tert-butoxycarbonylmethyloxyphenyl)ethane,
1,1,2-tris(4'-(1'-ethoxyethoxy)phenyl)ethane, and
1,1,2-tris(4'-(1'-ethoxypropyloxy)phenyl)ethane.

In the resist composition of the invention, an appropriate amount of the dissolution inhibitor is up to 20 parts, and especially up to 15 parts by weight per 100 parts by weight of the solids in the resist composition. With more than 20 parts of the dissolution inhibitor, the resist composition becomes less heat resistant because of an increased content of monomer components.

Component (H)

To a chemical amplification, negative working, resist composition as well, the photoacid generator in the form of an O-arylsulfonyloxime compound capable of generating an acid of formula (1') upon exposure to radiation or the photoacid generators of formulae (1), (1a), (1b) and (1c) according to the invention are applicable. This composition further contains an alkali-soluble resin as component (H), examples of which are intermediates of the above-described component (A) though not limited thereto. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxy-styrene), partially hydrogenated p-hydroxystyrene copolymers, p-hydroxystyrene-α-methyl-p-hydroxystyrene copolymers, p-hydroxystyrene-α-methylstyrene copolymers, p-hydroxy-styrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers.

Alkali-soluble resins comprising units of the following formula (2), (2'), (2") or (2''') are especially preferred.

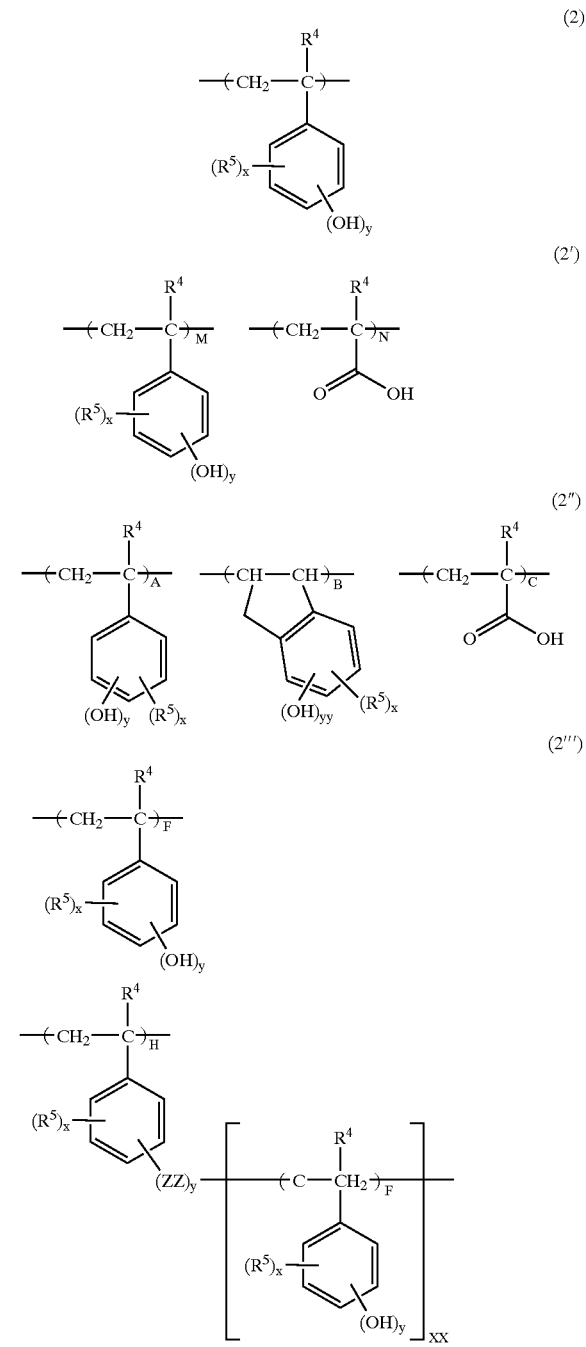

Herein $R^4$ is hydrogen or methyl; and $R^5$ is a straight, branched or cyclic alkyl group of 1 to 8 carbon atoms. The subscript x is 0 or a positive integer; y is a positive integer, satisfying $x+y \leq 5$, yy is 0 or a positive integer, satisfying x+yy≦4; M and N are positive integers, satisfying 0<N/(M+N)≦0.5; A and B are positive integers, C is 0 or a positive integer, satisfying 0<B/(A+B+C)≦0.5, ZZ is a divalent group selected from among $CH_2$, CH(OH), $CR^5$(OH), C=O and $C(OR^5)$(OH), or a trivalent organic group represented by —C(OH)=; F is independently a positive integer, and H is a positive integer, satisfying 0.001≦H/(H+F)≦0.1; and XX is 1 or 2.

The polymer should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

To impart a certain function, suitable substituent groups may be introduced into some of the phenolic hydroxyl and carboxyl groups on the foregoing polymer. Exemplary and preferred are substituent groups for improving adhesion to the substrate, substituent groups for improving etching resistance, and especially substituent groups which are relatively stable to acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxoranyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as t-butoxycarbonyl and relatively acid-undecomposable substituent groups such as t-butyl and t-butoxycarbonylmethyl.

In the resist composition, the above resin is blended in any desired amount, preferably of 65 to 99 parts by weight, especially 65 to 98 parts by weight per 100 parts by weight of the solids.

Also contained in the negative resist composition is (I) an acid crosslinking agent capable of forming a crosslinked structure under the action of an acid. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified, negative resist composition of the invention. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred acid crosslinking agents are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

An appropriate amount of the acid crosslinking agent is, but not limited thereto, about 1 to 20 parts, and especially about 5 to 15 parts by weight per 100 parts by weight of the solids in the resist composition. The acid crosslinking agents may be used alone or in admixture of any.

Component (J) is an alkali-soluble compound having a molecular weight of up to 2,500. Any suitable compound may be used although a compound having at least two phenol and/or carboxyl groups is preferred. Illustrative, non-limiting, examples of the alkali-soluble compound (J) include cresol, catechol, resorcinol, pyrogallol, fluoroglycin, bis(4-hydroxyphenyl)methane, 2,2-bis(4'-hydroxyphenyl)propane, bis(4-hydroxyphenyl)sulfone, 1,1,1-tris(4'-hydroxyphenyl)-ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)-propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenyl-acetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more. The alkali-soluble compound is blended in any desired amount, preferably of 0 to 20 parts by weight, especially 2 to 10 parts by weight per 100 parts by weight of the solids in the resist composition.

In the chemical amplification type resist composition according to the invention, there may be added such additives as a surfactant for improving coating, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products Co., Ltd.), Megaface F171, F172 and F173 (Dai-Nippon Ink & Chemicals, Inc.), Florade FC430 and FC431 (Sumitomo 3M Co., Ltd.), Aashiguard AG710, Surflon S-381, S-382, SCIO, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

In the chemically amplified resist composition according to the invention, the surfactant is preferably formulated in an amount of up to 2 parts, and especially up to 1 part by weight, per 100 parts by weight of the solids in the resist composition.

In the chemically amplified resist composition according to the invention, a UV absorber may be added. Those UV absorbers described in JP-A 11-190904 are useful, but the invention is not limited thereto. Exemplary UV absorbers are diaryl sulfoxide derivatives such as bis(4-hydroxyphenyl)sulfoxide, bis(4-tert-butoxyphenyl) sulfoxide, bis(4-tert-butoxycarbonyloxyphenyl) sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazide group-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate. The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemically amplified resist composition comprising the photoacid generator in the form of an O-arylsulfonyloxime compound capable of generating an acid of formula (1') upon exposure to radiation or the photoacid generators of formulae (1), (1a), (1b) and (1c) according to the invention.

The composition is applied onto a substrate (e.g., Si, $SiO_2$, SiN, SiON, TiN, WSi, BPSG, SOG, organic anti-reflecting film, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 120° C. for 1 to 5 minutes. The resulting resist film is generally 0.1 to 2.0 μm thick. With a mask having a desired pattern placed above the resist film, the resist film is then exposed to radiation, preferably having an exposure wavelength of up to 300 nm, such as UV, deep-UV, electron beams, x-rays, excimer laser light, γ-rays and synchrotron radiation. The preferred light source is a beam from an excimer laser, especially KrF excimer laser or deep UV of 245–255 nm wavelength. The exposure dose is preferably in the range of about 1 to 200 $mJ/cm^2$, more preferably about 10 to 100 $mJ/cm^2$. The film is further baked on a hot plate at 60 to 150° C. for 1 to 5 minutes, preferably 80 to 120° C. for 1 to 3 minutes (post-exposure baking= PEB).

Thereafter the resist film is developed with a developer in the form of an aqueous base solution, for example, 0.1 to 5%, preferably 2 to 3% aqueous solution of tetramethylammonium hydroxide (TMAH) for 0.1 to 3 minutes, preferably 0.5 to 2 minutes by conventional techniques such as dipping, puddling or spraying. In this way, a desired resist pattern is formed on the substrate. It is appreciated that the resist composition of the invention is best suited for micropatterning using such actinic radiation as deep UV with a wavelength of 254 to 193 nm, vacuum UV with a wavelength of 157 nm, electron beams, x-rays, excimer laser light, γ-rays and synchrotron radiation. With any of the above-described parameters outside the above-described range, the process may sometimes fail to produce the desired pattern.

EXAMPLE

Examples of the invention are given below by way of illustration and not by way of limitation.

Synthesis Example 1
Synthesis of Sodium 4-(4'-methylphenylsulfonyloxy) benzenesulfonate In 400 g of tetrahydrofuran and 250 g of water were dissolved 208 g (1.0 mol) of 4-phenolsulfonic acid hydrate and 191 g (1.0 mol) of p-toluenesulfonic acid chloride. With ice cooling and stirring, an aqueous sodium hydroxide solution (80 g (2.0 mol) of sodium hydroxide in 125 g of water) was added dropwise such that the temperature might not exceed 20° C. After the completion of dropwise addition, the solution was allowed to ripen for 2 hours at room temperature. To the reaction solution, 700 g of dichloromethane was added to help sodium 4-(4'-methylphenylsulfonyloxy)benzenesulfonate crystallize. The crystals were collected by filtration, washed with 200 g of dichloromethane, and dried in vacuum at 60° C. for 12 hours. The amount was 330 g (yield 94%).

Synthesis Example 2
Synthesis of Sodium 2,5-bis(4'-methylphenylsulfonyloxy)-benzenesulfonate By substantially following Synthesis Example 1 except that 1.0 mol of potassium hydroquinonesulfonate was used instead of the phenolsulfonic acid and 2.5 mol of p-toluenesulfonic acid chloride was used, the end compound, sodium 2,5-bis(4'-methylphenylsulfonyloxy) benzenesulfonate was synthesized.

Synthesis Example 3
Synthesis of Sodium 6-(4'-methylphenylsulfonyloxy)-naphthalene-2-sulfonate In 100 g of tetrahydrofuran and 80 g of water were dissolved 50 g (0.18 mol) of sodium 2,6-naphtholsulfonate hydrate and 33.8 g (0.18 mol) of p-toluenesulfonic acid chloride. With ice cooling and stirring, an aqueous sodium hydroxide solution (7.1 g (0.18 mol) of sodium hydroxide in 30 g of water) was added dropwise such that the temperature might not exceed 20° C. After the completion of dropwise addition, the solution was allowed to ripen for 2 hours at room temperature. To the reaction solution, 600 g of dichloromethane was added to help sodium 6-(4'-methylphenyl-sulfonyloxy)naphthalene-2-sulfonate crystallize. The crystals were collected by filtration, washed with 300 g of dichloromethane, and dried in vacuum at 60° C. for 12 hours. The amount was 62 g (yield 86%).

Synthesis Example 4
Synthesis of Sodium 4-(4'-methylphenylsulfonyloxy)-naphthalene-1-sulfonate In 59 g of tetrahydrofuran and 23 g of water were dissolved 25 g (0.09 mol) of sodium 1,4-naphtholsulfonate hydrate and 16.8 g (0.09 mol) of p-toluenesulfonic acid chloride. With ice cooling and stirring, an aqueous sodium hydroxide solution (3.5 g (0.09 mol) of sodium hydroxide in 27 g of water) was added dropwise such that the temperature might not exceed 20° C. After the completion of dropwise addition, the solution was allowed to ripen for 2 hours at room temperature. To the reaction solution, 700 g of dichloromethane was added to help sodium 4-(4'-methylphenyl-sulfonyloxy)naphthalene-1-sulfonate crystallize. The crystals were collected by filtration, washed with 300 g of dichloromethane, and dried in vacuum at 60° C. for 12 hours. The amount was 30 g (yield 83%).

Synthesis Example 5
Synthesis of Sodium 8-(4'-methylphenylsulfonyloxy)-naphthalene-1-sulfonate In 24 g of tetrahydrofuran and 11 g of water were dissolved 12.3 g (0.05 mol) of sodium 1,8-naphtholsulfonate hydrate and 9.5 g (0.05 mol) of p-toluenesulfonic acid chloride. With ice cooling and stirring, an aqueous sodium hydroxide solution (2 g (0.05 mol) of sodium hydroxide in 9 g of water) was added dropwise such that the temperature might not exceed 20° C. After the completion of dropwise addition, the solution was allowed to ripen for 2 hours at room temperature. To the reaction solution, 100 g of dichloromethane was added to help sodium 8-(4'-methylphenyl-sulfonyloxy)naphthalene-1-sulfonate crystallize. The crystals were collected by filtration, washed with 300 g of dichloromethane, and dried in vacuum at 60° C. for 12 hours. The amount was 17 g (yield 85%).

Synthesis Example 6
Synthesis of Sodium 3-methoxy-4-(4'-methylphenylsulfonyloxy)-benzenesulfonate In 80 g of tetrahydrofuran and 65 g of water were dissolved 50 g (0.2 mol) of potassium guaiacolsulfonate hydrate and 38 g (0.2 mol) of p-toluenesulfonic acid chloride. With ice cooling and stirring, an aqueous sodium hydroxide solution (8 g (0.2 mol) of sodium hydroxide in 15 g of water) was added dropwise such that the temperature might not exceed 20° C. After the completion of dropwise addition, the solution was allowed to ripen for 2 hours at room temperature. To the reaction solution, 200 g of dichloromethane was added to help sodium 3-methoxy-4-(4'-methylphenylsulfonyloxy)-benzenesulfonate crystallize. The crystals were collected by filtration, washed with 200 g of dichloromethane, and dried in vacuum at 60° C. for 12 hours. The amount was 72 g (yield 94% as Na salt).

It is noted that the crystalline product thus obtained could be a mixture of sodium and potassium salts. The product was directly used in the subsequent step of halogenation reaction without purification because the metals can be removed as sodium and potassium ions in the halogenation reaction.

Synthesis Example 7
Synthesis of 4-(4'-methylphenylsulfonyloxy) benzenesulfonyl Chloride In 80 g of carbon tetrachloride, 20 g (0.057 mol) of sodium 4-(4'-methylphenylsulfonyloxy)benzenesulfonate, obtained in Synthesis Example 1, was dispersed by stirring under ice cooling. To the suspension, 23.8 g (0.114 mol) of phosphorus pentachloride was slowly added such that the temperature might not exceed 20° C. The suspension was stirred for one hour under ice cooling and then for 12 hours at room temperature. After the ripening, the reaction solution was poured into 150 g of ice water whereupon a white oily matter separated out. The oily matter was extracted with 100 g of dichloromethane, dried over anhydrous magnesium sulfate, and filtered. The solvent was distilled off in vacuum, yielding 15.9 g of white crystals (yield 81%).

Synthesis Examples 8–13

The procedure of Synthesis Example 7 was repeated aside from using the arylsulfonyloxyarylsulfonic acid salts of Synthesis Examples 2 to 6 instead of the sodium 4-(4'-methylphenylsulfonyloxy)benzenesulfonate used in Synthesis Example 7. The corresponding sulfonyl chlorides were accordingly synthesized.

Synthesis Example 8

02,5-bis(4'-methylphenylsulfonyloxy)benzenesulfonyl chloride

Synthesis Example 9

6-(4'-methylphenylsulfonyloxy)naphthalene-2-sulfonyl chloride

Synthesis Example 10

4-(4'-methylphenylsulfonyloxy)naphthalene-1-sulfonyl chloride

Synthesis Example 11

8-(4'-methylphenylsulfonyloxy)naphthalene-1-sulfonyl chloride

Synthesis Example 12

3-methoxy-4-(4'-methylphenylsulfonyloxy) benzenesulfonyl chloride

Synthesis Example 13

3-methyl-4-(4'-methylphenylsulfonyloxy)benzenesulfonyl chloride

Synthesis Example 14
Synthesis of (5-(4-(4-methylphenylsulfonyloxy)phenyl-sulfonyloxy)imino-5H-thiophen-2-ylidene)-(2-methylphenyl)-acetonitrile The end compound was obtained by reacting (5-hydroxy-imino-5H-thiophen-2-ylidene)-(2-methylphenyl)-acetonitrile with 4-(4'-methylphenylsulfonyloxy) benzenesulfonyl chloride of Synthesis Example 7 as described in U.S. Pat. No. 6,004,724. The compound thus obtained was analyzed by nuclear magnetic resonance (NMR) spectroscopy and infrared (IR) absorption spectroscopy, with the results shown below. Although the compound obtained could be either of or a mixture of two isomers of the structure shown below, it was judged from the spectra that the product was either one single compound.

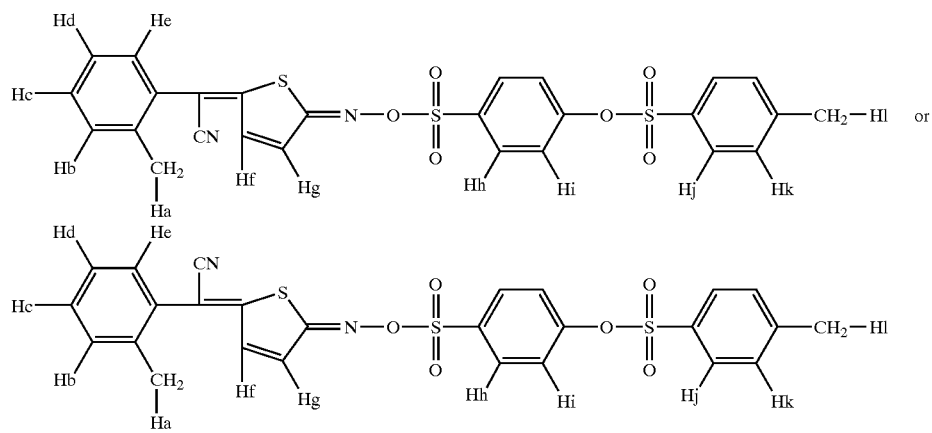

¹H-NMR: CDCl₃ (ppm)
2.32 (3H, s, Ha)
2.46 (3H, s, Hl)
6.09–6.11 (1H, d, Hg or Hf)
6.78–6.80 (1H, d, Hf or Hg)
7.15–7.38 (8H, m, Hi, Hk, Hb, Hc, Hd, He)
7.71–7.73 (2H, d, Hj)
8.15–8.18 (2H, d, Hh)
IR: cm⁻¹ 2202, 1733, 1587, 1525, 1487, 1456, 1405, 1383, 1296, 1261, 1236, 1195, 1178, 1157, 1120, 1092, 1041, 1016, 852, 816, 793, 754, 731, 706, 677, 650, 625, 609, 586, 563, 549, 444

Synthesis Example 15
Synthesis of 2,2,2-trifluoro-1-(4-(3-(4-(2,2,2-trifluoro-1-(4-(4-methylphenylsulfonyloxy)phenylsulfonyloxyimino)-ethyl)-phenoxy)-propoxy)-phenyl)ethanonoxime(4-(4-methylphenyl-sulfonyloxy)phenylsulfonate)

The end compound was synthesized from the corresponding oxime compound and 4-(4'-methylphenyl-sulfonyloxy)benzenesulfonyl chloride obtained in Synthesis Example 7, by the process described in JP-A 2000-314956. The compound thus obtained was analyzed by NMR spectroscopy and IR absorption spectroscopy, with the results shown below.

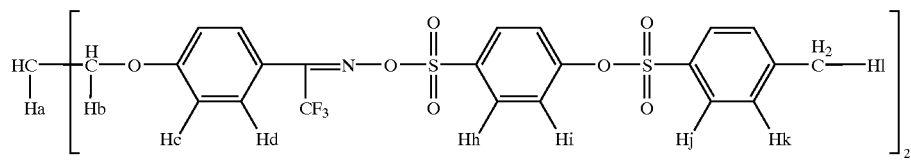

¹H-NMR: CDCl₃ (ppm)
2.27–2.36 (2H, m, Ha)
2.46 (6H, s, Hl)
4.20–4.24 (4H, t, Hb)
6.96–6.99 (4H, d, Hc)
7.20–7.23 (4H, d, Hi)
7.32–7.35 (4H, d, Hk)
7.42–7.45 (4H, d, Hj)
7.70–7.73 (4H, d, Hd)
7.93–7.96 (4H, d, Hh)

IR: cm⁻¹ 1735, 1604, 1512, 1489, 1473, 1387, 1342, 1296, 1259, 1199, 1178, 1157, 1092, 1055, 1018, 999, 889, 862, 814, 802, 773, 756, 737, 704, 669, 678, 627, 588, 565, 549, 518

Synthesis Example 16
Synthesis of bis(O-4-(4-methylphenylsulfonyloxy)phenylsulfonyl)dimethylglyoxime The end compound was synthesized from dimethylglyoxime and 4-(4'-methylphenylsulfonyloxy)benzenesulfonyl chloride obtained in Synthesis Example 7, by the process described in Japanese Patent 2,906,999. The compound thus obtained was analyzed by NMR spectroscopy and IR absorption spectroscopy, with the results shown below.

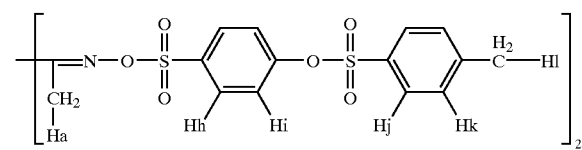

¹H-NMR: CDCl₃ (ppm)
2.03 (6H, s, Ha)
2.46 (6H, s, Hl)
7.18–7.21 (4H, d, Hi)
7.32–7.35 (4H, d, Hk)
7.70–7.73 (4H, d, Hj)
7.89–7.92 (4H, d, Hh)
IR: cm⁻¹ 1587, 1487, 1406, 1381, 1296, 1196, 1182, 1157, 1105, 1093, 1016, 864, 854, 822, 746, 675, 654, 634, 582, 567, 549

Synthesis Examples 17–34
The end compounds were synthesized by following the procedures of Synthesis Examples 14 to 16 except that the sulfonyl chlorides obtained in Synthesis Examples 8 to 13 were used instead of the 4-(4'-methylphenylsulfonyloxy)-benzenesulfonyl chloride used in Synthesis Examples 14 to 16.

Synthesis Example 17

(5-(2,5-bis(4-methylphenylsulfonyloxy)benzene-sulfonyloxy)imino-5H-thiophen-2-ylidene)-(2-methyl-phenyl)-acetonitrile

Synthesis Example 18

2,2,2-trifluoro-1-(4-(3-(4-(2,2,2-trifluoro-1-(2,5-bis(4-methylphenylsulfonyloxy)benzenesulfonyloxy)phenyl-sulfonyloxyimino)-ethyl)-phenoxy)-propoxy)-phenyl)-ethanonoxime(2,5-bis(4-methylphenylsulfonyloxy) benzene-sulfonyloxy)phenylsulfonate)

Synthesis Example 19 bis(O-2,5-bis(4-methylphenylsulfonyloxy)benzene-sulfonyl)dimethylglyoxime

Synthesis Example 20

(5-(6-(4-methylphenylsulfonyloxy)naphthalene-2-sulfonyloxy)imino-5H-thiophen-2-ylidene)-(2-methyl-phenyl)-acetonitrile

Synthesis Example 21

2,2,2-trifluoro-1-(4-(3-(4-(2,2,2-trifluoro-1-(6-(4-methylphenylsulfonyloxy)naphthalene-2-sulfonyloxy)-phenylsulfonyloxyimino)-ethyl)-phenoxy)-propoxy)-phenyl)ethanonoxime(6-(4-methylphenylsulfonyloxy)-naphthalene-2-sulfonyloxy)phenylsulfonate)

Synthesis Example 22 bis(O-6-(4-methylphenylsulfonyloxy)naphthalene-2-sulfonyl)dimethylglyoxime

Synthesis Example 23

(5-(4-(4-methylphenylsulfonyloxy)naphthalene-1-sulfonyloxy)imino-5H-thiophen-2-ylidene)-(2-methyl-phenyl)-acetonitrile

Synthesis Example 24

2,2,2-trifluoro-1-(4-(3-(4-(2,2,2-trifluoro-1-(4-(4-methylphenylsulfonyloxy)naphthalene-1-sulfonyloxy)-phenylsulfonyloxyimino)-ethyl)-phenoxy)-propoxy) phenyl)-ethanonoxime(4-(4-methylphenylsulfonyloxy) naphthalene-1-sulfonyloxy)phenylsulfonate)

Synthesis Example 25 bis(O-4-(4-methylphenylsulfonyloxy)naphthalene-1-sulfonyl)dimethylglyoxime

Synthesis Example 26

(5-(8-(4-methylphenylsulfonyloxy)naphthalene-1-sulfonyloxy)imino-5H-thiophen-2-ylidene)-(2-methyl-phenyl)-acetonitrile

Synthesis Example 27

2,2,2-trifluoro-1-(4-(3-(4-(2,2,2-trifluoro-1-(8-(4-methylphenylsulfonyloxy)naphthalene-1-sulfonyloxy)-phenylsulfonyloxyimino)-ethyl)-phenoxy)-propoxy)-phenyl)ethanonoxime(4-(4-methylphenylsulfonyloxy)-naphthalene-1-sulfonyloxy)phenylsulfonate)

Synthesis Example 28 bis(O-8-(4-methylphenylsulfonyloxy)naphthalene-1-sulfonyl)dimethylglyoxime

Synthesis Example 29

(5-(3-methoxy-4-(4-methylphenylsulfonyloxy)benzene-sulfonyloxy)imino-5H-thiophen-2-ylidene)-(2-methyl-phenyl)-acetonitrile

Synthesis Example 30

2,2,2-trifluoro-1-(4-(3-(4-(2,2,2-trifluoro-1-(3-methoxy-4-(4-methylphenylsulfonyloxy)benzene-sulfonyloxy) phenylsulfonyloxyimino)-ethyl)-phenoxy)-propoxy)-phenyl)ethanonoxime(3-methoxy-4-(4-methyl-phenylsulfonyloxy)benzenesulfonyloxy)phenylsulfonate

Synthesis Example 31 bis(O-3-methoxy-4-(4-methylphenylsulfonyloxy)benzene-sulfonyl)dimethylglyoxime

Synthesis Example 32

(5-(3-methyl-4-(4-methylphenylsulfonyloxy) benzenesulfonyloxy)imino-5H-thiophen-2-ylidene)-(2-methyl-phenyl)-acetonitrile

Synthesis Example 33

2,2,2-trifluoro-1-(4-(3-(4-(2,2,2-trifluoro-1-(3-methyl-4-(4-methylphenylsulfonyloxy)benzenesulfonyloxy)phenyl-sulfonyloxyimino)-ethyl)-phenoxy)-propoxy)-phenyl)-ethanonoxime(3-methyl-4-(4-methylphenylsulfonyloxy)-benzenesulfonyloxy)phenylsulfonate)

Synthesis Example 34 bis(O-3-methyl-4-(4-methylphenylsulfonyloxy)benzene-sulfonyl)dimethylglyoxime

Synthesis Example 35

Synthesis of 2-(4-(4-methylphenylsulfonyloxy) phenylsulfonyl-oxyimino)-2-phenylacetonitrile In 11 g of tetrahydrofuran were dissolved 1.46 g (0.01 mol) of 2-hydroxyimino-2-phenylacetonitrile, available from Aldrich Chemical Company, Inc., and 3.47 g (0.01 mol) of 4-(4-methylphenylsulfonyloxy)benzenesulfonyl chloride, prepared in Synthesis Example 7. At room temperature, 1.01 g (1.46 ml, 0.01 mol) of triethylamine was added dropwise to the solution, which was stirred for one hour at room temperature. Water, 30 g, was added to the reaction solution whereupon the organic layer was separated. To the organic layer, 30 g of dichloromethane and 25 g of water were added whereby the organic layer was washed. The organic layer was concentrated in a rotary evaporator. Methanol, 22 g, was added to 8 g of the concentrate for recrystallization. The crystals were filtered and dried, yielding 3.7 g (yield 81%) of the end compound, 2-(4-(4-methylphenylsulfonyloxy)phenyl-sulfonyloxy-imino)-2-phenylacetonitrile. The compound thus obtained was analyzed by NMR spectroscopy and IR absorption spectroscopy, with the results shown below.

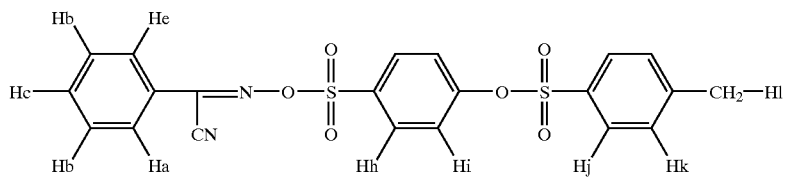

¹H-NMR: CDCl₃ (ppm)
7.77–7.80 (2H, d, Ha)
7.46–7.51 (2H, t, Hb)
7.57–7.62 (1H, t, Hc)
8.00–8.04 (2H, d, Hh)
7.24–7.27 (2H, d, Hi)
7.69–7.72 (2H, d, Hj)
7.30–7.33 (2H, d, Hk)
2.45 (3H, s, Hl)
IR: cm⁻¹ 1597, 1589, 1485, 1448, 1394, 1385, 1323, 1306, 1200, 1186, 1178, 1159, 1107, 1092, 891, 858, 852, 843, 831, 824, 771, 754, 729, 704, 687, 677, 656, 640, 629, 590, 563, 549, 526

Examples 1–24 and Comparative Examples 1–3

Resist materials were prepared in accordance with the formulation shown in Tables 1 to 3. The components used are shown below.

Polymer A: poly(p-hydroxystyrene) in which hydroxyl groups are protected with 15 mol % of 1-ethoxyethyl groups and 15 mol % of tert-butoxycarbonyl groups, having a weight average molecular weight of 12,000.

Polymer B: poly(p-hydroxystyrene) in which hydroxyl groups are protected with 30 mol % of 1-ethoxyethyl groups, having a weight average molecular weight of 12,000.

Polymer C: poly(p-hydroxystyrene) in which hydroxyl groups are protected with 15 mol % of 1-ethoxyethyl groups and 10 mol % of tert-butoxycarbonyl groups, having a weight average molecular weight of 11,000.

Polymer D: poly(p-hydroxystyrene) in which hydroxyl groups are protected with 25 mol % of 1-ethoxyethyl groups and crosslinked with 3 mol % of 1,2-propanediol divinyl ether, having a weight average molecular weight of 13,000.

Polymer E: poly(p-hydroxystyrene) in which hydroxyl groups are protected with 25 mol % of tert-butoxycarbonyl groups, having a weight average molecular weight of 12,000.

Polymer F: p-hydroxystyrene/2-ethyl-2-adamantyl acrylate copolymer having a compositional ratio (molar ratio) of 70:30 and a weight average molecular weight of 15,000.

Polymer G: p-hydroxystyrene/1-ethyl-1-norbornene methacrylate copolymer having a compositional ratio (molar ratio) of 70:30 and a weight average molecular weight of 15,000.

Polymer H: p-hydroxystyrene/tert-butyl acrylate copolymer having a compositional ratio (molar ratio) of 65:35 and a weight average molecular weight of 15,000.

Polymer I: p-hydroxystyrene/1-ethylcyclopentyl methacrylate copolymer having a compositional ratio (molar ratio) of 65:35 and a weight average molecular weight of 15,000.

Polymer J: p-hydroxystyrene/1-ethylcyclopentyl methacrylate/styrene copolymer having a compositional ratio (molar ratio) of 65:10:25 and a weight average molecular weight of 12,000.

Polymer K: p-hydroxystyrene/indene copolymer having a compositional ratio (molar ratio) of 80:20 in which hydroxyl groups on hydroxystyrene are protected with 20 mol % of tert-butoxycarbonyl groups, having a weight average molecular weight of 10,000.

Polymer L: p-hydroxystyrene/indene/1-ethyl-1-norbornene methacrylate copolymer having a compositional ratio (molar ratio) of 70:10:20 and a weight average molecular weight of 10,000.

Polymer M: p-hydroxystyrene/indene/1-ethyl-1-norbornene methacrylate copolymer having a compositional ratio (molar ratio) of 70:15:15 and a weight average molecular weight of 10,000.

Polymer N: poly(p-hydroxystyrene) in which hydroxyl groups are protected with 8 mol % of acetyl groups, having a weight average molecular weight of 8,000.

PAG1: compound of Synthesis Example 14
PAG2: compound of Synthesis Example 15
PAG3: compound of Synthesis Example 16
PAG4: triphenylsulfonium 4-(4-methylphenyl)sulfonyloxy-benzenesulfonate
PAG5: (4-tert-butoxyphenyl)diphenylsulfonium 10-camphor-sulfonate
PAG6: bis(cyclohexylsulfonyl)diazomethane
PAG7: bis(2,4-dimethylphenylsulfonyl)diazomethane
PAG8: (5-(10-camphorsulfonyloxy)imino-5H-thiophen-2-ylidene)-(2-methylphenyl)-acetonitrile
PAG9: (5-(4-methylphenylsulfonyloxy)imino-5H-thiphen-2-ylidene)-(2-methylphenyl)-acetonitrile
Crosslinker: 1,3,5,7-tetramethoxymethylglycoluril
Dissolution inhibitor: bis(4-(2'-tetrahydropyranyloxy)-phenyl)methane
Basic compound A: tri-n-butylamine
Basic compound B: tris(2-methoxyethyl)amine
Organic acid derivative A: 4,4-bis(4'-hydroxyphenyl)valeric acid
Organic acid derivative B: salicylic acid
Surfactant A: FC-430 (Sumitomo 3M Co., Ltd.)
Surfactant B: Surflon S-381 (Asahi Glass Co., Ltd.)
UV absorber: 9,10-dimethylanthracene
Solvent A: propylene glycol methyl ether acetate
Solvent B: ethyl lactate The resist materials thus obtained were each filtered through a 0.2-μm Teflon® filter, thereby giving resist solutions. These resist solutions were spin-coated onto silicon wafers having an organic antireflection film (Brewer Science, DUV-44) of 800 Å thick coated thereon, so as to give a dry thickness of 0.6 μm. For the coating and subsequent baking and developing steps, a coater/developer Clean Track Mark 8 by Tokyo Electron Co., Ltd. was used.

The coated wafer was then baked on a hot plate at 100° C. for 90 seconds. The resist films were exposed to ⅔ annular illumination using an excimer laser stepper NSR—S202A (Nikon Corp., NA 0.6), then baked (PEB) at 110° C. for 90 seconds, and developed with a solution of 2.38% tetramethylammonium hydroxide in water, thereby giving positive patterns (Examples 1 to 23 and Comparative Examples 1–3) or negative pattern (Example 24).

The resulting resist patterns were evaluated as described below.

Resist Pattern Evaluation

The optimum exposure dose (sensitivity Eop) was the exposure dose which provided a 1:1 resolution at the top and bottom of a 0.18-μm line-and-space pattern. The minimum line width (μm) of a line-and-space pattern which was ascertained separate at this dose was the resolution of a test resist. The shape in cross section of the resolved resist pattern was examined under a scanning electron microscope. The depth of focus (DOF) was determined by offsetting the focal point and judging the resist to be satisfactory when the resist pattern shape was kept rectangular and the resist pattern film thickness was kept above 80% of that at accurate focusing.

The PED stability of a resist was evaluated by effecting post-exposure bake (PED) after 24 hours of holding from exposure at the optimum dose and determining a variation in line width (or groove width for the negative resist). The less the variation, the greater is the PED stability.

The results of resist pattern evaluation are shown in Table 4.

Other Evaluation

The solubility of resist material in a solvent mixture was examined by visual observation and in terms of clogging upon filtration.

With respect to the applicability of a resist solution, uneven coating was visually observed. Additionally, using a film gage Clean Lambda Ace VM-3010 (optical interference film gage by Dainippon Screen Mfg. Co., Ltd.), the thickness of a resist film on a common wafer was measured at different positions, based on which a variation from the desired coating thickness (0.6 μm) was calculated. The applicability was rated "good" when the variation was within 0.5% (that is, within 0.003 μm), "unacceptable" when the variation was from more than 0.5% to 1%, and "poor" when the variation was more than 1%.

Storage stability was judged in terms of foreign matter precipitation or sensitivity change with the passage of time. After the resist solution was aged for 100 days at the longest, the number of particles of greater than 0.3 μm per ml of the resist solution was counted by means of a particle counter KL-20A (Rion Co., Ltd.), and the foreign matter precipitation was determined "good" when the number of particles is not more than 5. Also, the sensitivity change was rated "good" when a change with time of sensitivity (Eop) was within 5% from that immediately after preparation, and "poor" when the change is more than 5%.

Debris appearing on the developed pattern was observed under a scanning electron microscope (TDSEM) model S-7280H (Hitachi, Ltd.). The resist film was rated "good" when the number of foreign particles was up to 10 per 100 μm$^2$, "unacceptable" when from 11 to 15, and "poor" when more than 15.

Debris left after resist peeling was examined using a surface scanner Surf-Scan 6220 (Tencol Instruments). A resist-coated 8-inch wafer was subjected to entire exposure rather than patterned exposure, processed in a conventional manner, and developed with a 2.38% TMAH solution before the resist film was peeled off (only the resist film in the exposed area was peeled). After the resist film was peeled, the wafer was examined and rated "good" when the number of foreign particles of greater than 0.20 μm was up to 100, "unacceptable" when from 101 to 150, and "poor" when more than 150.

The results are shown in Table 5.

TABLE 1

| Composition (pbw) | Example |  |  |  |  |  |  |  |  |  |  |  |
|---|---|---|---|---|---|---|---|---|---|---|---|---|
|  | 1 | 2 | 3 | 4 | 5 | 6 | 7 | 8 | 9 | 10 | 11 | 12 |
| Polymer A | 80 |  |  |  |  |  |  |  |  |  |  | 40 |
| Polymer B |  | 80 |  |  |  |  |  |  |  |  |  |  |
| Polymer C |  |  | 80 |  |  |  |  |  |  |  |  |  |
| Polymer D |  |  |  | 80 |  |  |  |  |  |  |  |  |
| Polymer E |  |  |  |  | 80 |  |  |  |  |  |  |  |
| Polymer F |  |  |  |  |  | 80 |  |  |  |  |  |  |
| Polymer G |  |  |  |  |  |  | 80 |  |  |  |  |  |
| Polymer H |  |  |  |  |  |  |  | 80 |  |  |  |  |
| Polymer I |  |  |  |  |  |  |  |  | 80 |  |  |  |
| Polymer J |  |  |  |  |  |  |  |  |  | 80 |  |  |
| Polymer K |  |  |  |  |  |  |  |  |  |  | 80 |  |
| Polymer L |  |  |  |  |  |  |  |  |  |  |  | 80 |
| Polymer M |  |  |  |  |  |  |  |  |  |  |  |  |
| Polymer N |  |  |  |  |  |  |  |  |  |  |  |  |
| PAG1 | 1 | 1 |  |  | 1 | 1 |  | 1 |  | 1 |  |  |
| PAG2 |  |  | 3 |  |  | 1 | 3 |  | 3 |  | 1 |  |
| PAG3 |  |  |  | 3 |  |  |  | 1 |  |  | 3 | 3 |
| PAG4 | 1 |  |  | 1 |  |  |  |  |  |  |  |  |
| PAG5 |  | 1 |  |  | 1 |  | 1 |  |  | 1 |  | 1 |
| PAG6 | 1 |  |  |  |  | 2 |  |  |  |  |  |  |
| PAG7 |  |  |  |  |  |  |  |  | 1 |  |  |  |
| PAG8 |  |  | 1 |  |  |  |  |  |  |  |  |  |
| PAG9 |  |  |  |  | 1 |  |  |  |  |  |  |  |
| Dissolution inhibitor |  |  |  |  |  |  |  |  |  |  |  |  |
| Basic compound A |  | 0.3 |  | 0.3 | 0.3 | 0.3 |  | 0.3 | 0.3 | 0.15 | 0.3 | 0.3 |
| Basic compound B | 0.3 |  | 0.3 |  |  |  | 0.3 |  |  | 0.15 |  |  |
| Organic acid derivative A |  |  | 0.5 |  |  |  |  |  | 0.5 |  |  |  |
| Organic acid derivative B |  |  |  |  |  |  |  |  |  |  |  |  |

TABLE 1-continued

| Composition (pbw) | Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Surfactant A | 0.25 | 0.25 | 0.25 | 0.25 | | | | | | | 0.25 | 0.25 |
| Surfactant B | | | | | 0.25 | 0.25 | 0.25 | 0.25 | 0.25 | 0.25 | | |
| UV absorber | | | | | | | | | | | | |
| Solvent A | 385 | 385 | 385 | 280 | 385 | 385 | 385 | 385 | 385 | 280 | 382 | 385 |
| Solvent B | | | | 105 | | | | | | 105 | | |

TABLE 2

| Composition (pbw) | Example | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| Polymer A | | | 40 | | 60 | | | | | | | |
| Polymer B | | | | | | | | 60 | | | 75 | |
| Polymer C | | | | | | 40 | | | 40 | | | |
| Polymer D | | 70 | 40 | 60 | | 40 | | | | | | |
| Polymer E | | | | | | | 40 | | | 10 | | |
| Polymer F | | | | | | | | | | | | |
| Polymer G | | | | | | | 40 | | | | | |
| Polymer H | | | | | | | | | | | | |
| Polymer I | | 10 | | | | | | 20 | | | | |
| Polymer J | | | | | | | | | | | | |
| Polymer K | | | | | | | | | 40 | | | |
| Polymer L | 40 | | | | 20 | | | | | 70 | | |
| Polymer M | 40 | | | 20 | | | | | | | | |
| Polymer N | | | | | | | | | | | | 80 |
| PAG1 | | | | | 1 | 1 | | | 1 | | | 1 |
| PAG2 | | 2 | 3 | 3 | | | 3 | 2 | | 2 | | |
| PAG3 | 1 | | | | | 1 | | 1 | | | 2 | |
| PAG4 | | | 1 | | | | | 2 | | 2 | 2 | |
| PAG5 | 2 | 2 | | | 1 | 1 | | | | | | 2 |
| PAG6 | | | | 2 | | | | 2 | | | | |
| PAG7 | | 1.5 | | | | | 1.5 | | | | | |
| PAG8 | | | 1 | | | | | 1 | | | | |
| PAG9 | | | | | | | | | | | | |
| Crosslinker | | | | | | | | | | | | 15 |
| Dissolution inhibitor | | | | | | | | | | | 5 | |
| Basic compound A | 0.3 | | | | | | 0.3 | 0.3 | 0.3 | 0.15 | | |
| Basic compound B | | 0.3 | 0.3 | 0.3 | 0.3 | 0.3 | | | | 0.15 | 0.3 | |
| Organic acid derivative A | | | | | 0.5 | | | | | | | 0.3 |
| Organic acid derivative B | | | | | | 0.25 | | | | | | |
| Surfactant A | 0.25 | | 0.25 | 0.25 | 0.25 | | | | 0.25 | 0.25 | 0.25 | 0.25 |
| Surfactant B | | 0.25 | | | | 0.25 | | 0.25 | | | | |
| UV absorber | | | | | 0.5 | | | | | | | |
| Solvent A | 385 | 385 | 385 | 280 | 280 | 385 | 280 | 385 | 385 | 385 | 280 | 385 |
| Solvent B | | | | 105 | 105 | | 105 | | | | 105 | |

TABLE 3

| Composition (pbw) | Comparative Example | | |
|---|---|---|---|
| | 1 | 2 | 3 |
| Polymer A | 80 | | 40 |
| Polymer E | | 80 | |
| Polymer K | | | 40 |
| PAG7 | | 3 | 0.5 |
| PAG8 | 2 | | |
| PAG9 | 1 | | 2.5 |
| Dissolution inhibitor | | | |
| Basic compound A | 0.125 | | |
| Basic compound B | | 0.125 | 0.125 |
| Organic acid derivative A | | | 0.5 |
| Organic acid derivative B | | | |
| Surfactant A | 0.25 | 0.25 | |
| Surfactant B | | | 0.25 |
| UV absorber | | | |
| Solvent A | 385 | 385 | 385 |
| Solvent B | | | |

TABLE 4

| | Sensitivity (mj/cm$^2$) | Resolution ($\mu$m) | Profile | DOF at 0.18 $\mu$m ($\mu$m) | Off-focus profile* | 24 hr PED dimensional stability (nm) |
|---|---|---|---|---|---|---|
| Example 1 | 34 | 0.14 | rectangular | 1.0 | rectangular | −8 |
| Example 2 | 36 | 0.14 | rectangular | 1.1 | rectangular | −10 |
| Example 3 | 45 | 0.15 | rectangular | 1.0 | rectangular | −8 |
| Example 4 | 30 | 0.14 | rectangular | 1.0 | rectangular | −8 |
| Example 5 | 36 | 0.14 | rectangular | 1.0 | rectangular | −10 |
| Example 6 | 41 | 0.16 | rectangular | 1.1 | rectangular | −8 |
| Example 7 | 42 | 0.15 | rectangular | 1.0 | rectangular | −10 |
| Example 8 | 38 | 0.14 | rectangular | 1.0 | rectangular | −9 |
| Example 9 | 34 | 0.16 | rectangular | 1.1 | rectangular | −10 |
| Example 10 | 34 | 0.14 | rectangular | 1.0 | rectangular | −8 |
| Example 11 | 38 | 0.18 | rectangular | 0.8 | rectangular | −8 |
| Example 12 | 35 | 0.15 | rectangular | 1.0 | rectangular | −10 |
| Example 13 | 30 | 0.15 | rectangular | 1.0 | rectangular | −8 |
| Example 14 | 36 | 0.15 | rectangular | 1.0 | rectangular | −8 |
| Example 15 | 40 | 0.14 | rectangular | 1.1 | rectangular | −10 |
| Example 16 | 42 | 0.15 | rectangular | 1.1 | rectangular | −8 |
| Example 17 | 35 | 0.14 | rectangular | 1.0 | rectangular | −10 |
| Example 18 | 34 | 0.14 | rectangular | 1.1 | rectangular | −9 |
| Example 19 | 41 | 0.16 | rectangular | 1.0 | rectangular | −10 |
| Example 20 | 42 | 0.15 | rectangular | 1.0 | rectangular | −10 |
| Example 21 | 38 | 0.14 | rectangular | 1.0 | rectangular | −8 |
| Example 22 | 41 | 0.15 | rectangular | 1.1 | rectangular | −8 |
| Example 23 | 38 | 0.14 | rectangular | 1.1 | rectangular | −10 |
| Example 24 | 40 | 0.15 | rectangular | 0.8 | rectangular | −8 |
| Comparative Example 1 | 50 | 0.18 | rectangular | 0.8 | rectangular | −10 |
| Conparative Example 2 | 35 | 0.17 | rectangular | 0.8 | forward taper | −8 |
| Comparative Example 3 | 36 | 0.17 | forward taper | 0.8 | forward taper | −10 |

*the shape of a pattern obtained when the focus was shifted −0.4 $\mu$m to minus side upon DOF measurement at 0.18 $\mu$m

TABLE 5

| | Dissolution | Application | 100 day storage stability | Debris after development | Foreign particles after peeling |
|---|---|---|---|---|---|
| Example 1 | good | good | good | good | good |
| Example 2 | good | good | good | good | good |
| Example 3 | good | good | good | good | good |
| Example 4 | good | good | good | good | good |
| Example 5 | good | good | good | good | good |
| Example 6 | good | good | good | good | good |
| Example 7 | good | good | good | good | good |
| Example 8 | good | good | good | good | good |
| Example 9 | good | good | good | good | good |
| Example 10 | good | good | good | good | good |
| Example 11 | good | good | good | good | good |
| Example 12 | good | good | good | good | good |
| Example 13 | good | good | good | good | good |
| Example 14 | good | good | good | good | good |
| Example 15 | good | good | good | good | good |
| Example 16 | good | good | good | good | good |
| Example 17 | good | good | good | good | good |
| Example 18 | good | good | good | good | good |
| Example 19 | good | good | good | good | good |
| Example 20 | good | good | good | good | good |
| Example 21 | good | good | good | good | good |
| Example 22 | good | good | good | good | good |
| Example 23 | good | good | good | good | good |
| Example 24 | good | good | good | good | good |
| Comparative Example 1 | good | good | good | poor | poor |
| Comparative Example 2 | good | good | good | unacceptable | unacceptable |
| Comparative Example 3 | good | good | good | unacceptable | poor |

There have been described photoacid generators in the form of O-arylsulfonyloxime compounds capable of generating arylsulfonyloxyarylsulfonic acids upon exposure to actinic radiation and chemically amplified resist compositions comprising the same. Due to the inclusion of arylsulfonyloxyarylsulfonyl group in O-arylsulfonyloxime, the compositions have many advantages including improved resolution, improved focus latitude, minimized line width variation or shape degradation even on long-term PED, and improved pattern profile after development. Because of high resolution, the compositions are suited for microfabrication, especially by deep UV lithography.

Japanese Patent Application No. 2002-080649 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A photoacid generator for chemically amplified resist compositions, having the following general formula (1):

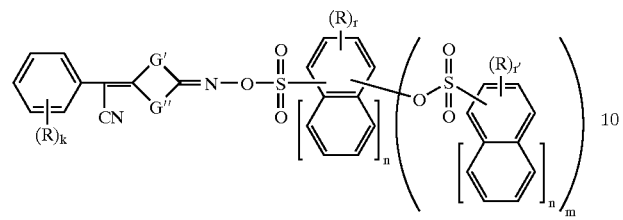

(1)

wherein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, k is an integer of 0 to 4, and G' and Gin" each are a sulfur atom or —CH=CH—, excluding the case where both G' and G" are sulfur atoms.

2. A photoacid generator for chemically amplified resist compositions, having the following general formula (1a):

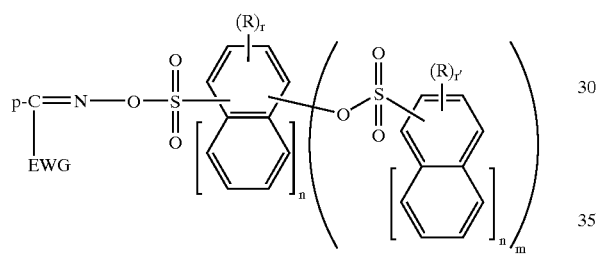

(1a)

wherein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, EWG is a cyano group, nitro group or perfluoroalkyl group of 1 to 3 carbon atoms, and p is a substituted or unsubstituted, straight, branched or cyclic alkyl group of 1 to 10 carbon atoms or substituted or unsubstituted aryl group of 6 to 12 carbon atoms.

3. A photoacid generator for chemically amplified resist compositions, having the following general formula (1b):

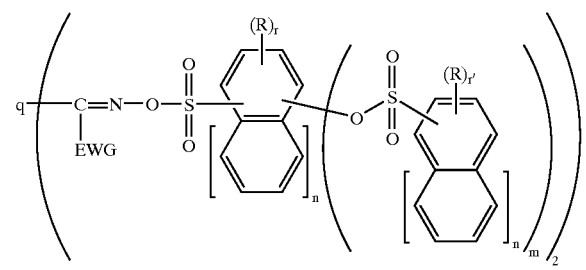

(1b)

wherein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, EWG is a cyano group, nitro group or perfluoroalkyl group of 1 to 3 carbon atoms, and q is a substituted or unsubstituted, straight, branched or cyclic alkylene group of 1 to 10 carbon atoms or substituted or unsubstituted arylene group of 6 to 18 carbon atoms.

4. A photoacid generator for chemically amplified resist compositions, having the following general formula (1c):

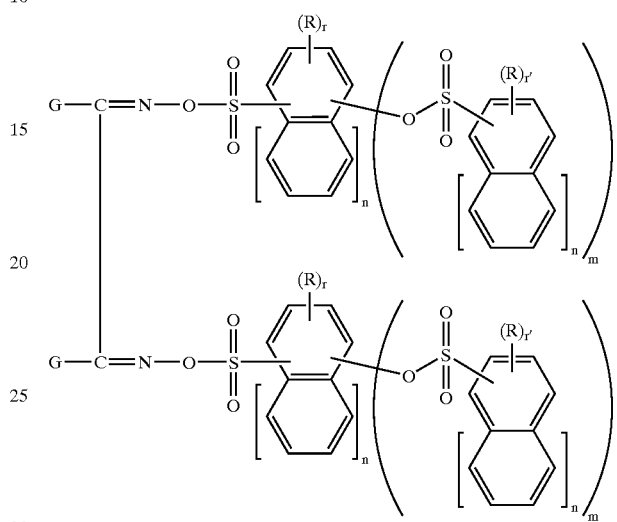

(1c)

wherein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, r' is an integer of 0 to 5, and G is a hydrogen atom, substituted or unsubstituted, straight, branched or cyclic alkyl group of 1 to 10 carbon atoms or substituted or unsubstituted aryl group of 6 to 12 carbon atoms, or two G's taken together may form a cyclic structure with the carbon atoms to which the G's are attached.

5. A chemically amplified resist composition comprising
   (A) a resin which changes its solubility in an alkaline developer under the action of an acid, and
   (B) the photoacid generator of claim 1.

6. A chemically amplified positive resist composition comprising
   (A) a resin which changes its solubility in an alkaline developer under the action of an acid, and
   (B) the photoacid generator of claim 1.

7. The resist composition of claim 5, further comprising (C) a compound capable of generating an acid upon exposure to radiation, other than component (B).

8. The resist composition of claim 5 wherein the resin (A) has such substituent groups having C—O—C linkages that the solubility in an alkaline developer changes as a result of scission of the C—O—C linkages under the action of an acid.

9. The resist composition of claim 8 wherein the resin (A) is a polymer containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl groups, the polymer having a weight average molecular weight of 3,000 to 100,000.

10. The resist composition of claim 8 wherein the resin (A) is a polymer comprising recurring units of the following general formula (2a):

(2a)

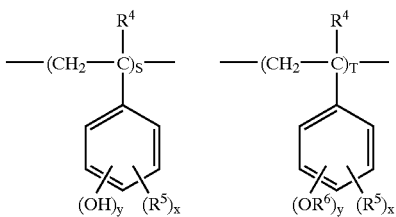

wherein R⁴ is hydrogen or methyl, R⁵ is a straight, branched or cyclic alkyl group of 1 to 8 carbon atoms, x is 0 or a positive integer, y is a positive integer, satisfying x+y≦5, R⁶ is an acid labile group, S and T are positive integers, satisfying 0≦T/(S+T)≦0.8, wherein the polymer contains units in which hydrogen atoms of phenolic hydroxyl groups are partially substituted with acid labile groups of one or more types, a proportion of the acid labile group-bearing units is on the average from more than 0 mol % to 80 mol % based on the entire polymer, and the polymer has a weight average molecular weight of 3,000 to 100,000.

11. The resist composition of claim 8 wherein the resin (A) is a polymer comprising recurring units of the following general formula (2a'):

(2a')

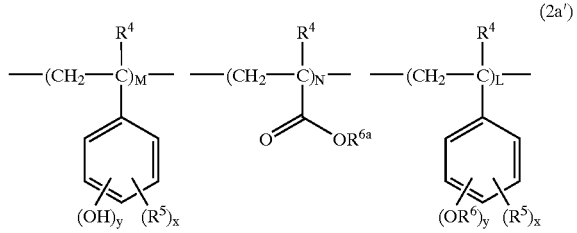

wherein R⁴ is hydrogen or methyl, R⁵ is a straight, branched or cyclic alkyl group of 1 to 8 carbon atoms, R⁶ is an acid labile group, R⁶ᵃ is hydrogen or an acid labile group, at least some of R⁶ᵃ being acid labile groups, x is 0 or a positive integer, y is a positive integer, satisfying x+y≦5, M and N are positive integers, L is 0 or a positive integer, satisfying 0<N/(M+N+L)≦0.5 and 0≦(N+L)/(M+N+L)≦0.8, wherein the polymer contains on the average from more than 0 mol % to 50 mol % of those units based on acrylate and methacrylate, and also contains on the average from more than 0 mol % to 80 mol % of acid labile group-bearing units, based on the entire polymer, and the polymer has a weight average molecular weight of 3,000 to 100,000.

12. The resist composition of claim 8 wherein the resin (A) is a polymer comprising recurring units of the following general formula (2a"):

(2a")

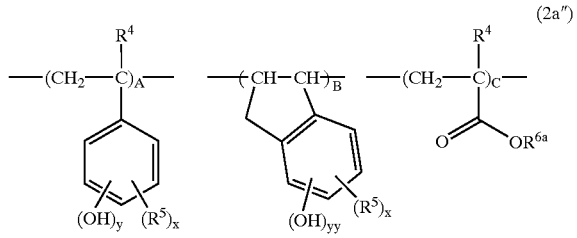

wherein R⁴ is hydrogen or methyl, R⁵ is a straight, branched or cyclic alkyl group of 1 to 8 carbon atoms, R⁶ is an acid labile group, R⁶ᵃ is hydrogen or an acid labile group, at least some of R⁶ᵃ being acid labile groups, x is 0 or a positive integer, y is a positive integer, satisfying x+y≦5, yy is 0 or a positive integer, satisfying x+yy≦4, A and B are positive integers, C, D and E each are 0 or a positive integer, satisfying 0<(B+E)/(A+B+C+D+E)≦0.5 and 0<(C+D+E)/(A+B+C+D+E)≦0.8, wherein the polymer contains on the average from more than 0 mol % to 50 mol % of those units based on indene and/or substituted indene, and also contains on the average from more than 0 mol % to 80 mol % of acid labile group-bearing units, based on the entire polymer, and the polymer has a weight average molecular weight of 3,000 to 100,000.

13. The resist composition of claim 9 wherein the acid labile group is selected from the class consisting of groups of the following general formulae (4) to (7), tertiary alkyl groups of 4 to 20 carbon atoms, trialkylsilyl groups whose alkyl moieties each have 1 to 6 carbon atoms, oxoalkyl groups of 4 to 20 carbon atoms, and aryl-substituted alkyl groups of 7 to 20 carbon atoms, (4)

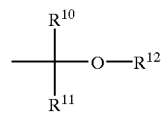

(5)

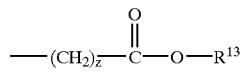

(6)

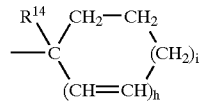

(7)

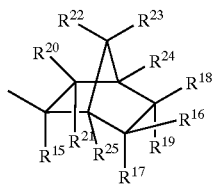

wherein R¹⁰ and R¹¹ each are hydrogen or a straight, branched or cyclic alkyl group having 1 to 18 carbon atoms, and R¹² is a monovalent hydrocarbon group of 1 to 18 carbon atoms which may contain a heteroatom, a pair of R¹⁰ and R¹¹, R¹⁰ and R¹², or R¹¹ and R¹² may together form a ring, with the proviso that R¹⁰, R¹¹, and R¹² each are a straight or branched alkylene of 1 to 18 carbon atoms when they form a ring, R¹³ is a tertiary alkyl group of 4 to 20 carbon atoms, a trialkysilyl group whose alkyl moieties each have 1 to 6 carbon atoms, an oxoalkyl group of 4 to 20 carbon atoms, or a group of the formula (4), z is an integer of 0 to 6, $R^{14}$ is a straight, branched or cyclic alkyl group of 1 to 8 carbon atoms or an aryl group of 6 to 20 carbon atoms which may be substituted, h is 0 or 1, i is 0, 1, 2 or 3, satisfying 2h+i=2 or 3, $R^{15}$ is a straight, branched or cyclic alkyl group of 1 to 8 carbon atoms or an aryl group of 6 to 20 carbon atoms which may be substituted, $R^{16}$ to $R^{25}$ are each independently hydrogen or a monovalent hydrocarbon group of 1 to 15 carbon atoms which may contain a heteroatom, $R^{16}$ to $R^{25}$, taken together, may form a ring, each of $R^{16}$ to $R^{25}$ divalent hydrocarbon group of 1 to 15 carbon atoms which may contain a heteroatom when they form a ring, or two of $R^{16}$ to $R^{25}$ which are attached to adjoining carbon atoms may bond together directly to form a double bond.

14. The resist composition of claim 5, further comprising (D) a basic compound.

15. The resist composition of claim 5, further comprising (E) an organic acid derivative.

16. The resist composition of claim 5, further comprising an organic solvent which contains a propylene glycol alkyl ether acetate, an alkyl lactate or a mixture thereof.

17. A process for forming a pattern, comprising the steps of:
applying the resist composition of claim 5 onto a substrate to form a coating,
heat treating the coating and exposing the coating to high energy radiation with a wavelength of up to 300 nm or electron beam through a photomask,
optionally heat treating the exposed coating, and developing the coating with a developer.

18. A chemically amplified resist composition comprising
(A) a resin which changes its solubility in an alkaline developer under the action of an acid, and
(B) a photoacid generator in the form of an O-arylsulfonyloxime compound for chemically amplified resist compositions, capable of generating, upon exposure to ultraviolet radiation, deep ultraviolet radiation, electron beams, x-rays, excimer laser beams, gamma-rays or synchrotron radiation, an arylsulfonyloxyarylsulfonic acid having the following general formula (1'):

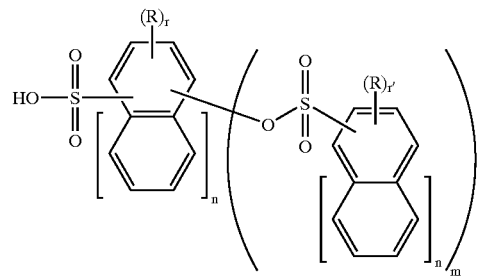

wherein R which may be the same or different is a hydrogen atom, fluorine atom, chlorine atom, nitro group, or substituted or unsubstituted, straight, branched or cyclic alkyl or alkoxy group of 1 to 12 carbon atoms, n is 0 or 1, m is 1 or 2, r is an integer of 0 to 4, and r' is an integer of 0 to 5.

19. A chemically amplified resist composition comprising
(A) a resin which changes its solubility in an alkaline developer under the action of an acid, and
(B) the photoacid generator of claim 2.

20. A chemically amplified resist composition comprising
(A) a resin which changes its solubility in an alkaline developer under the action of an acid, and
(B) the photoacid generator of claim 3.

21. A chemically amplified resist composition comprising
(A) a resin which changes its solubility in an alkaline developer under the action of an acid, and
(B) the photoacid generator of claim 4.

* * * * *